(12) United States Patent
Yang et al.

(10) Patent No.: US 11,041,164 B2
(45) Date of Patent: Jun. 22, 2021

(54) GENES FOR ENHANCING DROUGHT AND HEAT TOLERANCE IN PLANTS AND METHODS OF USE

(71) Applicant: UT-Battelle, LLC, Oak Ridge, TN (US)

(72) Inventors: Xiaohan Yang, Knoxville, TN (US); Gerald A. Tuskan, Oak Ridge, TN (US); Degao Liu, Oak Ridge, TN (US); Rongbin Hu, Knoxville, TN (US); Jin-Gui Chen, Oak Ridge, TN (US); Meng Xie, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 337 days.

(21) Appl. No.: 16/015,732

(22) Filed: Jun. 22, 2018

(65) Prior Publication Data

US 2018/0371487 A1   Dec. 27, 2018

Related U.S. Application Data

(60) Provisional application No. 62/523,294, filed on Jun. 22, 2017.

(51) Int. Cl.
*C12N 15/82* (2006.01)
*C12N 9/88* (2006.01)
*C07K 14/415* (2006.01)

(52) U.S. Cl.
CPC ........ *C12N 15/8273* (2013.01); *C07K 14/415* (2013.01); *C12N 9/88* (2013.01); *C12Y 401/01031* (2013.01)

(58) Field of Classification Search
None
See application file for complete search history.

(56) References Cited

U.S. PATENT DOCUMENTS

2002/0160378 A1* 10/2002 Harper ................. C12Q 1/6837
435/6.14

OTHER PUBLICATIONS

Huang et al. (Journal of integrative plant biology 50.10 (2008): 1230-1237). (Year: 2008).*
Cai et al. (Nature genetics 47.1 (2015): 65-72). (Year: 2015).*
Deng et al. (Molecular phylogenetics and evolution 94 (2016): 559-564). (Year: 2016).*
Wang G. et al., "A tomato chloroplast-targeted DnaJ protein protects Rubisco activity under heat stress", Journal of Experimental Botany (2015), vol. 66, No. 11, pp. 3027-3040.
Salvucci M.E., "Association of Rubisco activase with chaperonin-60β: a possible mechanism for protecting photosynthesis during heat stress", Journal of Experimental Botany (2008), vol. 59, No. 7, pp. 1923-1933.
Carrier G. et al., "An efficient and rapid protocol for plant nuclear DNA preparation suitable for next generation sequencing methods", American Journal of Botany (2011), pp. e13-e15.
Liu C. et al., "Coupled chaperone action in folding and assembly of hexadecameric Rubisco", Nature (2010), vol. 463, pp. 197-202.
Zhang S. et al., "Functional Partition of Cpon60α and Cpn60β Subunits in Substrate Recognition and Cooperation with Co-chaperonins", Molecular Plant (2016), 9, pp. 1210-1213.

* cited by examiner

*Primary Examiner* — Charles Logsdon
(74) *Attorney, Agent, or Firm* — Scully, Scott, Murphy & Presser, P.C.

(57) ABSTRACT

The present disclosure provides methods for increasing drought resistance and heat resistance of a plant. The methods encompass expression of at least one heat shock protein (HSP) from the group consisting of HSP40, HSP60 or HSP70 together with a phosphoenolpyruvate carboxylase (PEPC) comprising an aspartic acid (D) at a position that corresponds to the position 509 of SEQ ID NO: 4, in the plant. In comparison to a plant not manipulated in this manner, the disclosed, genetically-modified, plants display improved drought resistance and heat resistance. Also provided are plants that can be obtained by the method according to the invention, and nucleic acid vectors to be used in the described methods.

28 Claims, 16 Drawing Sheets
(14 of 16 Drawing Sheet(s) Filed in Color)
Specification includes a Sequence Listing.

| Tribe_id | Name | Gene locus | Definition | Gene Expression (FPKM)* | Gene Co-expression module** |
|---|---|---|---|---|---|
| ISO_F00796 | β-CA | Kaladp0824s0123.1 | beta carbonic anhydrase 2 | 18.35 | MEpink |
| ISO_F00796 | β-CA | Kaladp0834s0035.1 | beta carbonic anhydrase 2 | 277.08 | MEsalmon |
| ISO_F00796 | β-CA | Kaladp0834s0057.1 | beta carbonic anhydrase 2 | 155.98 | MEsalmon |
| ISO_F00796 | β-CA | Kaladp0081s0140.1 | beta carbonic anhydrase 5 | 1.14 | MEmagenta |
| ISO_F00796 | β-CA | Kaladp0081s0143.1 | beta carbonic anhydrase 5 | 2.39 | MElightcyan |
| ISO_F00796 | β-CA | Kaladp0538s0011.1 | beta carbonic anhydrase 2 | 66.8 | MEtan |
| ISO_F00022 | PPCK | Kaladp0837s0517.1 | Phosphoenolpyruvate carboxylase kinase 1 | 1187.84 | MEblack |
| ISO_F00022 | PPCK | Kaladp0950s0014.1 | Phosphoenolpyruvate carboxylase kinase 1 | 57.58 | MElightyellow |
| ISO_F00022 | PPCK | Kaladp0825s0192.1 | Phosphoenolpyruvate carboxylase kinase 1 | 6.62 | MEpurple |
| ISO_F00022 | PPCK | Kaladp0084s0601.1 | Phosphoenolpyruvate carboxylase kinase 1 | 376.3 | MEhighgreen |
| ISO_F00807 | PEPC | Kaladp0811s0355.1 | phosphoenolpyruvate carboxylase 3 | 10.79 | MEtan |
| ISO_F00807 | PEPC | Kaladp0011s1335.1 | phosphoenolpyruvate carboxylase 3 | 3.29 | MEgrey |
| ISO_F00807 | PEPC | Kaladp0048s0578.1 | phosphoenolpyruvate carboxylase 3 | 280.38 | MEblack |
| ISO_F00807 | PEPC | Kaladp0062s0053.1 | phosphoenolpyruvate carboxylase 4 | 18.51 | MEpink |
| ISO_F00807 | PEPC | Kaladp0095s0035.1 | phosphoenolpyruvate carboxylase 3 | 8338.11 | MEblack |
| ISO_F00814 | MDH | Kaladp0011s0257.1 | malate dehydrogenase | 383.29 | MEgrey |
| ISO_F00814 | MDH | Kaladp0022s0111.1 | malate dehydrogenase | 43.82 | MEpink |
| ISO_F00814 | MDH | Kaladp0048s0189.1 | malate dehydrogenase | 4.27 | MEgrey |
| ISO_F00814 | MDH | Kaladp0058s0569.1 | malate dehydrogenase | 180.19 | MEblue |
| ISO_F00814 | MDH | Kaladp0095s0052.1 | malate dehydrogenase | 107.8 | MEbrown |
| ISO_F00814 | MDH | Kaladp0897s0364.1 | malate dehydrogenase | 1.17 | MEgreenyellow |
| ISO_F00614 | MDH | Kaladp0101s0211.1 | malate dehydrogenase | 236.21 | MEtan |
| ISO_F00882 | MDH | Kaladp0082s0194.1 | malate dehydrogenase | 1925.18 | MEblue |
| ISO_F00882 | MDH | Kaladp0093s0388.1 | malate dehydrogenase | 3.08 | MEturquoise |
| ISO_F00882 | MDH | Kaladp1038s0012.1 | malate dehydrogenase | 19.58 | MEturquoise |
| ISO_F00831 | MDH | Kaladp0068s0169.1 | malate dehydrogenase | 226.83 | MEturquoise |
| ISO_F04944 | MDH | Kaladp0101s0012.1 | malate dehydrogenase | 60.4 | MEsalmon |
| ISO_F00112 | ALMT | Kaladp0824s0194.1 | Tonoplast aluminum-activated malate transporter | 147.01 | MEpink |
| ISO_F00112 | ALMT | Kaladp0048s0830.1 | Tonoplast aluminum-activated malate transporter | 8.52 | MEturquoise |
| ISO_F00112 | ALMT | Kaladp0050s0298.1 | Tonoplast aluminum-activated malate transporter | 2.49 | MEtan |
| ISO_F00112 | ALMT | Kaladp0062s0038.1 | Tonoplast aluminum-activated malate transporter | 66.11 | MEblack |

*The maximum expression level in the in the mature leaf during 24-hour period, as revealed by RNA-seq analysis.

FIG. 3C

| Tribe_id | Name | Gene locus | Definition | Gene Expression (FPKM)* | Gene Co-expression module** |
|---|---|---|---|---|---|
| ISO_F04828 | TDT | Kaladp0842s0251.1 | Tonoplast dicarboxylate transporter | 1617.63 | MEsalmon |
| ISO_F03433 | PPDK | Kaladp0039s0092.1 | Pyruvate, orthophosphate dikinase | 4744.54 | MEpink |
| ISO_F03433 | PPDK | Kaladp0076s0029.1 | Pyruvate, orthophosphate dikinase | 9054.27 | MEsalmon |
| ISO_F05114 | PPDK-RP | Kaladp0010s0106.1 | PPDK regulatory protein | 121.13 | MEblue |
| ISO_F02114 | PPDK-RP | Kaladp0606s0363.1 | PPDK regulatory protein | 81.78 | MEblue |
| ISO_F01811 | PEPCK | Kaladp0023s0088.1 | phosphoenolpyruvate carboxykinase 1 | 17.40 | MEgrey |
| ISO_F01811 | PEPCK | Kaladp0040s0194.1 | phosphoenolpyruvate carboxykinase 1 | 78.13 | MEturquoise |
| ISO_F01811 | PEPCK | Kaladp1116s0004.1 | phosphoenolpyruvate carboxykinase 1 | 9.04 | MEgrey |
| ISO_F08472 | NAD-ME | Kaladp0018s0130.1 | NAD-dependent malic enzyme | 21.76 | MEcyan |
| ISO_F08472 | NAD-ME | Kaladp0015s0134.1 | NAD-dependent malic enzyme | 20.74 | MEgrey |
| ISO_F08472 | NAD-ME | Kaladp0036s0124.1 | NAD-dependent malic enzyme | 269.31 | MEpink |
| ISO_F08472 | NAD-ME | Kaladp0037s0467.1 | NAD-dependent malic enzyme | 83.61 | MEgreen |
| ISO_F08472 | NAD-ME | Kaladp0063s0037.1 | NAD-dependent malic enzyme | 36.49 | MEcyan |
| ISO_F08472 | NAD-ME | Kaladp0472s0027.1 | NAD-dependent malic enzyme | 12.8 | MEmidnightblue |
| ISO_F08472 | NADP-ME | Kaladp0024s0016.1 | NADP-malic enzyme 4 | 1.01 | MEgrey |
| ISO_F08472 | NADP-ME | Kaladp0045s0427.1 | NADP-malic enzyme 4 | 204.39 | MEturquoise |
| ISO_F08472 | NADP-ME | Kaladp0092s0166.1 | NADP-malic enzyme 4 | 2849.96 | MEsalmon |

*The maximum expression level in the in the mature leaf during 24-hour period, as revealed by RNA-seq analysis.

| | | |
|---|---|---|
| Kaladp0048s0578.1 | PLFGPDLPKTEEIADVLGTFDVIAELPSDNFGAYIISMATSPSDVLAVEL | (SEQ ID NO:24) |
| Kaladp0011s0355.1 | PLFGPDLPKTEEIADVLGTFDVIAELPADNFGAYIISMATSPSDVLAVEL | (SEQ ID NO:25) |
| Kalax.0104s0064.1 | PLFGPDLPKTEEIADVLGTFDVIAELPADNFGAYIISMATSPSDVLAVEL | (SEQ ID NO:26) |
| Kalax.0283s0047.1 | PLFGPDLPKTEEIADVLGTFDVIAELPADNFGAYIISMATSPSDVLAVEL | (SEQ ID NO:27) |
| Kalax.0445s0035.1 | PLFGPDLPKTEEIADVLGTFDVIAELPSDNFGAYIISMATSPSDVLAVEL | (SEQ ID NO:28) |
| Kalax.0510s0003.1 | PLFGSDLPKTEEIADVLGAFDVIAELPSDNFGAYIISMATSPSDVLAVEL | (SEQ ID NO:29) |
| AAM95946.1 | PLFGSDLPKTEEIADVLGAFDVIAELPSDGFGAYIISMATATSDVLAVEL | (SEQ ID NO:30) |
| XP_020584551.1 | PLFGSDLPKTEEIADVLDTFHVIAELPSDNFGAYIISMATAPSDVLAVEL | (SEQ ID NO:31) |
| PWZ12751.1 | PLFGPDLPKTEEIADVLDTFHVIAELPSDSFGAYIISMATAASDVLAVEL | (SEQ ID NO:32) |
| XP_024436919.1 | PLFGPDLPKTEEIADVLDTFHVIAELPSDSFGAYIISMATAASDVLAVEL | (SEQ ID NO:33) |
| XP_013628861.1 | PLFGDLPKTEEIADVLDTFHVIAELPSDSFGAYIISMATAPSDVLAVEL | (SEQ ID NO:34) |
| XP_009106983.1 | PLFGSDLPKTEEIADVLDTFHVIAELPSDNFGAYIISMATAPSDVLAVEL | (SEQ ID NO:35) |
| XP_008362419.1 | PLFGADVPKTEEIADVLDTFHVIAELPSDNFGAYIISMATSPSDVLAVEL | (SEQ ID NO:36) |
| XP_003527347.1 | PLFGPDLPKTEEIADVLETFHVIAELPSDSFGAYIISMATAPSDVLSVEL | (SEQ ID NO:37) |

SEQUENCE LISTING

<160> NUMBER OF SEQ ID NOS: 84

<210> SEQ ID NO 1
<211> LENGTH: 954
<212> TYPE: PRT
<213> ORGANISM: x Mokara cv. 'Yellow'

<400> SEQUENCE: 1

```
Met Ala Lys Ala Ser Val Ala Lys Leu Pro Ser Met Asp Ala His Leu
 1               5                  10                  15

Arg Leu Leu Ala Pro Gly Lys Val Ser Asp Asp Asp Lys Leu Val Glu
             20                  25                  30
```

```
Tyr Asp Ala Met Leu Leu Asp Arg Phe Leu Glu Ile Val Gln Asp Leu
             35                  40                  45

His Gly Glu Gly Ile Arg Glu Thr Val Gln Glu Cys Tyr Glu Leu Ser
     50                  55                  60

Ala Glu Tyr Glu Arg Thr His Asp Ser Lys Lys Leu Asp Glu Leu Gly
 65                  70                  75                  80

Asn Val Leu Thr Ser Leu Glu Pro Gly Asp Ser Ile Val Val Ala Ser
                 85                  90                  95

Ser Phe Ser His Met Leu Asn Leu Ala Asn Leu Ala Glu Glu Val Gln
                100                 105                 110

Ile Ala Gln Arg Arg Thr Lys Pro Lys Lys Gly Tyr Phe Glu Ser
            115                 120                 125

Asn Leu Glu Glu Thr Phe Lys Arg Leu Ile Gly Glu Leu Lys Lys Thr
        130                 135                 140

Pro Glu Glu Ile Phe Asp Ala Leu Lys Asn Gln Thr Val Asp Leu Val
145                 150                 155                 160

Phe Thr Ala His Pro Thr Gln Ser Ile Arg Arg Ser Leu Leu Gln Lys
                165                 170                 175

His Gly Arg Ile Arg Asn Ser Leu Thr Gln Leu Cys Ala Lys Asp Ile
            180                 185                 190

Thr Pro Asp Glu Lys Gln Glu Leu Asp Glu Ala Leu Gln Arg Glu Ile
        195                 200                 205

Gln Ala Ala Phe Arg Thr Asp Glu Ile Arg Arg Thr Gln Pro Gln Pro
210                 215                 220

Gln Asp Glu Met Arg Ala Gly Met Ser Tyr Phe His Glu Thr Ile Trp
225                 230                 235                 240

Lys Gly Val Pro Lys Phe Leu Arg Arg Val Asp Thr Ala Pro Lys Ser
                245                 250                 255

Ile Gly Ile Asn Glu Arg Leu Pro Tyr Asn Ala Pro Leu Ile Gln Phe
            260                 265                 270

Ser Ser Trp Met Gly Gly Asp Arg Asp Gly Asn Pro Arg Val Thr Pro
        275                 280                 285

Glu Val Thr Arg Asp Val Cys Leu Leu Ala Arg Leu Met Ala Ala Asn
    290                 295                 300

Leu Tyr Phe Ser Gln Ile Glu Asp Leu Met Phe Glu Leu Ser Met Trp
305                 310                 315                 320

Arg Cys Ser Asp Glu Leu Arg Leu Arg Ala Asp Glu Leu His Arg Ser
                325                 330                 335

Ser Lys Lys Asp Ala Lys His Tyr Ile Glu Phe Trp Lys Lys Val Pro
            340                 345                 350

Pro Ser Glu Pro Tyr Arg Val Ile Leu Gly Asp Val Arg Asp Lys Leu
        355                 360                 365

Tyr Asn Thr Arg Glu Arg Ala Arg Gln Leu Leu Ser Ser Gly Ile Ser
    370                 375                 380

Asp Ile Pro Glu Glu Ala Thr Leu Thr Asn Val Glu Gln Phe Leu Glu
385                 390                 395                 400

Pro Leu Glu Leu Cys Tyr Arg Ser Leu Cys Ala Cys Gly Asp Ser Pro
                405                 410                 415

Ile Ala Asp Gly Ser Leu Leu Asp Phe Leu Arg Gln Val Ser Thr Phe
            420                 425                 430

Gly Leu Ser Leu Val Arg Leu Asp Ile Arg Gln Glu Ser Asp Arg His
        435                 440                 445
```

```
Thr Asp Val Leu Asp Ala Ile Thr Arg His Leu Gln Ile Gly Ser Tyr
    450                 455                 460
Arg Glu Trp Pro Glu Glu Lys Arg Gln Glu Trp Leu Leu Ser Glu Leu
465                 470                 475                 480
Arg Gly Lys Arg Pro Leu Phe Gly Ser Asp Leu Pro Lys Thr Glu Glu
                485                 490                 495
Ile Ala Asp Val Leu Gly Ala Phe Asp Val Ile Ala Glu Leu Pro Ser
                500                 505                 510
Asp Gly Phe Gly Ala Tyr Ile Ile Ser Met Ala Thr Ala Thr Ser Asp
            515                 520                 525
Val Leu Ala Val Glu Leu Leu Gln Arg Glu Ser Arg Val Lys Lys Pro
    530                 535                 540
Leu Arg Val Val Pro Leu Phe Glu Lys Leu Ala Asp Leu Glu Ala Ala
545                 550                 555                 560
Pro Ala Ala Val Glu Arg Leu Phe Ser Ile Asp Trp Tyr Arg Asn Arg
                565                 570                 575
Ile Asn Gly Lys Gln Glu Val Met Ile Gly Tyr Ser Asp Ser Gly Lys
                580                 585                 590
Gly Ala Gly Arg Leu Ser Ala Ala Trp Gln Leu Tyr Lys Ala Gln Glu
            595                 600                 605
Glu Leu Val Lys Val Ala Lys Glu Tyr Gly Val Lys Leu Thr Met Phe
    610                 615                 620
His Gly Arg Gly Gly Thr Val Gly Arg Gly Gly Pro Thr His Leu
625                 630                 635                 640
Ala Ile Leu Ser Gln Pro Pro Asp Thr Ile Leu Gly Ser Leu Arg Val
                645                 650                 655
Thr Val Gln Gly Glu Val Ile Glu Gln Ser Phe Gly Glu Glu Asn Leu
                660                 665                 670
Cys Phe Lys Thr Leu Gln Arg Tyr Thr Val Gly Thr Leu Glu His Gly
            675                 680                 685
Met Gln Leu Pro Ile Ser Pro Lys Pro Glu Trp Arg Ala Leu Met Asp
    690                 695                 700
Glu Met Ala Ile Val Ala Thr Glu Glu Tyr Arg Ser Val Val Phe Lys
705                 710                 715                 720
Glu Pro Arg Phe Val Glu Tyr Phe Arg Leu Ala Thr Pro Glu Leu Glu
                725                 730                 735
Tyr Gly Arg Met Asn Ile Gly Ser Arg Pro Ser Lys Arg Lys Pro Ser
                740                 745                 750
Gly Gly Ile Glu Ser Leu Arg Ala Ile Pro Trp Ile Phe Ala Trp Thr
            755                 760                 765
Gln Thr Arg Phe His Leu Pro Val Trp Leu Gly Phe Gly Ala Ala Phe
    770                 775                 780
Lys His Val Ile Lys Lys Asp Pro Lys Asn Leu Leu Ile Leu Arg Glu
785                 790                 795                 800
Met His Asn Asp Trp Pro Phe Phe Arg Val Thr Ile Asp Leu Ile Glu
                805                 810                 815
Met Val Phe Ser Lys Gly Asn Ser Gly Ile Ala Ala Leu Tyr Asp Lys
                820                 825                 830
Leu Leu Val Ser Pro Asp Leu Pro Phe Gly Glu Gln Leu Arg Ala
            835                 840                 845
Asn Tyr Glu Glu Thr Lys Asp Leu Leu Leu Gln Val Ala Asp His Lys
    850                 855                 860
Thr Leu Leu Glu Gly Asp Pro Tyr Leu Lys Gln Arg Leu Arg Leu Arg
```

```
                865                 870                 875                 880
Val Pro Tyr Ile Thr Thr Leu Asn Val Tyr Gln Ala Tyr Thr Leu Lys
                    885                 890                 895

Arg Ile Arg Glu Pro Asp Tyr Ala Val Pro His Ile Ser Asn Asp Lys
            900                 905                 910

Leu Asn Ser Asn Lys Thr Ala Ala Glu Leu Val Lys Leu Asn Pro Thr
            915                 920                 925

Ser Glu Tyr Ala Pro Gly Leu Glu Asp Thr Leu Ile Leu Thr Met Lys
    930                 935                 940

Gly Ile Ala Ala Gly Leu Gln Asn Thr Gly
945                 950

<210> SEQ ID NO 2
<211> LENGTH: 953
<212> TYPE: PRT
<213> ORGANISM: Phalaenopsis equestris

<400> SEQUENCE: 2

Met Ser Lys Ala Val Ala Lys Leu Pro Ser Met Asp Ala His Leu Arg
1               5                   10                  15

Leu Leu Ala Pro Ala Lys Val Ser Glu Asp Asp Lys Leu Val Glu Tyr
            20                  25                  30

Asp Ala Met Leu Leu Asp Arg Phe Leu Glu Ile Val Gln Asp Leu His
        35                  40                  45

Gly Glu Gly Ile Arg Glu Thr Val Gln Glu Cys Tyr Glu Leu Ser Ala
    50                  55                  60

Glu Tyr Glu Arg Thr His Asp Ser Lys Lys Leu Asp Glu Leu Gly Asn
65                  70                  75                  80

Val Leu Thr Ser Leu Asp Pro Gly Asp Ser Ile Val Val Ala Ser Ser
                85                  90                  95

Phe Ser His Met Leu Asn Leu Ser Asn Leu Ala Glu Glu Val Gln Ile
            100                 105                 110

Ala Gln Arg Arg Arg Thr Lys Pro Lys Lys Gly Tyr Phe Glu Ser Asn
        115                 120                 125

Leu Glu Glu Thr Phe Lys Arg Leu Ile Val Glu Leu Lys Lys Ser Pro
    130                 135                 140

Glu Glu Val Phe Asp Ala Leu Lys Asn Gln Thr Val Asp Leu Val Phe
145                 150                 155                 160

Thr Ala His Pro Thr Gln Ser Ile Arg Arg Ser Leu Leu Gln Lys His
                165                 170                 175

Gly Arg Ile Arg Asn Ser Leu Thr Gln Leu Cys Ala Lys Asp Ile Thr
            180                 185                 190

Pro Asp Glu Lys Gln Glu Leu Asp Glu Ala Leu Gln Arg Glu Ile Gln
        195                 200                 205

Ala Ala Phe Arg Thr Asp Glu Ile Arg Arg Thr Gln Pro Gln Pro Gln
    210                 215                 220

Asp Glu Met Arg Ala Gly Met Ser Tyr Phe His Glu Thr Ile Trp Lys
225                 230                 235                 240

Gly Val Pro Lys Phe Leu Arg Arg Val Asp Thr Ala Leu Lys Ser Ile
                245                 250                 255

Gly Ile Asn Glu Arg Leu Pro Tyr Asn Ala Pro Leu Ile Gln Phe Ser
            260                 265                 270

Ser Trp Met Gly Gly Asp Arg Asp Gly Asn Pro Arg Val Thr Pro Glu
    275                 280                 285
```

-continued

Val Thr Arg Asp Val Cys Leu Leu Ala Arg Leu Met Ala Ala Asn Leu
290                 295                 300

Tyr Phe Ser Gln Ile Glu Asp Leu Met Phe Glu Leu Ser Met Trp Arg
305                 310                 315                 320

Cys Ser Asn Glu Leu Arg Leu Arg Ala Asp Glu Leu His His Ser Ser
            325                 330                 335

Lys Lys Asp Ala Lys His Tyr Ile Glu Phe Trp Lys Lys Val Pro Pro
            340                 345                 350

Ser Glu Pro Tyr Arg Val Ile Leu Gly Asp Leu Arg Asp Lys Leu Tyr
        355                 360                 365

Asn Thr Arg Glu Arg Ala Arg Gln Leu Leu Ser Asn Gly Val Ser Asp
370                 375                 380

Ile Pro Glu Glu Ala Thr Leu Thr Asn Ile Glu Gln Phe Leu Glu Pro
385                 390                 395                 400

Leu Glu Leu Cys Tyr Arg Ser Leu Cys Ala Cys Gly Asp Ser Pro Ile
                405                 410                 415

Ala Asp Gly Ser Leu Leu Asp Phe Leu Arg Gln Val Ser Thr Phe Gly
            420                 425                 430

Leu Ser Leu Val Arg Leu Asp Ile Arg Gln Glu Ser Asp Arg His Thr
        435                 440                 445

Asp Val Leu Asp Ala Ile Thr Arg His Leu Gln Leu Gly Ser Tyr Arg
450                 455                 460

Glu Trp Pro Glu Glu Lys Arg Gln Glu Trp Leu Leu Ser Glu Leu Arg
465                 470                 475                 480

Gly Lys Arg Pro Leu Phe Gly Pro Asp Leu Pro Lys Thr Glu Glu Ile
                485                 490                 495

Ala Asp Val Leu Gly Ala Phe Asp Val Ile Ala Glu Leu Pro Ser Asp
            500                 505                 510

Gly Phe Gly Ala Tyr Val Ile Ser Met Ala Thr Ala Thr Ser Asp Val
        515                 520                 525

Leu Ala Val Glu Leu Leu Gln Arg Glu Ser His Val Lys Asn Pro Leu
530                 535                 540

Arg Val Val Pro Leu Phe Glu Lys Leu Ala Asp Leu Glu Ala Ala Pro
545                 550                 555                 560

Ala Ala Val Ala Arg Leu Phe Ser Ile Asp Trp Tyr Arg Asn Arg Ile
                565                 570                 575

Asn Gly Lys Gln Glu Val Met Ile Gly Tyr Ser Asp Ser Gly Lys Asp
            580                 585                 590

Ala Gly Arg Leu Ser Ala Ala Trp Gln Leu Tyr Lys Ala Gln Glu Glu
        595                 600                 605

Leu Val Lys Val Ala Lys Glu Tyr Gly Val Lys Leu Thr Met Phe His
610                 615                 620

Gly Arg Gly Gly Thr Val Gly Arg Gly Gly Pro Thr His Leu Ala
625                 630                 635                 640

Ile Leu Ser Gln Pro Pro Asp Thr Ile Leu Gly Ser Leu Arg Val Thr
                645                 650                 655

Val Gln Gly Glu Val Ile Glu Gln Ser Phe Gly Glu Glu Asn Leu Cys
            660                 665                 670

Phe Arg Thr Leu Gln Arg Tyr Thr Val Ala Thr Leu Glu His Gly Met
        675                 680                 685

Gln Leu Pro Ile Ser Pro Lys Pro Glu Trp Arg Ala Leu Met Asp Glu
690                 695                 700

Met Ala Ile Val Ala Thr Glu Glu Phe Arg Ser Ile Val Phe Lys Glu

```
                705                 710                 715                 720
Pro Arg Phe Val Glu Tyr Phe Arg Leu Ala Thr Pro Glu Leu Glu Tyr
                        725                 730                 735

Gly Arg Met Asn Ile Gly Ser Arg Pro Ser Lys Arg Lys Pro Ser Gly
                740                 745                 750

Gly Ile Glu Ser Leu Arg Ala Ile Pro Trp Ile Phe Ala Trp Thr Gln
                755                 760                 765

Thr Arg Phe His Leu Pro Val Trp Leu Gly Phe Gly Ala Ala Phe Lys
            770                 775                 780

His Val Ile Lys Lys Asp Pro Lys Asn Leu Leu Ile Leu Arg Glu Met
785                 790                 795                 800

His Asn Asp Trp Pro Phe Arg Val Thr Ile Asp Leu Ile Glu Met
                        805                 810                 815

Val Phe Ser Lys Gly Ser Ser Gly Ile Ala Ala Leu Tyr Asp Lys Leu
                820                 825                 830

Leu Val Ser Pro Asp Leu Leu Pro Phe Gly Glu Gln Leu Arg Ala Asn
                835                 840                 845

Tyr Glu Glu Thr Glu Asp Leu Leu Gln Val Ala Gly His Lys Ser
            850                 855                 860

Leu Leu Glu Gly Asp Pro Tyr Leu Lys Gln Arg Leu Arg Leu Arg Val
865                 870                 875                 880

Pro Tyr Ile Thr Thr Leu Asn Val Tyr Gln Ala Phe Thr Leu Lys Arg
                        885                 890                 895

Ile Arg Glu Pro Asn Tyr Ala Ile Pro His Ile Ser Asn Glu Lys Ser
                900                 905                 910

Asn Ser Asn Asn Thr Ala Ala Glu Leu Val Lys Leu Asn Pro Thr Ser
            915                 920                 925

Glu Tyr Ala Pro Gly Leu Glu Asp Thr Leu Ile Leu Thr Met Lys Gly
                930                 935                 940

Ile Ala Ala Gly Leu Gln Asn Thr Gly
945                 950

<210> SEQ ID NO 3
<211> LENGTH: 961
<212> TYPE: PRT
<213> ORGANISM: Kalanchoe fedtschenkoi

<400> SEQUENCE: 3

Met Lys Leu Glu Lys Met Ala Ser Ile Asp Ala His Leu Arg Leu Leu
1               5                   10                  15

Ala Pro Gly Lys Val Ser Glu Asp Asp Lys Leu Val Glu Tyr Asp Ala
                20                  25                  30

Leu Leu Leu Asp Arg Phe Leu Asp Ile Leu Gln Ala Leu His Gly Glu
            35                  40                  45

Asp Leu Lys Glu Thr Val Gln Glu Cys Tyr Glu Met Ser Ala Glu Tyr
        50                  55                  60

Glu Ser Ser His Asp Pro Glu Lys Leu Glu Glu Leu Gly Ser Val Leu
65                  70                  75                  80

Thr Ser Leu Asp Ala Gly Asp Ser Ile Val Val Ala Lys Ser Phe Ser
                85                  90                  95

His Met Leu Asn Leu Ala Asn Leu Ala Glu Glu Val Gln Ile Ala Tyr
                100                 105                 110

Arg Arg Arg Ile Lys Leu Lys Lys Gly Asp Phe Ala Asp Glu Ala Ser
            115                 120                 125
```

```
Ala Thr Thr Glu Ser Asp Ile Glu Glu Thr Ile Arg Lys Leu Val Lys
    130                 135                 140

Met Gly Lys Ser Asn Glu Glu Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Thr Gln Leu Tyr
            180                 185                 190

Ala Lys Asp Ile Thr Thr Asp Lys Lys Glu Leu Asp Glu Ala Leu
        195                 200                 205

Gln Arg Glu Ile Gln Ala Ala Phe Arg Thr Asp Glu Ile Arg Arg Thr
    210                 215                 220

Pro Pro Thr Pro Gln Asp Glu Met Arg Ala Gly Met Ser Tyr Phe His
225                 230                 235                 240

Glu Thr Ile Trp Lys Gly Val Pro Lys Phe Leu Arg Arg Val Asp Thr
                245                 250                 255

Ala Leu Lys Asn Val Gly Ile Thr Glu Arg Val Pro Tyr Asn Ala Pro
            260                 265                 270

Leu Ile Gln Phe Ser Ser Trp Met Gly Gly Asp Arg Asp Gly Asn Pro
        275                 280                 285

Arg Val Thr Pro Glu Val Thr Arg Asp Val Cys Leu Leu Ala Arg Met
    290                 295                 300

Met Ala Ala Asn Leu Tyr Phe Ser Gln Ile Glu Asp Leu Met Phe Glu
305                 310                 315                 320

Leu Ser Met Trp Arg Cys Asn Asp Glu Leu Arg Ala Arg Ala Asp Glu
                325                 330                 335

Leu His Arg Thr Ser Lys Arg Asp Ser Lys His Tyr Ile Glu Phe Trp
            340                 345                 350

Lys Gln Val Pro Pro Asn Glu Pro Tyr Arg Val Val Leu Ser Asp Val
        355                 360                 365

Arg Asp Lys Leu Tyr Tyr Thr Arg Glu His Ser Arg Gln Leu Leu Ser
    370                 375                 380

Asn Gly Val Ser Asp Val Pro Glu Val Leu Thr Phe Thr Asp Val Asp
385                 390                 395                 400

Gln Phe Leu Glu Pro Leu Glu Leu Cys Tyr Arg Ser Leu Cys Ala Cys
                405                 410                 415

Gly Asp Arg Pro Ile Ala Asp Gly Ser Leu Leu Asp Phe Leu Arg Gln
            420                 425                 430

Val Ser Thr Phe Gly Leu Ser Leu Val Arg Leu Asp Ile Arg Gln Glu
        435                 440                 445

Ser Glu Arg His Thr Asp Val Met Asp Ala Ile Thr Asn His Leu Gly
    450                 455                 460

Ile Gly Ser Tyr Arg Glu Trp Ser Glu Glu Lys Arg Gln Asp Trp Leu
465                 470                 475                 480

Leu Ser Glu Leu Lys Gly Lys Arg Pro Leu Phe Gly Pro Asp Leu Pro
                485                 490                 495

Lys Thr Glu Glu Ile Ala Asp Val Leu Gly Thr Phe Asp Val Ile Ala
            500                 505                 510

Glu Leu Pro Ala Asp Asn Phe Gly Ala Tyr Ile Ile Ser Met Ala Thr
        515                 520                 525

Ser Pro Ser Asp Val Leu Ala Val Glu Leu Leu Gln Arg Glu Cys Arg
    530                 535                 540

Val Lys His Pro Leu Arg Val Val Pro Leu Phe Glu Lys Leu Ala Asp
```

```
            545                 550                 555                 560
        Leu Glu Ala Ala Pro Ala Ala Val Ala Arg Leu Phe Ser Ile Asp Trp
                        565                 570                 575

Tyr Lys Asn Arg Ile Asp Gly Lys Gln Glu Val Met Ile Gly Tyr Ser
                        580                 585                 590

Asp Ser Gly Lys Asp Ala Gly Arg Leu Ser Ala Ala Trp Gln Leu Tyr
                        595                 600                 605

Lys Ala Gln Glu Asp Leu Val Lys Val Ala Lys Glu Phe Gly Val Lys
                        610                 615                 620

Leu Thr Met Phe His Gly Arg Gly Thr Val Gly Arg Gly Gly Gly
        625                 630                 635                 640

Pro Ala His Leu Ala Ile Leu Ser Gln Pro Asp Thr Ile Leu Gly
                        645                 650                 655

Ser Leu Arg Val Thr Val Gln Gly Glu Val Ile Glu Gln Ser Phe Gly
                        660                 665                 670

Glu Glu His Leu Cys Phe Arg Thr Leu Gln Arg Tyr Thr Ala Ala Thr
                        675                 680                 685

Leu Glu His Ser Met Cys Pro Pro Ala Ser Pro Glu Pro Glu Trp Arg
                        690                 695                 700

Ala Leu Leu Asp Glu Met Ala Val Thr Ala Thr Lys Glu Tyr Arg Ser
        705                 710                 715                 720

Val Val Phe Gln Glu Pro Arg Phe Val Glu Tyr Phe Arg Leu Ala Thr
                        725                 730                 735

Pro Glu Leu Glu Tyr Gly Arg Met Asn Ile Gly Ser Arg Pro Ser Lys
                        740                 745                 750

Arg Lys Pro Asn Gly Gly Ile Glu Ser Leu Arg Ala Ile Pro Trp Ile
                        755                 760                 765

Phe Ala Trp Thr Gln Thr Arg Phe His Leu Pro Val Trp Leu Gly Phe
                        770                 775                 780

Gly Ala Ala Phe Lys His Val Ile Asp Lys Asp Ile Lys Asn Leu Leu
        785                 790                 795                 800

Thr Leu Gln Glu Met Tyr Lys Arg Trp Pro Phe Phe Arg Val Thr Ile
                        805                 810                 815

Asp Leu Val Glu Met Val Phe Ala Lys Gly Asp Pro Gly Ile Ala Ala
                        820                 825                 830

Leu Tyr Asp Lys Leu Leu Val Ser Glu Asp Leu Trp Pro Phe Gly Glu
                        835                 840                 845

Gln Leu Arg Asn Asn Tyr Asn Glu Thr Lys Asn Leu Leu Leu Gln Val
                        850                 855                 860

Ala Gly His Lys Asp Leu Leu Glu Gly Asp Pro Tyr Leu Arg Gln Arg
        865                 870                 875                 880

Leu Arg Leu Arg Asp Ser Tyr Ile Thr Thr Leu Asn Val Cys Gln Ala
                        885                 890                 895

Tyr Thr Leu Lys Arg Ile Arg Asp Pro His Tyr His Val Thr Val Arg
                        900                 905                 910

Pro His Leu Ser Lys Glu Ile Thr Glu Ser Asn Lys Pro Ala Ala Glu
                        915                 920                 925

Leu Val Lys Leu Asn Pro Thr Ser Glu Tyr Ala Pro Gly Leu Glu Asp
                        930                 935                 940

Thr Leu Ile Leu Thr Met Lys Gly Ile Ala Ala Gly Met Gln Asn Thr
        945                 950                 955                 960

Gly
```

<210> SEQ ID NO 4
<211> LENGTH: 961
<212> TYPE: PRT
<213> ORGANISM: Kalanchoe fedtschenkoi

<400> SEQUENCE: 4

```
Met Lys Leu Glu Lys Met Ala Ser Ile Asp Ala His Leu Arg Leu Leu
1               5                   10                  15

Ala Pro Gly Lys Val Ser Glu Asp Asp Lys Leu Val Glu Tyr Asp Ala
            20                  25                  30

Leu Leu Leu Asp Arg Phe Leu Asp Ile Leu Gln Ala Leu His Gly Glu
        35                  40                  45

Asp Leu Lys Glu Thr Val Gln Glu Cys Tyr Glu Leu Ser Ala Glu Tyr
    50                  55                  60

Glu Ser Ser Arg Asp Pro Ala Lys Leu Glu Glu Leu Gly Ser Val Leu
65                  70                  75                  80

Thr Ser Leu Asp Ala Gly Asp Ser Ile Val Leu Ala Lys Ser Phe Ser
                85                  90                  95

His Met Leu Asn Leu Ala Asn Leu Ala Glu Glu Val Gln Ile Ala Tyr
            100                 105                 110

Arg Arg Arg Ile Lys Leu Lys Lys Gly Asp Phe Ala Asp Glu Ala Ser
        115                 120                 125

Ala Thr Thr Glu Ser Asp Ile Glu Glu Thr Ile Arg Lys Leu Val Lys
    130                 135                 140

Met Gly Lys Thr Ser Glu Gln Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Thr Gln Leu Tyr
            180                 185                 190

Ala Lys Asp Ile Thr Thr Asp Asp Lys Lys Glu Leu Asp Glu Ala Leu
        195                 200                 205

Gln Arg Glu Ile Gln Ala Ala Phe Arg Thr Asp Glu Ile Arg Arg Thr
    210                 215                 220

Pro Pro Thr Pro Gln Asp Glu Met Arg Ala Gly Met Ser Tyr Phe His
225                 230                 235                 240

Glu Thr Ile Trp Lys Gly Val Pro Lys Phe Leu Arg Arg Val Asp Thr
                245                 250                 255

Ala Leu Lys Asn Val Gly Ile Asn Glu Arg Val Pro Tyr Asn Ala Pro
            260                 265                 270

Leu Ile Gln Phe Ser Ser Trp Met Gly Gly Asp Arg Asp Gly Asn Pro
        275                 280                 285

Arg Val Thr Pro Glu Val Thr Arg Asp Val Cys Leu Leu Ala Arg Met
    290                 295                 300

Met Val Ala Asn Met Tyr Phe Ser Gln Ile Glu Asp Leu Met Phe Glu
305                 310                 315                 320

Leu Ser Met Trp Arg Cys Asn Asp Glu Leu Arg Ala Arg Ala Asp Glu
                325                 330                 335

Leu His Met Thr Ala Lys Arg Asp Ser Lys Gln Tyr Ile Glu Phe Trp
            340                 345                 350

Lys Gln Val Pro Pro Ser Glu Pro Tyr Arg Leu Val Leu Ser Asp Val
        355                 360                 365

Arg Asp Lys Leu Tyr His Thr Arg Glu His Ser Arg Gln Leu Leu Ser
    370                 375                 380
```

```
Asn Gly Val Ser Asp Val Pro Glu Glu Leu Ile Phe Thr Asp Val Asp
385                 390                 395                 400

Gln Phe Leu Glu Pro Leu Glu Leu Cys Tyr Arg Ser Leu Cys Ala Cys
            405                 410                 415

Gly Asp Arg Pro Ile Ala Asp Gly Ser Leu Leu Asp Phe Leu Arg Gln
        420                 425                 430

Val Ser Thr Phe Gly Leu Ser Leu Val Arg Leu Asp Ile Arg Gln Glu
        435                 440                 445

Ser Glu Arg His Thr Asp Val Met Asp Ala Ile Thr Asn His Leu Gly
    450                 455                 460

Ile Gly Ser Tyr Arg Glu Trp Ser Glu Glu Lys Arg Gln Asp Trp Leu
465                 470                 475                 480

Leu Ser Glu Leu Lys Gly Lys Arg Pro Leu Phe Gly Pro Asp Leu Pro
                485                 490                 495

Lys Thr Glu Glu Ile Ala Asp Val Leu Gly Thr Phe Asp Val Ile Ala
            500                 505                 510

Glu Leu Pro Ser Asp Asn Phe Gly Ala Tyr Ile Ile Ser Met Ala Thr
        515                 520                 525

Ser Pro Ser Asp Val Leu Ala Val Glu Leu Leu Gln Arg Glu Cys His
530                 535                 540

Val Lys His Pro Leu Arg Val Val Pro Leu Phe Glu Lys Leu Ala Asp
545                 550                 555                 560

Leu Glu Ala Ala Pro Ala Ala Val Ala Arg Leu Phe Ser Ile Asp Trp
                565                 570                 575

Tyr Lys Asn Arg Ile Asp Gly Lys Gln Glu Val Met Ile Gly Tyr Ser
            580                 585                 590

Asp Ser Gly Lys Asp Ala Gly Arg Leu Ser Ala Ala Trp Gln Leu Tyr
        595                 600                 605

Lys Ala Gln Glu Asp Leu Val Lys Val Ala Lys Glu Phe Gly Val Lys
        610                 615                 620

Leu Thr Met Phe His Gly Arg Gly Gly Thr Val Gly Arg Gly Gly Gly
625                 630                 635                 640

Pro Thr His Leu Ala Ile Leu Ser Gln Pro Pro Asp Thr Ile His Gly
                645                 650                 655

Ser Leu Arg Val Thr Val Gln Gly Glu Val Ile Glu Gln Ser Phe Gly
            660                 665                 670

Glu Glu His Leu Cys Phe Arg Thr Leu Gln Arg Tyr Thr Ala Ala Thr
        675                 680                 685

Leu Glu His Ser Met Cys Pro Pro Ala Ser Pro Glu Pro Glu Trp Arg
        690                 695                 700

Glu Leu Leu Asp Glu Met Ala Val Ala Ala Thr Lys Glu Tyr Arg Ser
705                 710                 715                 720

Ile Val Phe His Glu Pro Arg Phe Val Glu Tyr Phe Arg Leu Ala Thr
                725                 730                 735

Pro Glu Leu Glu Tyr Gly Arg Met Asn Ile Gly Ser Arg Pro Ser Lys
            740                 745                 750

Arg Lys Pro Ser Gly Gly Ile Glu Ser Leu Arg Ala Ile Pro Trp Ile
        755                 760                 765

Phe Ala Trp Thr Gln Thr Arg Phe His Leu Pro Val Trp Leu Gly Phe
        770                 775                 780

Gly Ala Ala Phe Lys His Val Ile Asp Lys Asp Ile Lys Asn Leu Leu
785                 790                 795                 800
```

```
Met Leu Gln Glu Met Tyr Thr Arg Trp Pro Phe Phe Arg Val Thr Ile
                805                 810                 815

Asp Leu Val Glu Met Val Phe Ala Lys Gly Asp Pro Gly Ile Ala Ala
            820                 825                 830

Leu Tyr Asp Lys Leu Leu Val Ser Glu Asp Leu Trp Pro Phe Gly Glu
            835                 840                 845

Gln Leu Arg Asn Asn Tyr Asn Glu Thr Lys Asn Leu Leu Leu Gln Val
        850                 855                 860

Ala Gly His Lys Asp Leu Glu Gly Asn Pro Tyr Leu Arg Gln Arg
865                 870                 875                 880

Leu Arg Leu Arg Asp Ser Tyr Ile Thr Thr Leu Asn Ala Cys Gln Ala
                885                 890                 895

Tyr Thr Leu Lys Arg Ile Arg Asp Pro Asn Tyr His Val Thr Val Arg
            900                 905                 910

Pro Arg Leu Ser Lys Glu Ile Met Glu Ser Asn Lys Ala Ala Ala Glu
            915                 920                 925

Leu Val Lys Leu Asn Pro Thr Ser Glu Tyr Ala Pro Gly Leu Glu Asp
            930                 935                 940

Thr Leu Ile Leu Thr Met Lys Gly Ile Ala Ala Gly Met Gln Asn Thr
945                 950                 955                 960

Gly

<210> SEQ ID NO 5
<211> LENGTH: 961
<212> TYPE: PRT
<213> ORGANISM: Kalanchoe laxiflora

<400> SEQUENCE: 5

Met Lys Leu Glu Lys Met Ala Ser Ile Asp Ala His Leu Arg Leu Leu
1               5                   10                  15

Ala Pro Gly Lys Val Ser Glu Asp Lys Leu Val Glu Tyr Asp Ala
            20                  25                  30

Leu Leu Leu Asp Arg Phe Leu Asp Ile Leu Gln Ala Leu His Gly Glu
            35                  40                  45

Asp Leu Lys Glu Thr Val Gln Glu Cys Tyr Glu Met Ser Ala Glu Tyr
        50                  55                  60

Glu Ser Ser His Asp Pro Glu Lys Leu Glu Glu Leu Gly Ser Val Leu
65                  70                  75                  80

Thr Ser Leu Asp Ala Gly Asp Ser Ile Val Val Ala Lys Ser Phe Ser
                85                  90                  95

His Met Leu Asn Leu Ala Asn Leu Ala Glu Glu Val Gln Ile Ala Tyr
            100                 105                 110

Arg Arg Arg Ile Lys Leu Lys Lys Gly Asp Phe Ala Asp Glu Ala Ser
            115                 120                 125

Ala Thr Thr Glu Ser Asp Ile Glu Glu Thr Ile Arg Lys Leu Val Lys
        130                 135                 140

Met Gly Lys Ser Asn Glu Glu Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Thr Gln Leu Tyr
            180                 185                 190

Ala Lys Asp Ile Thr Thr Asp Asp Lys Lys Glu Leu Asp Glu Ala Leu
            195                 200                 205
```

-continued

```
Gln Arg Glu Ile Gln Ala Ala Phe Arg Thr Asp Glu Ile Arg Arg Thr
    210                 215                 220
Pro Pro Thr Pro Gln Asp Glu Met Arg Ala Gly Met Ser Tyr Phe His
225                 230                 235                 240
Glu Thr Ile Trp Lys Gly Val Pro Lys Phe Leu Arg Arg Val Asp Thr
                245                 250                 255
Ala Leu Lys Asn Val Gly Ile Thr Glu Arg Val Pro Tyr Asn Ala Pro
            260                 265                 270
Leu Ile Gln Phe Ser Ser Trp Met Gly Gly Asp Arg Asp Gly Asn Pro
        275                 280                 285
Arg Val Thr Pro Glu Val Thr Arg Asp Val Cys Leu Leu Ala Arg Met
    290                 295                 300
Met Ala Ala Asn Leu Tyr Phe Ser Gln Ile Glu Asp Leu Met Phe Glu
305                 310                 315                 320
Leu Ser Met Trp Arg Cys Asn Asp Glu Leu Arg Ala Arg Ala Asp Glu
                325                 330                 335
Leu His Arg Thr Ser Lys Arg Asp Ser Lys His Tyr Ile Glu Phe Trp
            340                 345                 350
Lys Gln Val Pro Pro Asn Glu Pro Tyr Arg Val Val Leu Ser Asp Val
        355                 360                 365
Arg Asp Lys Leu Tyr Tyr Thr Arg Glu His Ser Arg Gln Leu Leu Ser
    370                 375                 380
Asn Gly Val Ser Asp Val Pro Glu Val Leu Thr Phe Thr Asp Val Asp
385                 390                 395                 400
Gln Phe Leu Glu Pro Leu Glu Leu Cys Tyr Arg Ser Leu Cys Ala Cys
                405                 410                 415
Gly Asp Arg Pro Ile Ala Asp Gly Ser Leu Leu Asp Phe Leu Arg Gln
            420                 425                 430
Val Ser Thr Phe Gly Leu Ser Leu Val Arg Leu Asp Ile Arg Gln Glu
        435                 440                 445
Ser Glu Arg His Thr Asp Val Met Asp Ala Ile Thr Asn His Leu Gly
    450                 455                 460
Ile Gly Ser Tyr Arg Glu Trp Ser Glu Glu Lys Arg Gln Asp Trp Leu
465                 470                 475                 480
Leu Ser Glu Leu Lys Gly Lys Arg Pro Leu Phe Gly Pro Asp Leu Pro
                485                 490                 495
Lys Thr Glu Glu Ile Ala Asp Val Leu Gly Thr Phe Asp Val Ile Ala
            500                 505                 510
Glu Leu Pro Ala Asp Asn Phe Gly Ala Tyr Ile Ile Ser Met Ala Thr
        515                 520                 525
Ser Pro Ser Asp Val Leu Ala Val Glu Leu Leu Gln Arg Glu Cys Arg
    530                 535                 540
Val Lys His Pro Leu Arg Val Val Pro Leu Phe Glu Lys Leu Ala Asp
545                 550                 555                 560
Leu Glu Ala Ala Pro Ala Ala Val Ala Arg Leu Phe Ser Ile Asp Trp
                565                 570                 575
Tyr Lys Asn Arg Ile Asp Gly Lys Gln Glu Val Met Ile Gly Tyr Ser
            580                 585                 590
Asp Ser Gly Lys Asp Ala Gly Arg Leu Ser Ala Ala Trp Gln Leu Tyr
        595                 600                 605
Lys Ala Gln Glu Asp Leu Val Lys Val Ala Lys Glu Phe Gly Val Lys
    610                 615                 620
Leu Thr Met Phe His Gly Arg Gly Gly Thr Val Gly Arg Gly Gly Gly
```

Pro Ala His Leu Ala Ile Leu Ser Gln Pro Asp Thr Ile Leu Gly
            645                 650                 655

Ser Leu Arg Val Thr Val Gln Gly Glu Val Ile Glu Gln Ser Phe Gly
        660                 665                 670

Glu Glu His Leu Cys Phe Arg Thr Leu Gln Arg Tyr Thr Ala Ala Thr
    675                 680                 685

Leu Glu His Ser Met Cys Pro Ala Ser Pro Glu Pro Glu Trp Arg
690                 695                 700

Glu Leu Asp Glu Met Ala Val Thr Ala Thr Lys Glu Tyr Arg Ser
705                 710                 715                 720

Val Val Phe Gln Glu Pro Arg Phe Val Glu Tyr Phe Arg Leu Ala Thr
                725                 730                 735

Pro Glu Leu Glu Tyr Gly Arg Met Asn Ile Gly Ser Arg Pro Ser Lys
            740                 745                 750

Arg Lys Pro Asn Gly Gly Ile Glu Ser Leu Arg Ala Ile Pro Trp Ile
        755                 760                 765

Phe Ala Trp Thr Gln Thr Arg Phe His Leu Pro Val Trp Leu Gly Phe
    770                 775                 780

Gly Ala Ala Phe Lys Gln Val Ile His Lys Asp Ile Lys Asn Leu Leu
785                 790                 795                 800

Thr Leu Gln Asp Met Tyr Lys Arg Trp Pro Phe Phe Arg Val Thr Ile
                805                 810                 815

Asp Leu Val Glu Met Val Phe Ala Lys Gly Asp Pro Gly Ile Ala Ala
            820                 825                 830

Leu Tyr Asp Lys Leu Leu Val Ser Glu Asp Leu Trp Pro Phe Gly Glu
        835                 840                 845

Gln Leu Arg Asn Asn Tyr Asn Glu Thr Lys Asn Leu Leu Gln Val
    850                 855                 860

Ala Gly His Lys Asp Leu Leu Glu Gly Asp Pro Tyr Leu Arg Gln Arg
865                 870                 875                 880

Leu Arg Leu Arg Asp Ser Tyr Ile Thr Thr Leu Asn Val Cys Gln Val
                885                 890                 895

Tyr Thr Leu Lys Arg Ile Arg Asp Pro His Tyr His Val Thr Val Arg
            900                 905                 910

Pro His Leu Ser Lys Glu Ile Thr Glu Ser Asn Lys Pro Ala Ala Glu
        915                 920                 925

Leu Val Lys Leu Asn Pro Thr Ser Glu Tyr Ala Pro Gly Leu Glu Asp
    930                 935                 940

Thr Leu Ile Leu Thr Met Lys Gly Ile Ala Ala Gly Met Gln Asn Thr
945                 950                 955                 960

Gly

<210> SEQ ID NO 6
<211> LENGTH: 961
<212> TYPE: PRT
<213> ORGANISM: Kalanchoe laxiflora

<400> SEQUENCE: 6

Met Lys Leu Glu Lys Met Ala Ser Ile Asp Ala His Leu Arg Leu Leu
1               5                   10                  15

Ala Pro Gly Lys Val Ser Glu Asp Asp Lys Leu Val Glu Tyr Asp Ala
            20                  25                  30

Leu Leu Leu Asp Arg Phe Leu Asp Ile Leu Gln Ala Leu His Gly Glu

```
                  35                  40                  45
Asp Leu Lys Glu Thr Val Gln Glu Cys Tyr Glu Met Ser Ala Glu Tyr
 50                  55                  60

Glu Ser Ser His Asp Pro Glu Lys Leu Glu Glu Leu Gly Ser Val Leu
 65                  70                  75                  80

Thr Ser Leu Asp Ala Gly Asp Ser Ile Val Val Ala Lys Ser Phe Ser
                 85                  90                  95

His Met Leu Asn Leu Ala Asn Leu Ala Glu Glu Val Gln Ile Ala Tyr
                100                 105                 110

Arg Arg Arg Ile Lys Leu Lys Lys Gly Asp Phe Ala Asp Glu Ala Ser
            115                 120                 125

Ala Thr Thr Glu Ser Asp Ile Glu Glu Thr Ile Arg Lys Leu Val Lys
            130                 135                 140

Met Gly Lys Ser Asn Glu Glu Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Thr Gln Leu Tyr
            180                 185                 190

Ala Lys Asp Ile Thr Thr Asp Lys Lys Glu Leu Asp Glu Ala Leu
            195                 200                 205

Gln Arg Glu Ile Gln Ala Ala Phe Arg Thr Asp Glu Ile Arg Arg Thr
210                 215                 220

Pro Pro Thr Pro Gln Asp Glu Met Arg Ala Gly Met Ser Tyr Phe His
225                 230                 235                 240

Glu Thr Ile Trp Lys Gly Val Pro Lys Phe Leu Arg Arg Val Asp Thr
                245                 250                 255

Ala Leu Lys Asn Val Gly Ile Thr Glu Arg Val Pro Tyr Asn Ala Pro
            260                 265                 270

Leu Ile Gln Phe Ser Ser Trp Met Gly Gly Asp Arg Asp Gly Asn Pro
            275                 280                 285

Arg Val Thr Pro Glu Val Thr Arg Asp Val Cys Leu Leu Ala Arg Met
290                 295                 300

Met Ala Ala Asn Leu Tyr Phe Ser Gln Ile Glu Asp Leu Met Phe Glu
305                 310                 315                 320

Leu Ser Met Trp Arg Cys Asn Asp Glu Leu Arg Ala Arg Ala Asp Glu
                325                 330                 335

Leu His Arg Thr Ser Lys Arg Asp Ser Lys His Tyr Ile Glu Phe Trp
            340                 345                 350

Lys Gln Val Pro Pro Asn Glu Pro Tyr Arg Val Val Leu Ser Asp Val
            355                 360                 365

Arg Asp Lys Leu Tyr Tyr Thr Arg Glu His Ser Arg Gln Leu Leu Ser
370                 375                 380

Asn Gly Val Ser Asp Val Pro Glu Val Leu Thr Phe Thr Asp Val Asp
385                 390                 395                 400

Gln Phe Leu Glu Pro Leu Glu Leu Cys Tyr Arg Ser Leu Cys Ala Cys
                405                 410                 415

Gly Asp Arg Pro Ile Ala Asp Gly Ser Leu Leu Asp Phe Leu Arg Gln
            420                 425                 430

Val Ser Thr Phe Gly Leu Ser Leu Val Arg Leu Asp Ile Arg Gln Glu
            435                 440                 445

Ser Glu Arg His Thr Asp Val Met Asp Ala Ile Thr Asn His Leu Gly
450                 455                 460
```

```
Ile Gly Ser Tyr Arg Glu Trp Ser Glu Glu Lys Arg Gln Asp Trp Leu
465                 470                 475                 480

Leu Ser Glu Leu Lys Gly Lys Arg Pro Leu Phe Gly Pro Asp Leu Pro
            485                 490                 495

Lys Thr Glu Glu Ile Ala Asp Val Leu Gly Thr Phe Asp Val Ile Ala
                500                 505                 510

Glu Leu Pro Ala Asp Asn Phe Gly Ala Tyr Ile Ile Ser Met Ala Thr
            515                 520                 525

Ser Pro Ser Asp Val Leu Ala Val Glu Leu Leu Gln Arg Glu Cys Arg
    530                 535                 540

Val Lys His Pro Leu Arg Val Val Pro Leu Phe Glu Lys Leu Ala Asp
545                 550                 555                 560

Leu Glu Ala Ala Pro Ala Ala Val Ala Arg Leu Phe Ser Ile Asp Trp
                565                 570                 575

Tyr Lys Asn Arg Ile Asp Gly Lys Gln Glu Val Met Ile Gly Tyr Ser
            580                 585                 590

Asp Ser Gly Lys Asp Ala Gly Arg Leu Ser Ala Ala Trp Gln Leu Tyr
    595                 600                 605

Lys Ala Gln Glu Asp Leu Val Lys Val Ala Lys Glu Phe Gly Val Lys
610                 615                 620

Leu Thr Met Phe His Gly Arg Gly Gly Thr Val Gly Arg Gly Gly Gly
625                 630                 635                 640

Pro Ala His Leu Ala Ile Leu Ser Gln Pro Pro Asp Thr Ile Leu Gly
                645                 650                 655

Ser Leu Arg Val Thr Val Gln Gly Glu Val Ile Glu Gln Ser Phe Gly
            660                 665                 670

Glu Glu His Leu Cys Phe Arg Thr Leu Gln Arg Tyr Thr Ala Ala Thr
    675                 680                 685

Leu Glu His Ser Met Cys Pro Pro Ala Ser Pro Glu Pro Glu Trp Arg
    690                 695                 700

Ala Leu Leu Asp Glu Met Ala Val Thr Ala Thr Lys Glu Tyr Arg Ser
705                 710                 715                 720

Val Val Phe Gln Glu Pro Arg Phe Val Glu Tyr Phe Arg Leu Ala Thr
                725                 730                 735

Pro Glu Leu Glu Tyr Gly Arg Met Asn Ile Gly Ser Arg Pro Ser Lys
            740                 745                 750

Arg Lys Pro Asn Gly Gly Ile Glu Ser Leu Arg Ala Ile Pro Trp Ile
    755                 760                 765

Phe Ala Trp Thr Gln Thr Arg Phe His Leu Pro Val Trp Leu Gly Phe
    770                 775                 780

Gly Ala Ala Phe Lys His Val Ile Asp Lys Asp Ile Lys Asn Leu Leu
785                 790                 795                 800

Thr Leu Gln Glu Met Tyr Lys Arg Trp Pro Phe Phe Arg Val Thr Ile
                805                 810                 815

Asp Leu Val Glu Met Val Phe Ala Lys Gly Asp Pro Gly Ile Ala Ala
            820                 825                 830

Leu Tyr Asp Lys Leu Leu Val Ser Glu Asp Leu Trp Pro Phe Gly Glu
    835                 840                 845

Gln Leu Arg Asn Asn Tyr Asn Glu Thr Lys Asn Leu Leu Leu Gln Val
    850                 855                 860

Ala Gly His Lys Asp Leu Leu Glu Gly Asp Pro Tyr Leu Arg Gln Arg
865                 870                 875                 880
```

-continued

Leu Arg Leu Arg Asp Ser Tyr Ile Thr Thr Leu Asn Val Cys Gln Ala
                885                 890                 895

Tyr Thr Leu Lys Arg Ile Arg Asp Pro His Tyr His Val Thr Val Arg
            900                 905                 910

Pro His Leu Ser Lys Glu Ile Thr Glu Ser Asn Lys Pro Ala Ala Glu
            915                 920                 925

Leu Val Lys Leu Asn Pro Thr Ser Glu Tyr Ala Pro Gly Leu Glu Asp
            930                 935                 940

Thr Leu Ile Leu Thr Met Lys Gly Ile Ala Ala Gly Met Gln Asn Thr
945                 950                 955                 960

Gly

<210> SEQ ID NO 7
<211> LENGTH: 961
<212> TYPE: PRT
<213> ORGANISM: Kalanchoe laxiflora

<400> SEQUENCE: 7

Met Lys Leu Glu Lys Met Ala Ser Ile Asp Ala His Leu Arg Leu Leu
1               5                   10                  15

Ala Pro Gly Lys Val Ser Glu Asp Lys Leu Val Glu Tyr Asp Ala
            20                  25                  30

Leu Leu Leu Asp Arg Phe Leu Asp Ile Leu Gln Ala Leu His Gly Glu
        35                  40                  45

Asp Leu Lys Glu Thr Val Gln Glu Cys Tyr Glu Leu Ser Ala Glu Tyr
    50                  55                  60

Glu Ser Ser Arg Asp Pro Glu Lys Leu Glu Leu Gly Ser Val Leu
65                  70                  75                  80

Thr Ser Leu Asp Ala Gly Asp Ser Ile Val Leu Ala Lys Ser Phe Ser
                85                  90                  95

His Met Leu Asn Leu Ala Asn Leu Ala Glu Glu Val Gln Ile Ala Tyr
            100                 105                 110

Arg Arg Arg Ile Lys Leu Lys Lys Gly Asp Phe Ala Asp Glu Ala Ser
        115                 120                 125

Ala Thr Thr Glu Ser Asp Ile Glu Glu Thr Ile Arg Lys Leu Val Lys
    130                 135                 140

Met Gly Lys Thr Ser Glu Gln Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Thr Gln Leu Tyr
            180                 185                 190

Ala Lys Asp Ile Thr Thr Asp Lys Lys Glu Leu Asp Glu Ala Leu
        195                 200                 205

Gln Arg Glu Ile Gln Ala Ala Phe Arg Thr Asp Glu Ile Arg Arg Thr
    210                 215                 220

Pro Pro Thr Pro Gln Asp Glu Met Arg Ala Gly Met Ser Tyr Phe His
225                 230                 235                 240

Glu Thr Ile Trp Lys Gly Val Pro Lys Phe Leu Arg Arg Val Asp Thr
                245                 250                 255

Ala Leu Lys Asn Val Gly Ile Asn Glu Arg Val Pro Tyr Asn Ala Pro
            260                 265                 270

Leu Ile Gln Phe Ser Ser Trp Met Gly Gly Asp Arg Asp Gly Asn Pro
        275                 280                 285

-continued

```
Arg Val Thr Pro Glu Val Thr Arg Asp Val Cys Leu Leu Ala Arg Met
290             295                 300

Met Val Ala Asn Met Tyr Phe Ser Gln Ile Glu Asp Leu Met Phe Glu
305                 310                 315                 320

Leu Ser Met Trp Arg Cys Asn Asp Glu Leu Arg Ala Arg Ala Asp Glu
            325                 330                 335

Leu His Met Thr Ala Lys Arg Asp Ser Lys Gln Tyr Ile Glu Phe Trp
                340                 345                 350

Lys Gln Val Pro Pro Ser Glu Pro Tyr Arg Leu Val Leu Ser Asp Val
            355                 360                 365

Arg Asp Lys Leu Tyr His Thr Arg Glu His Ser Arg Gln Leu Leu Ser
370                 375                 380

Asn Gly Val Ser Asp Val Pro Glu Glu Leu Ile Phe Thr Asp Val Asp
385                 390                 395                 400

Gln Phe Leu Glu Pro Leu Glu Leu Cys Tyr Arg Ser Leu Cys Ala Cys
                405                 410                 415

Gly Asp Arg Pro Ile Ala Asp Gly Ser Leu Leu Asp Phe Leu Arg Gln
            420                 425                 430

Val Ser Thr Phe Gly Leu Ser Leu Val Arg Leu Asp Ile Arg Gln Glu
            435                 440                 445

Ser Glu Arg His Thr Asp Val Met Asp Ala Ile Thr Asn His Leu Gly
450                 455                 460

Ile Gly Ser Tyr Arg Lys Trp Ser Glu Lys Arg Gln Asp Trp Leu
465                 470                 475                 480

Leu Ser Glu Leu Lys Gly Lys Arg Pro Leu Phe Gly Pro Asp Leu Pro
                485                 490                 495

Lys Thr Glu Glu Ile Ala Asp Val Leu Gly Thr Phe Asp Val Ile Ala
            500                 505                 510

Glu Leu Pro Ser Asp Asn Phe Gly Ala Tyr Ile Ile Ser Met Ala Thr
            515                 520                 525

Ser Pro Ser Asp Val Leu Ala Val Glu Leu Leu Gln Arg Glu Ser His
530                 535                 540

Val Lys His Pro Leu Arg Val Val Pro Leu Phe Glu Lys Leu Ala Asp
545                 550                 555                 560

Leu Glu Thr Ala Pro Ala Ala Val Ala Arg Leu Phe Ser Ile Asp Trp
                565                 570                 575

Tyr Lys Asn Arg Ile Asp Gly Lys Gln Glu Val Met Ile Gly Tyr Ser
            580                 585                 590

Asp Ser Gly Lys Asp Ala Gly Arg Leu Ser Ala Ala Trp Gln Leu Tyr
            595                 600                 605

Lys Ala Gln Glu Asp Leu Val Lys Val Ala Lys Glu Phe Gly Val Lys
610                 615                 620

Leu Thr Met Phe His Gly Arg Gly Gly Thr Val Gly Arg Gly Gly
625                 630                 635                 640

Pro Thr His Leu Ala Ile Leu Ser Gln Pro Pro Asp Thr Ile His Gly
                645                 650                 655

Ser Leu Arg Val Thr Val Gln Gly Glu Val Ile Glu Gln Ser Phe Gly
            660                 665                 670

Glu Glu His Leu Cys Phe Arg Thr Leu Gln Arg Tyr Thr Ala Ala Thr
            675                 680                 685

Leu Glu His Ser Met Cys Pro Pro Ala Ser Pro Glu Pro Glu Trp Arg
690                 695                 700

Glu Leu Leu Asp Glu Met Ala Val Ala Ala Thr Lys Glu Tyr Arg Ser
```

```
            705                 710                 715                 720
Ile Val Phe His Glu Pro Arg Phe Val Glu Tyr Phe Arg Leu Ala Thr
                    725                 730                 735

Pro Glu Leu Glu Tyr Gly Arg Met Asn Ile Gly Ser Arg Pro Ser Lys
            740                 745                 750

Arg Lys Pro Ser Gly Gly Ile Glu Ser Leu Arg Ala Ile Pro Trp Ile
                755                 760                 765

Phe Ala Trp Thr Gln Thr Arg Phe His Leu Pro Val Trp Leu Gly Phe
770                 775                 780

Gly Ala Ala Phe Lys His Val Ile Asp Lys Asp Ile Lys Asn Leu Leu
785                 790                 795                 800

Met Leu Gln Glu Met Tyr Thr Arg Trp Pro Phe Arg Val Thr Ile
                805                 810                 815

Asp Leu Val Glu Met Val Phe Ala Lys Gly Asp Pro Gly Ile Ala Ala
                820                 825                 830

Leu Tyr Asp Lys Leu Leu Val Ser Glu Asp Leu Trp Pro Phe Gly Glu
                835                 840                 845

Gln Leu Arg Asn Asn Tyr Asn Glu Thr Lys Asn Leu Leu Leu Gln Val
            850                 855                 860

Ala Gly His Lys Asp Leu Leu Glu Gly Asn Pro Tyr Leu Arg Gln Arg
865                 870                 875                 880

Leu Arg Leu Arg Asp Ser Tyr Ile Thr Thr Leu Asn Ala Cys Gln Ala
                885                 890                 895

Tyr Thr Leu Lys Arg Ile Arg Asp Pro Asn Tyr His Val Thr Val Arg
                900                 905                 910

Pro Arg Leu Ser Lys Glu Ile Met Glu Ser Asn Lys Ala Ala Ala Glu
            915                 920                 925

Leu Val Lys Leu Asn Pro Thr Ser Glu Tyr Ala Pro Gly Leu Glu Asp
            930                 935                 940

Thr Leu Ile Leu Thr Met Lys Gly Ile Ala Ala Gly Met Gln Asn Thr
945                 950                 955                 960

Gly

<210> SEQ ID NO 8
<211> LENGTH: 961
<212> TYPE: PRT
<213> ORGANISM: Kalanchoe laxiflora

<400> SEQUENCE: 8

Met Lys Leu Glu Lys Met Ala Ser Ile Asp Ala His Leu Arg Leu Leu
1               5                   10                  15

Ala Pro Gly Lys Val Ser Glu Asp Lys Leu Val Glu Tyr Asp Ala
            20                  25                  30

Leu Leu Leu Asp Arg Phe Leu Asp Ile Leu Gln Ala Leu His Gly Glu
        35                  40                  45

Asp Leu Lys Glu Thr Val Gln Glu Cys Tyr Glu Leu Ser Ala Glu Tyr
    50                  55                  60

Glu Ser Ser Arg Asp Pro Glu Lys Leu Glu Glu Leu Gly Ser Val Leu
65                  70                  75                  80

Thr Ser Leu Asp Ala Gly Asp Ser Ile Val Leu Ala Lys Ser Phe Ser
                85                  90                  95

His Met Leu Asn Leu Ala Asn Leu Ala Glu Glu Val Gln Ile Ala Tyr
            100                 105                 110

Arg Arg Arg Ile Lys Leu Lys Lys Gly Asp Phe Ala Asp Glu Ala Ser
```

```
            115                 120                 125
Ala Thr Thr Glu Ser Asp Ile Glu Glu Thr Ile Arg Lys Leu Val Lys
    130                 135                 140

Met Gly Lys Thr Ser Glu Gln Val Phe Asp Ala Leu Lys Asn Gln Thr
145                 150                 155                 160

Val Asp Leu Val Phe Thr Ala His Pro Thr Gln Ser Val Arg Arg Ser
                165                 170                 175

Leu Leu Gln Lys His Gly Arg Ile Arg Asn Cys Leu Thr Gln Leu Tyr
            180                 185                 190

Ala Lys Asp Ile Thr Thr Asp Lys Lys Glu Leu Asp Glu Ala Leu
        195                 200                 205

Gln Arg Glu Ile Gln Ala Ala Phe Arg Thr Asp Glu Ile Arg Arg Thr
    210                 215                 220

Pro Pro Thr Pro Gln Asp Glu Met Arg Ala Gly Met Ser Tyr Phe His
225                 230                 235                 240

Glu Thr Ile Trp Lys Gly Val Pro Lys Phe Leu Arg Arg Val Asp Thr
                245                 250                 255

Ala Leu Lys Asn Val Gly Ile Asn Glu Arg Val Pro Tyr Asn Ala Pro
            260                 265                 270

Leu Ile Gln Phe Ser Ser Trp Met Gly Gly Asp Arg Asp Gly Asn Pro
        275                 280                 285

Arg Val Thr Pro Glu Val Thr Arg Asp Val Cys Leu Leu Ala Arg Met
    290                 295                 300

Met Val Ala Asn Met Tyr Phe Ser Gln Ile Glu Asp Leu Met Phe Glu
305                 310                 315                 320

Leu Ser Met Trp Arg Cys Asn Asp Glu Leu Arg Ala Arg Ala Asp Glu
                325                 330                 335

Leu His Met Thr Ala Lys Arg Asp Ser Lys Gln Tyr Ile Glu Phe Trp
            340                 345                 350

Lys Gln Val Pro Pro Ser Glu Pro Tyr Arg Leu Val Leu Ser Asp Val
        355                 360                 365

Arg Asp Lys Leu Tyr His Thr Arg Glu His Ser Arg Gln Leu Leu Ser
    370                 375                 380

Asn Gly Val Ser Asp Val Pro Glu Glu Leu Ile Phe Thr Asp Val Asp
385                 390                 395                 400

Gln Phe Leu Glu Pro Leu Glu Leu Cys Tyr Arg Ser Leu Cys Ala Cys
                405                 410                 415

Gly Asp Arg Pro Ile Ala Asp Gly Ser Leu Leu Asp Phe Leu Arg Gln
            420                 425                 430

Val Ser Thr Phe Gly Leu Ser Leu Val Arg Leu Asp Ile Arg Gln Glu
        435                 440                 445

Ser Glu Arg His Thr Asp Val Met Asp Ala Ile Thr Asn His Leu Gly
    450                 455                 460

Ile Gly Ser Tyr Arg Glu Trp Ser Glu Glu Lys Arg Gln Asp Trp Leu
465                 470                 475                 480

Leu Ser Glu Leu Lys Gly Lys Arg Pro Leu Phe Gly Pro Asp Leu Pro
                485                 490                 495

Lys Thr Glu Glu Ile Ala Asp Val Leu Gly Thr Phe Asp Val Ile Ala
            500                 505                 510

Glu Leu Pro Ser Asp Asn Phe Gly Ala Tyr Ile Ile Ser Met Ala Thr
        515                 520                 525

Ser Pro Ser Asp Val Leu Ala Val Glu Leu Leu Gln Arg Glu Ser His
    530                 535                 540
```

```
Val Lys His Pro Leu Arg Val Pro Leu Phe Glu Lys Leu Ala Asp
545                 550                 555                 560

Leu Glu Ala Ala Pro Ala Val Ala Arg Leu Phe Ser Ile Asp Trp
                565                 570                 575

Tyr Lys Asn Arg Ile Asp Gly Lys Gln Glu Val Met Ile Gly Tyr Ser
            580                 585                 590

Asp Ser Gly Lys Asp Ala Gly Arg Leu Ser Ala Ala Trp Gln Leu Tyr
        595                 600                 605

Lys Ala Gln Glu Asp Leu Val Lys Val Ala Lys Glu Phe Gly Val Lys
        610                 615                 620

Leu Thr Met Phe His Gly Arg Gly Thr Val Gly Arg Gly Gly Gly
625                 630                 635                 640

Pro Thr His Leu Ala Ile Leu Ser Gln Pro Pro Asp Thr Ile His Gly
                645                 650                 655

Ser Leu Arg Val Thr Val Gln Gly Glu Val Ile Glu Gln Ser Phe Gly
            660                 665                 670

Glu Glu His Leu Cys Phe Arg Thr Leu Gln Arg Tyr Thr Ala Ala Thr
        675                 680                 685

Leu Glu His Ser Met Cys Pro Ala Ser Pro Glu Pro Glu Trp Arg
690                 695                 700

Glu Leu Leu Asp Glu Met Ala Val Ala Ala Thr Lys Glu Tyr Arg Ser
705                 710                 715                 720

Ile Val Phe His Glu Pro Arg Phe Val Glu Tyr Phe Arg Leu Ala Thr
            725                 730                 735

Pro Glu Leu Glu Tyr Gly Arg Met Asn Ile Gly Ser Arg Pro Ser Lys
            740                 745                 750

Arg Lys Pro Ser Gly Gly Ile Glu Ser Leu Arg Ala Ile Pro Trp Ile
        755                 760                 765

Phe Ala Trp Thr Gln Thr Arg Phe His Leu Pro Val Trp Leu Gly Phe
        770                 775                 780

Gly Ala Ala Phe Lys His Val Ile Asp Lys Asp Ile Lys Asn Leu Leu
785                 790                 795                 800

Met Leu Gln Glu Met Tyr Thr Arg Trp Pro Phe Phe Arg Val Thr Ile
                805                 810                 815

Asp Leu Val Glu Met Val Phe Ala Lys Gly Asp Pro Gly Ile Ala Ala
            820                 825                 830

Leu Tyr Asp Lys Leu Leu Val Ser Glu Asp Leu Trp Pro Phe Gly Glu
        835                 840                 845

Gln Leu Arg Asn Asn Tyr Asn Glu Thr Lys Asn Leu Leu Leu Lys Val
        850                 855                 860

Ala Gly His Lys Asp Leu Leu Glu Gly Asn Pro Tyr Leu Arg Gln Arg
865                 870                 875                 880

Leu Arg Leu Arg Asp Ser Tyr Ile Thr Thr Leu Asn Ala Cys Gln Ala
                885                 890                 895

Tyr Thr Leu Lys Arg Ile Arg Asp Pro Asn Tyr His Val Thr Val Arg
            900                 905                 910

Pro Arg Leu Ser Lys Glu Ile Met Glu Ser Asn Lys Ala Ala Ala Glu
        915                 920                 925

Leu Val Lys Leu Asn Pro Thr Ser Glu Tyr Ala Pro Gly Leu Glu Asp
        930                 935                 940

Thr Leu Ile Leu Thr Met Lys Gly Ile Ala Ala Gly Met Gln Asn Thr
945                 950                 955                 960
```

Gly

<210> SEQ ID NO 9
<211> LENGTH: 967
<212> TYPE: PRT
<213> ORGANISM: Zea mays

<400> SEQUENCE: 9

```
Met Ala Ala Leu Gly Ala Lys Met Glu Arg Leu Ser Ser Ile Asp Ala
1               5                   10                  15

Gln Leu Arg Met Leu Val Pro Gly Lys Val Ser Glu Asp Asp Lys Leu
            20                  25                  30

Ile Glu Tyr Asp Ala Leu Leu Leu Asp Arg Phe Leu Asp Ile Leu Gln
        35                  40                  45

Asp Leu His Gly Asp Asp Leu Lys Glu Met Val Gln Glu Cys Tyr Glu
    50                  55                  60

Val Ala Ala Glu Tyr Glu Thr Lys His Asp Leu Gln Lys Leu Asp Glu
65                  70                  75                  80

Leu Gly Lys Met Ile Thr Ser Leu Asp Pro Gly Asp Ser Ile Val Ile
                85                  90                  95

Ala Lys Ser Phe Ser His Met Leu Asn Leu Ala Asn Leu Ala Glu Glu
            100                 105                 110

Val Gln Ile Ala Tyr Arg Arg Ile Lys Leu Lys Lys Gly Asp Phe
        115                 120                 125

Ala Asp Glu Asn Ser Ala Ile Thr Glu Ser Asp Ile Glu Glu Thr Leu
    130                 135                 140

Lys Arg Leu Val Val Asp Leu Lys Lys Ser Pro Ala Glu Val Phe Asp
145                 150                 155                 160

Ala Leu Lys Ser Gln Thr Val Asp Leu Val Leu Thr Ala His Pro Thr
                165                 170                 175

Gln Ser Val Arg Arg Ser Leu Leu Gln Lys His Ser Arg Ile Arg Asn
            180                 185                 190

Cys Leu Val Gln Leu Tyr Ser Lys Asp Ile Thr Pro Asp Asp Lys Gln
        195                 200                 205

Glu Leu Asp Glu Ala Leu Gln Arg Glu Ile Gln Ala Ala Phe Arg Thr
    210                 215                 220

Asp Glu Ile Arg Arg Thr Gln Pro Thr Pro Gln Asp Glu Met Arg Ala
225                 230                 235                 240

Gly Met Ser Tyr Phe His Glu Thr Ile Trp Lys Gly Val Pro Lys Phe
                245                 250                 255

Leu Arg Arg Val Asp Thr Ala Leu Lys Asn Ile Gly Ile Asn Glu Arg
            260                 265                 270

Val Pro Tyr Asn Ala Pro Leu Ile Gln Phe Ser Ser Trp Met Gly Gly
        275                 280                 285

Asp Arg Asp Gly Asn Pro Arg Val Thr Pro Glu Val Thr Arg Asp Val
    290                 295                 300

Cys Leu Leu Ala Arg Met Met Ala Ser Asn Leu Tyr Cys Ser Gln Ile
305                 310                 315                 320

Glu Asp Leu Met Phe Glu Leu Ser Met Trp Arg Cys Ser Asp Glu Leu
                325                 330                 335

Arg Met Arg Ala Asp Val Leu His Leu Ser Thr Lys Lys Asp Ala Lys
            340                 345                 350

His Tyr Ile Glu Phe Trp Lys Lys Val Pro Pro Asn Glu Pro Tyr Arg
        355                 360                 365
```

-continued

```
Val Ile Leu Ser Asp Val Arg Asp Lys Leu Tyr Asn Thr Arg Glu Arg
370                 375                 380

Ser Arg Glu Leu Leu Ser Ser Gly His Ser Asp Ile Pro Glu Glu Ala
385                 390                 395                 400

Thr Leu Thr Asn Val Glu Gln Leu Leu Glu Pro Leu Glu Leu Cys Tyr
                405                 410                 415

Arg Ser Leu Cys Ala Cys Gly Asp Ser Val Ile Ala Asp Gly Thr Leu
            420                 425                 430

Leu Asp Phe Leu Arg Gln Val Ser Thr Phe Gly Leu Ser Leu Val Arg
        435                 440                 445

Leu Asp Ile Arg Gln Glu Ser Asp Arg His Thr Asp Val Leu Asp Ala
450                 455                 460

Ile Thr Thr Tyr Leu Gly Ile Gly Ser Tyr Arg Glu Trp Thr Glu Glu
465                 470                 475                 480

Arg Arg Gln Glu Trp Leu Leu Ser Glu Leu Asn Gly Lys Arg Pro Leu
                485                 490                 495

Phe Gly Ser Asp Leu Pro Lys Thr Glu Glu Ile Ala Asp Val Leu Asp
            500                 505                 510

Thr Phe His Val Ile Ala Glu Leu Pro Ser Asp Asn Phe Gly Ala Tyr
        515                 520                 525

Ile Ile Ser Met Ala Thr Ala Pro Ser Asp Val Leu Ala Val Glu Leu
530                 535                 540

Leu Gln Arg Glu Cys His Val Lys Thr Pro Leu Arg Val Val Pro Leu
545                 550                 555                 560

Phe Glu Lys Leu Ala Asp Leu Glu Ala Ala Pro Ala Ala Leu Ala Arg
                565                 570                 575

Leu Phe Ser Ile Asp Trp Tyr Arg Gln Arg Ile Asn Gly Lys Gln Glu
            580                 585                 590

Val Met Ile Gly Tyr Ser Asp Ser Gly Lys Asp Ala Gly Arg Leu Ser
        595                 600                 605

Ala Ala Trp Gln Leu Tyr Lys Ala Gln Glu Glu Leu Ile Lys Val Ala
610                 615                 620

Lys Asp Phe Gly Val Lys Leu Thr Met Phe His Gly Arg Gly Gly Thr
625                 630                 635                 640

Val Gly Arg Gly Gly Gly Pro Thr His Leu Ala Ile Leu Ser Gln Pro
                645                 650                 655

Pro Asp Thr Ile His Gly Ser Leu Arg Val Thr Val Gln Gly Glu Val
            660                 665                 670

Ile Glu Gln Ser Phe Gly Glu Glu His Leu Cys Phe Arg Thr Leu Gln
        675                 680                 685

Arg Phe Thr Ala Ala Thr Leu Glu His Gly Met His Pro Pro Asn Ala
690                 695                 700

Pro Lys Pro Glu Trp Arg Ala Leu Leu Asp Glu Met Ala Val Val Ala
705                 710                 715                 720

Thr Glu Glu Tyr Arg Ser Ile Val Phe Lys Glu Pro Arg Phe Val Glu
                725                 730                 735

Tyr Phe Arg Leu Ala Thr Pro Glu Thr Glu Tyr Gly Arg Met Asn Ile
            740                 745                 750

Gly Ser Arg Pro Ser Lys Arg Lys Pro Ser Gly Gly Ile Asp Ser Leu
        755                 760                 765

Arg Ala Ile Pro Trp Ile Phe Ala Trp Thr Gln Thr Arg Phe His Leu
770                 775                 780

Pro Val Trp Leu Gly Phe Gly Ala Ala Phe Lys His Val Leu Gln Lys
```

```
                785                 790                 795                 800
Asp Ile Arg Asn Leu His Met Leu Gln Glu Met Tyr Asn Glu Trp Pro
                    805                 810                 815

Phe Phe Arg Val Thr Ile Asp Leu Val Glu Met Val Phe Ala Lys Gly
                820                 825                 830

Asn Pro Gly Ile Ala Ala Leu Tyr Asp Lys Leu Leu Val Ser Glu Glu
                835                 840                 845

Leu His Pro Leu Gly Glu Lys Leu Arg Ala Asn Tyr Glu Glu Thr Gln
                850                 855                 860

Lys Leu Leu Leu Gln Val Ala Gly His Arg Asp Leu Leu Glu Gly Asp
865                 870                 875                 880

Leu Tyr Leu Lys Gln Arg Leu Arg Leu Arg Asp Ala Tyr Ile Thr Thr
                    885                 890                 895

Leu Asn Val Cys Gln Ala Tyr Thr Leu Lys Arg Ile Arg Asp Pro Asp
                900                 905                 910

Tyr His Val Ala Leu Arg Pro His Leu Ser Lys Glu Ile Met Asp Ser
                915                 920                 925

Thr Lys Ala Ala Ala Glu Leu Val Lys Leu Asn Pro Gly Ser Glu Tyr
930                 935                 940

Ala Pro Gly Leu Glu Asp Thr Leu Ile Leu Thr Met Lys Gly Ile Ala
945                 950                 955                 960

Ala Gly Leu Gln Asn Thr Gly
                965

<210> SEQ ID NO 10
<211> LENGTH: 966
<212> TYPE: PRT
<213> ORGANISM: Populus trichocarpa

<400> SEQUENCE: 10

Met Ala Asn Phe Arg Asn Leu Glu Lys Leu Ala Ser Ile Asp Ala Gln
1               5                   10                  15

Leu Arg Leu Leu Val Pro Gly Lys Val Ser Glu Asp Asp Lys Leu Ile
                20                  25                  30

Glu Tyr Asp Ala Leu Leu Asp Arg Phe Leu Asp Ile Leu Gln Asp
                35                  40                  45

Leu His Gly Glu Asp Leu Lys Glu Thr Val Gln Glu Cys Tyr Glu Leu
            50                  55                  60

Ser Ala Glu Tyr Glu Gly Lys His Asp Pro Lys Lys Leu Glu Glu Leu
65                  70                  75                  80

Gly Ser Val Leu Thr Ser Leu Asp Pro Gly Asp Ser Ile Val Ile Ala
                85                  90                  95

Lys Ser Phe Ser His Met Leu Asn Leu Ala Asn Leu Ala Glu Glu Val
                100                 105                 110

Gln Ile Ala Tyr Arg Arg Asn Lys Leu Lys Lys Gly Asp Phe Ala
            115                 120                 125

Asp Glu Asn Ser Ala Thr Thr Glu Ser Asp Ile Glu Glu Thr Leu Arg
130                 135                 140

Arg Leu Val Val Asp Leu Lys Lys Ser Pro Glu Glu Val Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Ala Arg Leu Arg Asn Cys
                180                 185                 190
```

-continued

Leu Ala Gln Leu Tyr Ala Lys Asp Ile Thr Pro Asn Glu Lys Gln Glu
        195                 200                 205

Leu Asp Glu Ala Leu Gln Arg Glu Ile Gln Ala Phe Arg Thr Asp
210                 215                 220

Glu Ile Arg Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Asn Glu Arg Val
                260                 265                 270

Pro Tyr Asn Ala Pro Leu Ile Gln Phe Ser Ser Trp Met Gly Gly Asp
        275                 280                 285

Arg Asp Gly Asn Pro Arg Val Thr Pro Glu Val Thr Arg Asp Val Cys
        290                 295                 300

Leu Leu Ala Arg Met Met Ala Ala Asn Leu Tyr Tyr Ser Gln Ile Glu
305                 310                 315                 320

Asp Leu Met Phe Glu Leu Ser Met Trp Arg Cys Ser Asp Glu Leu Arg
                325                 330                 335

Val Arg Ala Asp Val Leu His Arg Ser Ser Lys Arg Asp Ser Lys His
                340                 345                 350

Tyr Ile Glu Phe Trp Lys Gln Ile Pro Pro Asn Glu Pro Tyr Arg Val
        355                 360                 365

Ile Leu Gly Glu Leu Arg Asp Arg Leu Tyr Gln Thr Arg Glu Arg Ser
        370                 375                 380

Arg Gln Leu Leu Ser His Gly Ile Ser Glu Thr Pro Glu Glu Ala Thr
385                 390                 395                 400

Phe Thr Asn Val Glu Gln Phe Leu Glu Pro Leu Glu Leu Cys Tyr Arg
                405                 410                 415

Ser Leu Cys Ser Cys Gly Asp Arg Pro Ile Ala Asp Gly Ser Leu Leu
                420                 425                 430

Asp Phe Leu Arg Gln Val Ser Thr Phe Gly Leu Ser Leu Val Arg Leu
        435                 440                 445

Asp Ile Arg Gln Glu Ser Asp Arg His Thr Asp Val Met Asp Ala Ile
        450                 455                 460

Thr Lys His Leu Glu Ile Gly Ser Tyr Arg Glu Trp Ser Glu Glu Gln
465                 470                 475                 480

Arg Gln Glu Trp Leu Leu Ser Glu Leu Ser Gly Lys Arg Pro Leu Phe
                485                 490                 495

Gly Pro Asp Leu Pro Lys Thr Glu Ile Ala Asp Val Leu Asp Thr
                500                 505                 510

Phe His Val Ile Ala Glu Leu Pro Ser Asp Ser Phe Gly Ala Tyr Ile
        515                 520                 525

Ile Ser Met Ala Thr Ala Ala Ser Asp Val Leu Ala Val Glu Leu Leu
        530                 535                 540

Gln Arg Glu Cys His Val Lys Gln Pro Leu Arg Val Val Pro Leu Phe
545                 550                 555                 560

Glu Lys Leu Ala Asp Leu Glu Ala Ala Pro Ala Ala Leu Ser Arg Leu
                565                 570                 575

Phe Ser Ile Glu Trp Tyr Arg Asp Gln Ile Asn Gly Lys Gln Glu Val
                580                 585                 590

Met Ile Gly Tyr Ser Asp Ser Gly Lys Asp Ala Gly Arg Phe Ser Ala
        595                 600                 605

Ala Trp Gln Leu Tyr Lys Ala Gln Glu Glu Leu Ile Lys Val Ala Lys

```
                610                 615                 620
Gln Tyr Gly Val Lys Leu Thr Met Phe His Gly Arg Gly Thr Val
625                 630                 635                 640

Gly Arg Gly Gly Pro Thr His Leu Ala Ile Leu Ser Gln Pro Pro
                645                 650                 655

Asp Thr Ile His Gly Ser Leu Arg Val Thr Val Gln Gly Glu Val Ile
                660                 665                 670

Glu Gln Ser Phe Gly Glu Glu His Leu Cys Phe Arg Thr Leu Gln Arg
                675                 680                 685

Phe Ala Ala Thr Leu Glu His Gly Met His Pro Pro Val Ser Pro
690                 695                 700

Lys Pro Glu Trp Arg Ala Leu Met Asp Glu Met Ala Val Val Ala Thr
705                 710                 715                 720

Glu Glu Tyr Arg Ser Ile Val Phe Lys Glu Pro Arg Phe Val Glu Tyr
                725                 730                 735

Phe Arg Leu Ala Thr Pro Glu Leu Glu Tyr Gly Arg Met Asn Ile Gly
                740                 745                 750

Ser Arg Pro Ser Lys Arg Lys Pro Ser Gly Gly Ile Glu Ser Leu Arg
                755                 760                 765

Ala Ile Pro Trp Ile Phe Ala Trp Thr Gln Thr Arg Phe His Leu Pro
770                 775                 780

Val Trp Leu Gly Phe Gly Ala Ala Phe Lys His Val Ile Gln Lys Asp
785                 790                 795                 800

Ile Arg Asn Leu His Met Leu Gln Glu Met Tyr Asn Glu Trp Pro Phe
                805                 810                 815

Phe Arg Val Thr Ile Asp Leu Val Glu Met Val Phe Ala Lys Gly Asp
                820                 825                 830

Pro Gly Ile Ala Ala Leu Asn Asp Lys Leu Leu Val Ser Lys Glu Leu
                835                 840                 845

Trp Pro Phe Gly Glu Lys Leu Arg Ala Asn Tyr Lys Glu Thr Lys Ser
                850                 855                 860

Leu Leu Leu Gln Ile Ala Gly His Lys Asp Leu Leu Glu Gly Asp Pro
865                 870                 875                 880

Tyr Leu Lys Gln Arg Leu Arg Leu Arg Asp Ser Tyr Ile Thr Thr Leu
                885                 890                 895

Asn Val Cys Gln Ala Tyr Thr Leu Lys Arg Ile Arg Asp Pro Asn Tyr
                900                 905                 910

Cys Val Thr Pro Arg Pro His Leu Ser Lys Glu Ile Met Glu Ser Asn
                915                 920                 925

Lys Pro Ala Asp Glu Leu Val Lys Leu Asn Pro Thr Ser Asp Tyr Ala
930                 935                 940

Pro Gly Met Glu Asp Thr Leu Ile Leu Thr Met Lys Gly Ile Ala Ala
945                 950                 955                 960

Gly Met Gln Asn Thr Gly
                965

<210> SEQ ID NO 11
<211> LENGTH: 964
<212> TYPE: PRT
<213> ORGANISM: Brassica oleracea

<400> SEQUENCE: 11

Met Pro His Gly Lys Leu Glu Lys Met Ala Ser Met Asp Val His Leu
1               5                   10                  15
```

-continued

```
Arg Gln Leu Val Pro Gly Lys Val Ser Glu Asp Lys Leu Val Glu
             20                  25                  30
Tyr Asp Ala Leu Leu Leu Asp Arg Phe Leu Asp Ile Leu Gln Glu Leu
         35                  40                  45
His Gly Glu Asp Leu Arg Glu Thr Val Gln Glu Leu Tyr Glu His Ser
 50                  55                  60
Ala Glu Tyr Glu Gly Lys His Glu Pro Lys Lys Leu Glu Glu Leu Gly
 65                  70                  75                  80
Asn Val Leu Thr Ser Leu Asp Pro Gly Asp Ser Ile Val Ile Ala Lys
                 85                  90                  95
Ala Phe Ser His Met Leu Asn Leu Ala Asn Leu Ala Glu Glu Val Gln
                100                 105                 110
Ile Ala Tyr Arg Arg Ile Lys Lys Leu Lys Lys Gly Asp Phe Val
            115                 120                 125
Asp Glu Ser Ser Ala Thr Thr Glu Ser Asp Leu Glu Glu Thr Phe Lys
130                 135                 140
Lys Leu Val Gly Asp Leu Asn Lys Ser Pro Glu Glu Ile Phe Asp Ala
145                 150                 155                 160
Leu Lys Asn Gln Thr Val Asp Leu Val Leu Thr Ala His Pro Thr Gln
                165                 170                 175
Ser Val Arg Arg Ser Leu Leu Gln Lys His Gly Arg Ile Arg Asp Cys
            180                 185                 190
Leu Ala Gln Leu Tyr Ala Lys Asp Ile Thr Pro Asp Lys Gln Glu
        195                 200                 205
Leu Asp Glu Ala Leu Gln Arg Glu Ile Gln Ala Ala Phe Arg Thr Asp
210                 215                 220
Glu Ile Lys Arg Thr Pro Pro Thr Pro Gln Asp Glu Met Arg Ala Gly
225                 230                 235                 240
Met Ser Tyr Phe His Glu Thr Ile Trp Lys Gly Val Pro Lys Phe Leu
                245                 250                 255
Arg Arg Val Asp Thr Ala Leu Lys Asn Ile Gly Ile Lys Glu Arg Val
            260                 265                 270
Pro Tyr Asn Ala Pro Leu Ile Gln Phe Ser Ser Trp Met Gly Gly Asp
        275                 280                 285
Arg Asp Gly Asn Pro Arg Val Thr Pro Glu Val Thr Arg Asp Val Cys
290                 295                 300
Leu Leu Ala Arg Met Met Ala Ala Thr Met Tyr Phe Asn Gln Ile Glu
305                 310                 315                 320
Asp Leu Met Phe Glu Leu Ser Met Trp Arg Cys Asn Asp Glu Leu Arg
                325                 330                 335
Val Arg Ala Asp Glu Leu His Val Asn Arg Arg Lys Asp Ala Ala Lys
            340                 345                 350
His Tyr Ile Glu Phe Trp Lys Ser Ile Pro Pro Thr Glu Pro Tyr Arg
        355                 360                 365
Val Val Leu Gly Asp Val Arg Asp Lys Leu Tyr His Thr Arg Glu Arg
    370                 375                 380
Ala Arg Gln Leu Leu Ser Asn Gly Thr Ser Asp Val Pro Glu Glu Ala
385                 390                 395                 400
Thr Phe Asn Asn Leu Glu Glu Phe Leu Glu Pro Leu Glu Leu Cys Tyr
                405                 410                 415
Arg Ser Leu Cys Ser Cys Gly Asp Arg Pro Ile Ala Asp Gly Ser Leu
            420                 425                 430
Leu Asp Phe Leu Arg Gln Val Ser Thr Phe Gly Leu Ser Leu Val Arg
```

```
            435                 440                 445
Leu Asp Ile Arg Gln Glu Ser Asp Arg His Thr Asp Val Leu Asp Ala
450                 455                 460

Ile Thr Thr His Leu Glu Ile Gly Ser Tyr Arg Asp Trp Ser Glu Glu
465                 470                 475                 480

Arg Arg Gln Glu Trp Leu Leu Ser Glu Leu Ser Gly Lys Arg Pro Leu
                    485                 490                 495

Phe Gly Ser Asp Leu Pro Lys Thr Glu Ile Ala Asp Val Leu Asp
                500                 505                 510

Thr Phe His Val Ile Ala Glu Leu Pro Ser Asp Ser Phe Gly Ala Tyr
                515                 520                 525

Ile Ile Ser Met Ala Thr Ala Pro Ser Asp Val Leu Ala Val Glu Leu
                530                 535                 540

Leu Gln Arg Glu Cys His Val Lys Arg Pro Leu Arg Val Val Pro Leu
545                 550                 555                 560

Phe Glu Lys Leu Ala Asp Leu Glu Ala Ala Pro Ala Ala Val Ala Arg
                565                 570                 575

Leu Phe Ser Val Asp Trp Tyr Lys Asn Arg Ile Asn Gly Lys Gln Glu
                580                 585                 590

Val Met Ile Gly Tyr Ser Asp Ser Gly Lys Asp Ala Gly Arg Leu Ser
                595                 600                 605

Ala Ala Trp Gln Leu Tyr Lys Ala Gln Glu Glu Leu Val Lys Val Ala
610                 615                 620

Lys Glu Tyr Gly Val Lys Leu Thr Met Phe His Gly Arg Gly Gly Thr
625                 630                 635                 640

Val Gly Arg Gly Gly Gly Pro Thr His Leu Ala Ile Leu Ser Gln Pro
                645                 650                 655

Pro Asp Thr Ile Asn Gly Ser Leu Arg Val Thr Val Gln Gly Glu Val
                660                 665                 670

Ile Glu Gln Ser Phe Gly Glu Glu His Leu Cys Phe Arg Thr Leu Gln
                675                 680                 685

Arg Phe Thr Ala Ala Thr Leu Glu His Gly Met Arg Pro Pro Val Ser
690                 695                 700

Pro Lys Pro Glu Trp Arg Glu Leu Leu Asp Glu Met Ala Val Val Ala
705                 710                 715                 720

Thr Glu Glu Tyr Arg Ser Val Val Phe Gln Glu Pro Arg Phe Val Glu
                725                 730                 735

Tyr Phe Arg Leu Ala Thr Pro Glu Leu Glu Tyr Gly Arg Met Asn Ile
                740                 745                 750

Gly Ser Arg Pro Ser Lys Arg Lys Pro Ser Gly Gly Ile Glu Ser Leu
                755                 760                 765

Arg Ala Ile Pro Trp Ile Phe Ala Trp Thr Gln Thr Arg Phe His Leu
770                 775                 780

Pro Val Trp Leu Gly Phe Gly Ala Ala Ile Arg His Val Val Glu Lys
785                 790                 795                 800

Asp Val Lys Asn Leu His Met Leu Gln Asp Met Tyr Gln His Trp Pro
                805                 810                 815

Phe Phe Arg Val Thr Ile Asp Leu Ile Glu Met Val Phe Ala Lys Gly
                820                 825                 830

Asp Pro Gly Ile Ala Ala Leu Tyr Asp Lys Leu Leu Val Ser Glu Glu
                835                 840                 845

Leu Trp Pro Phe Gly Asp Lys Leu Arg Ala Asn Phe Glu Glu Thr Lys
                850                 855                 860
```

-continued

```
Lys Leu Val Leu Gln Thr Ala Gly His Lys Asp Leu Leu Glu Gly Asp
865                 870                 875                 880

Pro Tyr Leu Lys Gln Arg Leu Arg Leu Arg Asn Ser Tyr Ile Thr Thr
            885                 890                 895

Leu Asn Val Cys Gln Ala Tyr Thr Leu Lys Arg Ile Arg Asp Pro Ser
                900                 905                 910

Tyr Asn Val Thr Leu Arg Pro His Ile Ser Lys Glu Ile Ala Glu Ser
            915                 920                 925

Ser Lys Glu Leu Ile Glu Leu Asn Pro Thr Ser Glu Tyr Ala Pro Gly
        930                 935                 940

Leu Glu Asp Thr Leu Ile Leu Thr Met Lys Gly Val Ala Ala Gly Leu
945                 950                 955                 960

Gln Asn Thr Gly

<210> SEQ ID NO 12
<211> LENGTH: 964
<212> TYPE: PRT
<213> ORGANISM: Brassica rapa

<400> SEQUENCE: 12

Met Pro His Gly Lys Leu Glu Lys Met Ala Ser Met Asp Val His Leu
1               5                   10                  15

Arg Gln Leu Val Pro Gly Lys Val Ser Glu Asp Lys Leu Val Glu
            20                  25                  30

Tyr Asp Ala Leu Leu Leu Asp Arg Phe Leu Asp Ile Leu Gln Glu Leu
            35                  40                  45

His Gly Glu Asp Leu Arg Glu Thr Val Gln Glu Leu Tyr Glu His Ser
        50                  55                  60

Ala Glu Tyr Glu Gly Lys His Glu Pro Lys Lys Leu Glu Glu Leu Gly
65                  70                  75                  80

Asn Val Leu Thr Ser Leu Asp Pro Gly Asp Ser Ile Val Ile Ala Lys
                85                  90                  95

Ala Phe Ser His Met Leu Asn Leu Ala Asn Leu Ala Glu Glu Val Gln
                100                 105                 110

Ile Ala Tyr Arg Arg Ile Lys Lys Leu Lys Lys Gly Asp Phe Val
            115                 120                 125

Asp Glu Ser Ser Ala Thr Thr Glu Ser Asp Leu Glu Glu Thr Phe Lys
            130                 135                 140

Lys Leu Val Gly Asp Leu Asn Lys Ser Pro Glu Glu Ile Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Gly Arg Ile Arg Asp Cys
            180                 185                 190

Leu Ala Gln Leu Tyr Ala Lys Asp Ile Thr Pro Asp Asp Lys Gln Glu
            195                 200                 205

Leu Asp Glu Ala Leu Gln Arg Glu Ile Gln Ala Ala Phe Arg Thr Asp
        210                 215                 220

Glu Ile Lys Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Glu Glu Arg Val
                260                 265                 270
```

```
Pro Tyr Asn Ala Pro Leu Ile Gln Phe Ser Ser Trp Met Gly Gly Asp
        275                 280                 285

Arg Asp Gly Asn Pro Arg Val Thr Pro Glu Val Thr Arg Asp Val Cys
    290                 295                 300

Leu Leu Ala Arg Met Met Ala Ala Thr Met Tyr Phe Asn Gln Ile Glu
305                 310                 315                 320

Asp Leu Met Phe Glu Leu Ser Met Trp Arg Cys Asn Asp Glu Leu Arg
                325                 330                 335

Val Arg Ala Asp Glu Leu His Val Asn Arg Arg Lys Asp Ala Ala Lys
            340                 345                 350

His Tyr Ile Glu Phe Trp Lys Ser Ile Pro Pro Thr Glu Pro Tyr Arg
        355                 360                 365

Val Val Leu Gly Asp Val Arg Asp Lys Leu Tyr His Thr Arg Glu Arg
    370                 375                 380

Ala Arg Gln Leu Leu Ser Asn Gly Thr Ser Asp Val Pro Glu Glu Ala
385                 390                 395                 400

Thr Phe Asn Asn Leu Glu Glu Phe Leu Glu Pro Leu Glu Leu Cys Tyr
                405                 410                 415

Arg Ser Leu Cys Ser Cys Gly Asp Arg Pro Ile Ala Asp Gly Ser Leu
            420                 425                 430

Leu Asp Phe Leu Arg Gln Val Ser Thr Phe Gly Leu Ser Leu Val Arg
        435                 440                 445

Leu Asp Ile Arg Gln Glu Ser Asp Arg His Thr Asp Val Leu Asp Ala
    450                 455                 460

Ile Thr Thr His Leu Glu Ile Gly Ser Tyr Arg Glu Trp Ser Glu Glu
465                 470                 475                 480

Arg Arg Gln Glu Trp Leu Leu Ser Glu Leu Ser Gly Lys Arg Pro Leu
                485                 490                 495

Phe Gly Ser Asp Leu Pro Lys Thr Glu Glu Ile Ala Asp Val Leu Asp
            500                 505                 510

Thr Phe His Val Ile Ala Glu Leu Pro Ser Asp Ser Phe Gly Ala Tyr
        515                 520                 525

Ile Ile Ser Met Ala Thr Ala Pro Ser Asp Val Leu Ala Val Glu Leu
    530                 535                 540

Leu Gln Arg Glu Cys His Val Lys Arg Pro Leu Arg Val Val Pro Leu
545                 550                 555                 560

Phe Glu Lys Leu Ala Asp Leu Glu Ala Ala Pro Ala Ala Val Ala Arg
                565                 570                 575

Leu Phe Ser Val Asp Trp Tyr Lys Asn Arg Ile Asn Gly Lys Gln Glu
            580                 585                 590

Val Met Ile Gly Tyr Ser Asp Ser Gly Lys Asp Ala Gly Arg Leu Ser
        595                 600                 605

Ala Ala Trp Gln Leu Tyr Lys Ala Gln Glu Glu Leu Val Lys Val Ala
    610                 615                 620

Lys Glu Tyr Gly Val Lys Leu Thr Met Phe His Gly Arg Gly Gly Thr
625                 630                 635                 640

Val Gly Arg Gly Gly Gly Pro Thr His Leu Ala Ile Leu Ser Gln Pro
                645                 650                 655

Pro Asp Thr Ile Asn Gly Ser Leu Arg Val Thr Val Gln Gly Glu Val
            660                 665                 670

Ile Glu Gln Ser Phe Gly Glu Glu His Leu Cys Phe Arg Thr Leu Gln
        675                 680                 685
```

```
Arg Phe Thr Ala Ala Thr Leu Glu His Gly Met Arg Pro Pro Val Ser
    690                 695                 700

Pro Lys Pro Glu Trp Arg Glu Leu Leu Asp Glu Met Ala Val Val Ala
705                 710                 715                 720

Thr Glu Glu Tyr Arg Ser Val Val Phe Gln Glu Pro Arg Phe Val Glu
                725                 730                 735

Tyr Phe Arg Leu Ala Thr Pro Glu Leu Glu Tyr Gly Arg Met Asn Ile
            740                 745                 750

Gly Ser Arg Pro Ser Lys Arg Lys Pro Ser Gly Gly Ile Glu Ser Leu
        755                 760                 765

Arg Ala Ile Pro Trp Ile Phe Ala Trp Thr Gln Thr Arg Phe His Leu
770                 775                 780

Pro Val Trp Leu Gly Phe Gly Ala Ala Ile Arg His Val Val Glu Lys
785                 790                 795                 800

Asp Val Lys Asn Leu His Met Leu Gln Asp Met Tyr Gln His Trp Pro
                805                 810                 815

Phe Phe Arg Val Thr Ile Asp Leu Ile Glu Met Val Phe Ala Lys Gly
            820                 825                 830

Asp Pro Gly Ile Ala Ala Leu Tyr Asp Lys Leu Leu Val Ser Glu Glu
        835                 840                 845

Leu Trp Pro Phe Gly Glu Lys Leu Arg Ala Asn Phe Glu Glu Thr Lys
850                 855                 860

Lys Leu Val Leu Gln Thr Ala Gly His Lys Asp Leu Leu Glu Gly Asp
865                 870                 875                 880

Pro Tyr Leu Lys Gln Arg Leu Arg Leu Arg Asn Ser Tyr Ile Thr Thr
                885                 890                 895

Leu Asn Val Cys Gln Ala Tyr Thr Leu Lys Arg Ile Arg Asp Pro Ser
            900                 905                 910

Tyr Asn Val Thr Leu Arg Pro His Ile Ser Lys Glu Ile Ala Glu Ser
        915                 920                 925

Ser Lys Glu Leu Ile Glu Leu Asn Pro Thr Ser Glu Tyr Ala Pro Gly
    930                 935                 940

Leu Glu Asp Thr Leu Ile Leu Thr Met Lys Gly Val Ala Ala Gly Leu
945                 950                 955                 960

Gln Asn Thr Gly

<210> SEQ ID NO 13
<211> LENGTH: 961
<212> TYPE: PRT
<213> ORGANISM: Malus domestica
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 13

Met Glu Glu Ala Glu Val Asp Ala Gln Val Arg Arg Ala Ala Gly Gly
1               5                   10                  15

Asn Gly Glu Xaa Glu Ala Thr Glu Lys Gln Gly Leu Glu Glu Asn Arg
            20                  25                  30

Asp Gly Leu Lys Val Leu Pro Phe Glu Phe Val Ala Leu Glu Ala Ala
        35                  40                  45

Cys Ser Val Gln Asp Cys Tyr Glu Leu Ser Ala Glu Tyr Glu Arg Lys
```

```
            50                  55                  60
Gln Asp Pro Gln Lys Leu Glu Leu Gly Lys Met Leu Thr Ser Leu
65                  70                  75                  80

Asp Pro Gly Asp Ser Ile Val Ile Ala Lys Ser Phe Ser His Met Leu
                85                  90                  95

Asn Leu Ala Asn Leu Ala Glu Glu Val Gln Ile Ala Tyr Arg Arg Arg
                100                 105                 110

Ile Lys Xaa Lys Lys Lys Gly Asp Phe Ala Asp Glu Ala Ser Ala Thr
                115                 120                 125

Thr Glu Ser Asp Ile Glu Glu Thr Leu Lys Arg Leu Val Gly Asp Leu
                130                 135                 140

Lys Lys Ser Pro Glu Glu Val Phe Asp Ala Leu Lys Asn Gln Thr Val
145                 150                 155                 160

Asp Leu Val Phe Thr Ala His Pro Thr Gln Ser Val Arg Arg Ser Leu
                165                 170                 175

Leu Gln Lys His Ala Arg Ile Arg Asn Cys Leu Thr Lys Leu Asn Ala
                180                 185                 190

Lys Asp Ile Thr Pro Asp Asp Lys Gln Glu Leu Asp Glu Ser Leu Gln
                195                 200                 205

Arg Glu Ile Gln Ala Ala Phe Arg Thr Asp Glu Ile Arg Arg Thr Pro
210                 215                 220

Pro Thr Pro Gln Asp Glu Met Arg Ala Gly Met Ser Tyr Phe His Glu
225                 230                 235                 240

Thr Ile Trp Lys Gly Val Pro Lys Phe Leu Arg Arg Val Asp Thr Ala
                245                 250                 255

Leu Lys Asn Ile Gly Ile Asn Glu Arg Val Pro Tyr Asn Ala Pro Leu
                260                 265                 270

Ile Gln Phe Ser Ser Trp Met Gly Gly Asp Arg Asp Gly Asn Pro Arg
                275                 280                 285

Val Thr Pro Glu Val Thr Arg Asp Val Cys Leu Leu Ala Arg Met Met
                290                 295                 300

Ala Ala Asn Leu Tyr Phe Ser Gln Ile Glu Asp Leu Met Phe Glu Leu
305                 310                 315                 320

Ser Met Trp Arg Cys Asn Asp Glu Leu Arg Ala Arg Ala His Glu Leu
                325                 330                 335

His Arg Ser Ser Lys Lys Asp Ala Lys His Tyr Ile Glu Phe Trp Lys
                340                 345                 350

Gln Ile Pro Pro Asn Glu Pro Tyr Arg Val Ile Leu Gly Asp Val Arg
                355                 360                 365

Asp Lys Leu Tyr Asn Thr Arg Glu Arg Ala Arg Gln Leu Leu Ala Asn
                370                 375                 380

Gly Val Ser Asp Ile Pro Glu Asp Thr Thr Phe Thr Asn Val Glu Gln
385                 390                 395                 400

Phe Leu Glu Pro Leu Glu Leu Cys Tyr Gln Ser Leu Cys Ser Cys Gly
                405                 410                 415

Asp Arg Ala Ile Ala Asp Gly Ser Leu Leu Asp Phe Leu Arg Gln Val
                420                 425                 430

Ser Thr Phe Gly Leu Ser Leu Val Arg Leu Asp Ile Arg Gln Glu Ser
                435                 440                 445

Asp Arg His Thr Asp Val Leu Asn Ala Ile Thr Lys His Leu Glu Ile
                450                 455                 460

Gly Ser Tyr Arg Glu Trp Ser Glu Glu Arg Arg Gln Glu Trp Leu Leu
465                 470                 475                 480
```

```
Ser Glu Leu Arg Gly Lys Arg Pro Leu Phe Gly Ala Asp Val Pro Lys
            485                 490                 495

Thr Glu Glu Ile Ala Asp Val Leu Asp Thr Phe His Val Ile Ala Glu
            500                 505                 510

Leu Pro Ser Asp Asn Phe Gly Ala Tyr Ile Ile Ser Met Ala Thr Ser
            515                 520                 525

Pro Ser Asp Val Leu Ala Val Glu Leu Leu Gln Arg Glu Cys Gly Val
            530                 535                 540

Lys Glu Pro Leu Arg Val Val Pro Leu Phe Glu Lys Leu Ala Asp Leu
545                 550                 555                 560

Glu Ala Ala Pro Ala Ala Val Ala Arg Leu Phe Ser Ile Asp Trp Tyr
                    565                 570                 575

Lys Asn Arg Ile Asn Gly Lys Gln Glu Val Met Ile Gly Tyr Ser Asp
            580                 585                 590

Ser Gly Lys Asp Ala Gly Arg Leu Ser Ala Ala Trp Gln Leu Tyr Lys
            595                 600                 605

Ala Gln Glu Glu Leu Val Lys Val Ala Lys Lys Phe Gly Val Lys Leu
            610                 615                 620

Thr Met Phe His Gly Arg Gly Gly Thr Val Gly Arg Gly Gly Gly Pro
625                 630                 635                 640

Thr His Leu Ala Ile Leu Ser Gln Pro Pro Asp Thr Ile His Gly Ser
                    645                 650                 655

Leu Arg Val Thr Val Gln Gly Glu Val Ile Glu Gln Ser Phe Gly Glu
            660                 665                 670

Glu His Leu Cys Phe Arg Thr Leu Gln Arg Phe Thr Ala Ala Thr Leu
            675                 680                 685

Glu His Gly Met His Pro Pro Val Ser Pro Lys Pro Glu Trp Arg Ala
            690                 695                 700

Leu Met Asp Glu Met Gly Val Ile Ala Thr Glu Glu Tyr Arg Ser Ile
705                 710                 715                 720

Val Phe Gln Glu Pro Arg Phe Val Glu Tyr Phe Arg Leu Ala Thr Pro
                    725                 730                 735

Glu Met Glu Tyr Gly Arg Met Asn Ile Gly Ser Arg Pro Ser Lys Arg
            740                 745                 750

Lys Pro Ser Gly Gly Ile Glu Ser Leu Arg Ala Ile Pro Trp Ile Phe
            755                 760                 765

Ala Trp Thr Gln Thr Arg Phe His Leu Pro Val Trp Leu Gly Phe Gly
770                 775                 780

Ala Ala Phe Lys His Val Ile Glu Lys Asp Ala Lys Asn Leu Gln Met
785                 790                 795                 800

Leu Arg Glu Met Tyr Asn Gln Trp Pro Phe Phe Arg Val Thr Ile Asp
                    805                 810                 815

Leu Ile Glu Met Val Phe Ala Lys Gly Asp Pro Gly Ile Ala Ser Leu
            820                 825                 830

Tyr Asp Lys Leu Leu Val Ser Glu Asp Leu Trp Ser Phe Gly Asp Arg
            835                 840                 845

Leu Arg Ala Asn Tyr Glu Gln Thr Lys Leu Leu Val Leu Gln Val Ala
            850                 855                 860

Gly His Lys Ala Leu Leu Glu Gly Asp Pro Tyr Leu Arg Gln Arg Leu
865                 870                 875                 880

Leu Leu Arg Asp Ser Tyr Ile Thr Thr Leu Asn Val Cys Gln Ala Tyr
                    885                 890                 895
```

```
Thr Leu Lys Gln Ile Arg Asp Pro Asn Tyr His Val Lys Val Arg Pro
            900                 905                 910

His Leu Ser Ser Glu Tyr Met Glu Thr Thr Thr Lys Pro Ala Ala Glu
        915                 920                 925

Leu Val Lys Leu Asn Pro Thr Ser Glu Tyr Ala Pro Gly Leu Glu Asp
    930                 935                 940

Thr Leu Ile Leu Thr Met Lys Gly Ile Ala Ala Gly Met Gln Asn Thr
945                 950                 955                 960

Gly

<210> SEQ ID NO 14
<211> LENGTH: 966
<212> TYPE: PRT
<213> ORGANISM: Glycine max

<400> SEQUENCE: 14

Met Gly Thr Arg Asn Phe Glu Lys Met Ala Ser Ile Asp Ala Gln Leu
1               5                   10                  15

Arg Leu Leu Ala Pro Ser Lys Val Ser Asp Asp Lys Leu Val Glu
            20                  25                  30

Tyr Asp Ala Leu Leu Leu Asp Arg Phe Leu Asp Ile Leu Gln Asp Leu
        35                  40                  45

His Gly Asp Asp Ile Arg Glu Thr Val Gln Asp Cys Tyr Glu Leu Ser
    50                  55                  60

Ala Glu Tyr Glu Gly Gln Asn Asn Pro Gln Lys Leu Glu Glu Leu Gly
65                  70                  75                  80

Asn Met Leu Thr Gly Leu Asp Ala Gly Asp Ser Ile Val Ile Ser Lys
                85                  90                  95

Ser Phe Ala His Met Leu Asn Leu Ala Asn Leu Ala Glu Glu Val Gln
            100                 105                 110

Ile Ala Tyr Arg Arg Ile Lys Leu Leu Lys Lys Gly Asp Phe Ala
        115                 120                 125

Asp Glu Asn Ser Ala Ile Thr Glu Ser Asp Ile Glu Glu Thr Phe Lys
130                 135                 140

Arg Leu Val Asn Gln Leu Lys Lys Thr Pro Gln Glu Ile Phe Asp Ala
145                 150                 155                 160

Leu Lys Ser Gln Thr Val Asp Leu Val Leu Thr Ala His Pro Thr Gln
                165                 170                 175

Ser Val Arg Arg Ser Leu Leu Gln Lys His Gly Arg Ile Arg Asn Cys
            180                 185                 190

Leu Thr Gln Leu Tyr Ala Lys Asp Ile Thr Pro Asp Lys Gln Glu
        195                 200                 205

Leu Asp Glu Ala Leu Gln Arg Glu Ile Gln Ala Ala Phe Arg Thr Asp
210                 215                 220

Glu Ile Arg Arg Thr Pro Pro Thr Pro Gln Asp Glu Met Arg Ala Gly
225                 230                 235                 240

Met Ser Tyr Phe His Glu Thr Ile Trp Lys Gly Ile Pro Lys Phe Leu
                245                 250                 255

Arg Arg Val Asp Thr Ala Leu Lys Asn Ile Gly Ile Asn Glu Arg Val
            260                 265                 270

Pro Tyr Asn Ala Pro Val Ile Gln Phe Ser Ser Trp Met Gly Gly Asp
        275                 280                 285

Arg Asp Gly Asn Pro Arg Val Thr Pro Glu Val Thr Arg Asp Val Cys
290                 295                 300
```

```
Leu Leu Ala Arg Met Met Ala Ala Asn Leu Tyr Phe Ser Gln Ile Glu
305                 310                 315                 320

Asp Leu Met Phe Glu Leu Ser Met Trp Arg Cys Asn Asp Glu Leu Arg
            325                 330                 335

Val Arg Ser Asp Glu Leu Leu Ser Ser Ser Lys Arg Asp Ala Lys His
            340                 345                 350

Tyr Ile Glu Phe Trp Lys Gln Ile Pro Pro Asn Glu Pro Tyr Arg Val
            355                 360                 365

Ile Leu Gly Asp Val Arg Asp Lys Leu Tyr Asn Thr Arg Glu Arg Ala
            370                 375                 380

Arg Gln Leu Leu Ala Asn Gly Ser Ser Glu Ile Pro Glu Glu Thr Thr
385                 390                 395                 400

Phe Thr Asn Val Glu Gln Phe Leu Glu Pro Leu Glu Leu Cys Tyr Arg
            405                 410                 415

Ser Leu Cys Ala Cys Gly Asp Gln Pro Ile Ala Asp Gly Ser Leu Leu
            420                 425                 430

Asp Phe Leu Arg Gln Val Ser Thr Phe Gly Leu Ser Leu Val Arg Leu
            435                 440                 445

Asp Ile Arg Gln Glu Ser Asp Arg His Thr Asp Val Met Asp Ala Ile
450                 455                 460

Thr Asn His Leu Glu Ile Gly Ser Tyr Arg Glu Trp Ser Glu Glu Arg
465                 470                 475                 480

Arg Gln Glu Trp Leu Leu Ser Glu Leu Ser Gly Lys Arg Pro Leu Phe
            485                 490                 495

Gly Pro Asp Leu Pro Lys Thr Glu Glu Ile Ala Asp Val Leu Glu Thr
            500                 505                 510

Phe His Val Ile Ala Glu Leu Pro Ser Asp Ser Phe Gly Ala Tyr Ile
            515                 520                 525

Ile Ser Met Ala Thr Ala Pro Ser Asp Val Leu Ser Val Glu Leu Leu
530                 535                 540

Gln Arg Glu Cys His Val Lys Gln Pro Leu Arg Val Val Pro Leu Phe
545                 550                 555                 560

Glu Lys Leu Ala Asp Leu Glu Ala Ala Pro Ala Ala Val Ala Arg Leu
            565                 570                 575

Phe Ser Ile Asp Trp Tyr Arg Asp Arg Ile Asn Gly Lys Gln Glu Val
            580                 585                 590

Met Ile Gly Tyr Ser Asp Ser Gly Lys Asp Ala Gly Arg Phe Ser Ala
            595                 600                 605

Ala Trp Ala Leu Tyr Lys Ala Gln Glu Glu Leu Ile Lys Val Ala Lys
            610                 615                 620

Glu Phe Gly Val Lys Leu Thr Met Phe His Gly Arg Gly Gly Thr Val
625                 630                 635                 640

Gly Arg Gly Gly Gly Pro Thr His Leu Ala Ile Leu Ser Gln Pro Pro
                645                 650                 655

Asp Thr Ile His Gly Ser Leu Arg Val Thr Val Gln Gly Glu Val Ile
            660                 665                 670

Glu Gln Ser Phe Gly Glu Glu His Leu Cys Phe Arg Thr Leu Gln Arg
            675                 680                 685

Phe Thr Ala Ala Thr Leu Glu His Gly Met His Pro Pro Val Ala Pro
            690                 695                 700

Lys Pro Glu Trp Arg Ala Leu Met Asp Glu Met Ala Val Ile Ala Thr
705                 710                 715                 720

Glu Glu Tyr Arg Ser Ile Val Phe Gln Glu Pro Arg Phe Val Glu Tyr
```

```
                725                 730                 735
Phe Arg Cys Ala Thr Pro Glu Leu Glu Tyr Gly Arg Met Asn Ile Gly
            740                 745                 750
Ser Arg Pro Ser Lys Arg Lys Pro Ser Gly Gly Ile Glu Ser Leu Arg
            755                 760                 765
Ala Ile Pro Trp Ile Phe Ala Trp Thr Gln Thr Arg Phe His Leu Pro
770                 775                 780
Val Trp Leu Gly Phe Gly Ala Ala Phe Ser His Val Ile Lys Lys Asp
785                 790                 795                 800
Pro Lys Asn Leu Gln Met Leu Gln Asp Met Tyr Asn Gln Trp Pro Phe
                805                 810                 815
Phe Arg Val Ser Leu Asp Leu Val Glu Met Val Phe Ala Lys Gly Asp
                820                 825                 830
Pro Gly Ile Ala Ala Leu Tyr Asp Lys Leu Leu Val Ser Glu Glu Leu
            835                 840                 845
Trp Pro Phe Gly Glu Arg Leu Arg Ser Met Phe Glu Glu Thr Lys Ser
850                 855                 860
Leu Leu Leu Gln Val Ala Gly His Lys Asp Leu Leu Glu Gly Asp Pro
865                 870                 875                 880
Tyr Leu Lys Gln Arg Leu Arg Leu Arg Asp Ser Tyr Ile Thr Thr Leu
                885                 890                 895
Asn Val Leu Gln Ala Tyr Thr Leu Lys Arg Ile Arg Asp Pro Asp Tyr
                900                 905                 910
His Val Lys Leu Arg Pro His Leu Ser Lys Asp Tyr Met Glu Ser Asn
            915                 920                 925
Lys Pro Ala Ala Glu Leu Val Lys Leu Asn Pro Thr Ser Asp Tyr Ala
            930                 935                 940
Pro Gly Leu Glu Asp Thr Leu Ile Leu Thr Met Lys Gly Ile Ala Ala
945                 950                 955                 960
Gly Met Gln Asn Thr Gly
                965

<210> SEQ ID NO 15
<211> LENGTH: 184
<212> TYPE: PRT
<213> ORGANISM: Kalanchoe fedtschenkoi

<400> SEQUENCE: 15

Met Leu Glu Met Asp Phe Gly Arg Arg Ser Ala Ser Tyr Tyr Glu Ile
1               5                   10                  15
Leu Gly Val Gly Phe Asp Ser Ser Ala Glu Glu Ile Arg Arg Ala Tyr
            20                  25                  30
Arg Lys Leu Ala Met Arg Trp His Pro Asp Lys Trp Ala Arg Asn Pro
        35                  40                  45
Ser Leu Leu Gly Glu Ala Lys Leu Arg Phe Gln Gln Ile Gln Glu Ala
    50                  55                  60
Tyr Ser Val Leu Ser Asp Gln Ser Lys Arg Thr Leu Tyr Asp Ala Gly
65                  70                  75                  80
Met Tyr Asp Pro Glu Glu Glu Gln Glu Gly Phe Ser Asp Phe Val
                85                  90                  95
Gln Glu Met Val Thr Leu Met Ala Lys Val Lys Arg Glu Glu Lys Ile
                100                 105                 110
Tyr Thr Leu Glu Glu Leu Gln Gly Met Phe Thr Glu Met Ala Lys Gly
            115                 120                 125
```

Phe Glu Ser Ser Gln Trp Tyr Phe Asp Ala Ser Asn Cys Gly Ala Ser
130                 135                 140

Ala Phe Asp Ser Ser Pro Phe Ala Glu Tyr Asn Asp His Ser Arg Gln
145                 150                 155                 160

Pro Thr Lys Lys Ala Arg Trp Asp Met Gly Val Gly Val Thr Ser Ser
                165                 170                 175

Gly Leu Thr Asn Gly Tyr Cys Asn
                180

<210> SEQ ID NO 16
<211> LENGTH: 228
<212> TYPE: PRT
<213> ORGANISM: Ananas comosus

<400> SEQUENCE: 16

Met Gly Thr Glu Gln Arg Asn Gly Arg Pro Arg Ser Tyr Tyr Ala Val
1               5                   10                  15

Leu Gly Val Ala Ala Asp Ala Ser Arg Ala Glu Ile Arg Ala Ala Tyr
                20                  25                  30

Arg Arg Leu Ala Met Arg Trp His Pro Asp Arg Asn Gly Arg Glu Pro
            35                  40                  45

Phe Met Val Asp Glu Ala Lys Arg Phe Gln Leu Ile Gln Glu Ala
50                  55                  60

Tyr Gln Val Leu Ser Asp Gln Lys Arg Arg Ala Leu Tyr Asp Ala Gly
65                  70                  75                  80

Leu Tyr Asp Pro Val Gln Asp Glu Glu Glu Val Glu Gly Phe His
                85                  90                  95

Asp Phe Met Gln Glu Met Leu Ser Leu Met Ala Thr Val Arg Arg Glu
                100                 105                 110

Val Asn Phe Glu Tyr Phe Lys Pro Val Pro Val Ile Glu Thr Gln Cys
                115                 120                 125

Ser Ile Glu Asp Leu Gln Arg Met Leu Asp Glu Met Ala Gln Ser Phe
130                 135                 140

Ala Pro Thr Gln Pro Pro Thr Tyr Cys Phe Gly Gly Lys Gly Ala Ser
145                 150                 155                 160

Thr Asn Pro Lys Arg Pro Ala Thr Tyr Cys Phe Gly Arg Gly Ala
                165                 170                 175

Ser Thr Ile Pro Lys Arg Pro Ala Thr Tyr Cys Phe Asp Gly Arg Gly
                180                 185                 190

Ala Ser Thr Asn Pro Lys Arg His Cys Asp Arg Asn Asp Ala Thr Thr
                195                 200                 205

Arg Trp Trp Ser Ser Ser His Val Ser Gly Val Asp Met Phe Gly His
210                 215                 220

Ala Ser Phe Cys
225

<210> SEQ ID NO 17
<211> LENGTH: 617
<212> TYPE: PRT
<213> ORGANISM: Kalanchoe fedtschenkoi

<400> SEQUENCE: 17

Met Ile Phe Tyr Leu Pro Ile Glu Trp Ile Phe Asp Ser Gly Ser Pro
1               5                   10                  15

Thr Trp Glu Pro Ala Glu Met Ala Ser Ser Ala Pro Thr Pro Ile Ser
                20                  25                  30

```
Ala Ile Phe Ser Ser Asn Pro Arg Arg Lys Leu Ser Ser Arg Asn His
         35                  40                  45

Gln Phe Thr Thr Lys Cys Val Ser Lys Glu Leu His Phe Asn His Asp
 50                  55                  60

Gly Ser Val Thr Arg Lys Leu Gln Ala Gly Val Asp Ile Val Ala Glu
 65                  70                  75                  80

Leu Val Gly Val Thr Leu Gly Pro Lys Gly Arg Asn Val Val Leu Gln
                 85                  90                  95

Asn Lys Tyr Gly Pro Pro Lys Ile Val Asn Asp Gly Glu Thr Val Leu
            100                 105                 110

Lys Glu Val Glu Leu Glu Asp Pro Leu Glu Asn Val Gly Val Lys Leu
        115                 120                 125

Val Arg Gln Ala Gly Ala Lys Thr Asn Ser Leu Ala Gly Asp Gly Ser
    130                 135                 140

Thr Ala Ser Val Val Leu Ala Arg Gly Leu Ile Ala Glu Gly Val Lys
145                 150                 155                 160

Val Ile Glu Ala Gly Val Asn Pro Ile Gln Val Ala Arg Gly Ile Val
                165                 170                 175

Lys Thr Ala Glu Gly Leu Val Ala Glu Leu Lys Leu Met Ser Arg Glu
            180                 185                 190

Val Glu Asp His Glu Leu Ala Asp Val Ala Ala Val Ser Ala Gly Asn
        195                 200                 205

Asp His Glu Val Gly Lys Met Ile Ala Ala Ala Ile Arg Glu Val Gly
    210                 215                 220

Arg Thr Gly Val Ile Thr Ile Gln Lys Gly Lys Ser Thr Glu Thr Ser
225                 230                 235                 240

Leu Gln Ile Val Glu Gly Met Gln Phe Asp Arg Gly Tyr Leu Ser Pro
                245                 250                 255

Tyr Phe Val Thr Asp Arg Gln Lys Arg Leu Val Glu Phe His Asp Cys
            260                 265                 270

Lys Leu Leu Leu Val Asp Lys Lys Ile Lys Asp Pro Lys Glu Met Phe
        275                 280                 285

Lys Val Leu Asp Thr Ala Val Lys Glu Lys Tyr Pro Ile Leu Ile Ile
    290                 295                 300

Ala Glu Gly Ile Glu Gln Ala Ala Leu Ala Pro Val Ile Arg Asn Lys
305                 310                 315                 320

Leu Arg Gly Ala Leu Lys Ala Val Ala Val Lys Ala Pro Ala Phe Gly
                325                 330                 335

Ala Arg Lys Ser Asn Ser Leu Asp Asp Ile Ala Val Leu Thr Gly Ala
            340                 345                 350

Thr Val Val Arg Asp Glu Met Gly Leu Val Leu Ser Lys Val Gly Lys
        355                 360                 365

Glu Val Leu Gly Ser Ala Ala Lys Val Val Thr Gln Asp Ser Thr
    370                 375                 380

Leu Ile Val Thr Asp Gly Ser Thr Arg Asp Ala Val Asp Gln Arg Val
385                 390                 395                 400

Ser Gln Ile Arg Ala Leu Val Glu Asn Thr Glu Glu Asn Phe Glu Lys
                405                 410                 415

Lys Ile Leu Lys Glu Arg Ile Ala Arg Leu Ser Gly Gly Ile Ala Ile
            420                 425                 430

Leu Glu Val Gly Ala Gln Thr Val Val Glu Leu Lys Asp Arg Gln Leu
        435                 440                 445

Arg Ile Glu Asp Ala Val Asn Ala Thr Lys Ala Ala Ile Glu Glu Gly
```

```
                    450                 455                 460
Ile Val Val Gly Gly Gly Cys Ser Leu Leu Arg Leu Ser Leu Lys Val
465                 470                 475                 480

Asp Glu Ile Lys Glu Arg Leu Glu Asn Glu Glu Gln Lys Met Gly Ala
                    485                 490                 495

Glu Ile Phe Arg Arg Ser Leu Ser Tyr Pro Ala Lys Leu Ile Ala Lys
                500                 505                 510

Asn Ala Gly Val Ser Gly Ser Ile Val Val Glu Lys Val Leu Ala Asn
                515                 520                 525

Gly Asp Val Asn Phe Gly Tyr Asn Ala Ala Lys Asp Cys Tyr Glu Asn
            530                 535                 540

Leu Met Ala Ala Gly Ile Ile Asp Pro Ala Lys Val Val Arg Cys Cys
545                 550                 555                 560

Ile Glu His Ala Ala Ser Val Ala Lys Thr Phe Leu Thr Val Asn Ala
                565                 570                 575

Val Val Ile Asp Leu Ile Glu Ser Gln Pro Arg Pro Arg Gln Trp Pro
            580                 585                 590

Pro Val Pro Pro Pro Thr Ser Gly Ile Gly Pro Leu Arg Ser Lys
        595                 600                 605

Phe Pro Thr Gly Leu Leu Asn Lys Arg
    610                 615

<210> SEQ ID NO 18
<211> LENGTH: 584
<212> TYPE: PRT
<213> ORGANISM: Ananas comosus

<400> SEQUENCE: 18

Met Ala Ala Ala Asn Ala Ile Ser Thr Ala Ser Met Leu Leu Ala Ser
1               5                   10                  15

Pro Arg Gln Glu Ile Leu Arg Lys Arg Ala Gly Pro Gly Arg Arg Thr
            20                  25                  30

Ser Gly His Arg Ser Met Ala Val Arg Ala Ala Ala Lys Asp Ile Ala
        35                  40                  45

Phe Asp Gln Ser Ser Arg Ser Ala Leu Gln Ala Gly Val Glu Lys Leu
    50                  55                  60

Ala Asn Ala Val Gly Val Thr Leu Gly Pro Arg Gly Arg Asn Val Val
65                  70                  75                  80

Leu Asp Glu Phe Gly Asn Pro Arg Val Val Asn Asp Gly Val Thr Ile
                85                  90                  95

Ala Arg Ala Ile Glu Leu Ala Asp Pro Met Glu Asn Ala Gly Ala Ala
            100                 105                 110

Leu Ile Arg Glu Val Ala Ser Lys Thr Asn Asp Ser Ala Gly Asp Gly
        115                 120                 125

Thr Thr Thr Ala Ser Val Leu Ala Arg Glu Ile Ile Lys Leu Gly Leu
130                 135                 140

Leu Ser Val Thr Ser Gly Ala Asn Pro Val Ser Leu Lys Lys Gly Ile
145                 150                 155                 160

Asp Lys Thr Val Gln Ala Leu Val Asp Glu Leu Glu Lys Lys Ala Arg
                165                 170                 175

Pro Val Lys Gly Arg Gly Asp Ile Lys Ala Ile Ala Ser Ile Ser Ser
            180                 185                 190

Gly Asn Asp Glu Phe Val Gly Thr Met Ile Ala Asp Ala Ile Asp Lys
        195                 200                 205
```

Val Gly Pro Asp Gly Val Leu Ser Ile Glu Ser Ser Ser Phe Glu
    210                 215                 220

Thr Thr Val Asp Val Glu Glu Gly Met Glu Ile Asp Arg Gly Tyr Ile
225                 230                 235                 240

Ser Pro Gln Phe Val Thr Asn Pro Lys Leu Leu Val Glu Phe Glu
            245                 250                 255

Asn Ala Arg Val Leu Val Thr Asp Gln Lys Ile Ser Thr Ile Lys Glu
            260                 265                 270

Ile Ile Pro Leu Leu Glu Lys Thr Thr Gln Leu Arg Ala Pro Leu Leu
            275                 280                 285

Ile Ile Ala Glu Asp Val Thr Gly Glu Ala Leu Ala Thr Leu Val Val
    290                 295                 300

Asn Lys Leu Arg Gly Ile Leu Asn Val Ala Ala Ile Lys Ala Pro Ser
305                 310                 315                 320

Phe Gly Glu Arg Arg Lys Ala Leu Leu Gln Asp Ile Ala Ile Val Thr
                325                 330                 335

Gly Ala Glu Phe Gln Ala Lys Asp Leu Gly Leu Leu Val Glu Asn Thr
            340                 345                 350

Thr Val Asp Gln Leu Gly Thr Ala Arg Lys Val Thr Val Ala Gln Ser
            355                 360                 365

Ser Thr Thr Ile Ile Ala Asp Ala Ala Ser Lys Asp Glu Ile Gln Ala
370                 375                 380

Arg Ile Ala Gln Ile Lys Lys Glu Leu Ala Glu Thr Asp Ser Val Tyr
385                 390                 395                 400

Asp Thr Glu Lys Leu Ala Glu Arg Ile Ala Lys Leu Ser Gly Gly Val
                405                 410                 415

Ala Val Ile Lys Val Gly Ala Ala Thr Glu Thr Glu Leu Glu Asp Arg
            420                 425                 430

Lys Leu Arg Ile Glu Asp Ala Lys Asn Ala Thr Phe Ala Ala Ile Glu
            435                 440                 445

Glu Gly Ile Val Pro Gly Gly Gly Ala Ala Tyr Val His Leu Ser Thr
450                 455                 460

Cys Val Pro Ala Ile Lys Asp Lys Leu Glu Asp Ala Asp Glu Arg Leu
465                 470                 475                 480

Gly Ala Asp Ile Ile Gln Lys Ala Leu Val Ala Pro Ala Ala Leu Ile
                485                 490                 495

Ala Asp Asn Ala Gly Val Glu Gly Val Val Glu Lys Val Lys
            500                 505                 510

Asp Ser Glu Trp Glu Val Gly Tyr Asn Ala Met Thr Asp Lys Tyr Glu
            515                 520                 525

Asn Leu Val Glu Ala Gly Val Ile Asp Pro Ala Lys Val Thr Arg Cys
530                 535                 540

Ala Leu Gln Asn Ser Ala Ser Val Ala Gly Met Val Leu Thr Thr Gln
545                 550                 555                 560

Ala Ile Val Val Glu Lys Pro Lys Pro Lys Ala Pro Val Pro Ala Gly
                565                 570                 575

Pro Pro Glu Gly Ser Leu Ala Ile
            580

<210> SEQ ID NO 19
<211> LENGTH: 585
<212> TYPE: PRT
<213> ORGANISM: Ananas comosus

<400> SEQUENCE: 19

```
Met Ala Thr Thr Asn Ala Leu Ser Ser Ala Ser Ile Leu Ser Ser Ser
1               5                   10                  15

Pro Arg His Ser Ser Leu Arg Arg Arg Val Gly Phe Gly Gln Arg Pro
            20                  25                  30

Ile Gly Gly Gly Lys Tyr Arg His Leu Val Val Arg Ala Arg Ala Lys
            35                  40                  45

Glu Ile Ala Phe Asp Gln Ser Ser Arg Ser Asn Leu Gln Ala Gly Ile
50                  55                  60

Asp Lys Leu Ala Asn Ala Val Gly Val Thr Leu Gly Pro Arg Gly Arg
65                  70                  75                  80

Asn Val Val Leu Asp Glu Phe Gly Asn Pro Lys Val Val Asn Asp Gly
                85                  90                  95

Val Thr Ile Ala Arg Ala Ile Glu Leu Ala Asp Pro Met Glu Asn Ala
            100                 105                 110

Gly Ala Ala Leu Ile Arg Glu Val Ala Ser Lys Thr Asn Asp Ser Ala
            115                 120                 125

Gly Asp Gly Thr Thr Thr Ala Ala Val Leu Ala Arg Glu Ile Ile Lys
130                 135                 140

Leu Gly Leu Leu Ser Val Thr Ser Gly Ala Asn Pro Val Ser Ile Lys
145                 150                 155                 160

Lys Gly Ile Asp Lys Thr Val Gln Gly Leu Val Glu Glu Leu Gln Lys
                165                 170                 175

Lys Ala Arg Pro Val Glu Gly Arg Gly Asp Ile Lys Ala Ile Ala Ser
            180                 185                 190

Ile Ser Ala Gly Asn Asp Glu Thr Ile Gly Asn Met Ile Ala Asp Ala
            195                 200                 205

Ile Asp Lys Val Gly Pro Asp Gly Val Leu Ser Ile Glu Ser Ser Ser
210                 215                 220

Ser Phe Glu Thr Thr Val Asn Val Glu Gly Met Glu Ile Asp Arg
225                 230                 235                 240

Gly Tyr Ile Ser Pro Gln Phe Val Thr Asn Leu Glu Lys Ser Ile Val
            245                 250                 255

Glu Phe Glu Asn Ala Arg Val Leu Val Thr Asp Gln Lys Ile Ser Thr
            260                 265                 270

Ile Ser Glu Ile Ile Pro Leu Leu Glu Lys Ala Thr Gln Leu Arg Ala
275                 280                 285

Pro Leu Leu Ile Ile Ala Glu Asp Val Thr Gly Glu Ala Leu Ala Thr
290                 295                 300

Leu Val Val Asn Lys Leu Arg Gly Ile Leu Asn Val Ala Ala Ile Lys
305                 310                 315                 320

Ala Pro Gly Phe Gly Glu Arg Arg Lys Ala Ile Leu Gln Asp Ile Ala
            325                 330                 335

Ile Leu Thr Gly Ala Glu Phe Leu Ala Lys Asp Leu Gly Phe Leu Val
            340                 345                 350

Glu Asn Thr Ala Val Glu Gln Leu Gly Thr Ala Arg Lys Val Thr Ile
            355                 360                 365

Ser Gln Asn Ser Thr Thr Ile Ile Ala Asp Ala Ala Thr Lys Asp Glu
            370                 375                 380

Ile Gln Ala Arg Ile Ala Gln Leu Lys Lys Glu Leu Ala Glu Thr Asp
385                 390                 395                 400

Ser Val Tyr Asp Ser Glu Lys Leu Ala Glu Arg Ile Ala Lys Leu Ser
                405                 410                 415
```

```
Gly Gly Val Ala Val Ile Lys Val Gly Ala Ala Thr Glu Thr Glu Leu
            420                 425                 430

Glu Asp Arg Lys Leu Arg Ile Glu Asp Ala Lys Asn Ala Thr Phe Ala
        435                 440                 445

Ala Ile Glu Glu Gly Ile Val Pro Gly Gly Ala Ala Tyr Val His
450                 455                 460

Leu Ser Thr Cys Val Pro Ala Phe Lys Asp Lys Met Asp Asp Pro Asp
465                 470                 475                 480

Glu Arg Leu Gly Val Asp Ile Ile Gln Lys Ala Leu Val Ala Pro Ala
                485                 490                 495

Ala Leu Ile Ala His Asn Ala Gly Val Glu Gly Glu Val Val Val Glu
            500                 505                 510

Lys Ile Lys Asp Arg Glu Trp Glu Ile Gly Tyr Asn Ala Met Asp Asp
            515                 520                 525

Glu Tyr Glu Asn Leu Val Glu Ala Gly Val Ile Asp Pro Ala Lys Val
        530                 535                 540

Thr Arg Cys Ala Leu Gln Asn Ala Ala Ser Val Ala Gly Met Val Leu
545                 550                 555                 560

Thr Thr Gln Ala Ile Val Val Glu Lys Pro Lys Arg Lys Ala Thr Ala
                565                 570                 575

Ala Ala Pro Pro Gln Gly Leu Gly Val
            580                 585

<210> SEQ ID NO 20
<211> LENGTH: 608
<212> TYPE: PRT
<213> ORGANISM: Ananas comosus

<400> SEQUENCE: 20

Met Ala Ser Ala Phe Gly Thr Ile Ser Thr Val Gly Leu Ala Ala Ala
1               5                   10                  15

Pro Ser Ser Phe Ala Lys Glu Lys Arg Leu Ser Ala Ser Glu Lys Leu
                20                  25                  30

Ser Ser Leu Ala Ser Ile Ser Ser Ser Val Gly Ala Arg Met Gln
            35                  40                  45

Asn Val Arg Leu Gln Lys Lys His Ser Ser Lys Ile Arg Ala Met Ala
        50                  55                  60

Lys Glu Leu Tyr Phe Asn Lys Asp Gly Ser Ala Ile Lys Lys Leu Gln
65                  70                  75                  80

Ile Gly Val Asn Lys Leu Ala Asp Leu Val Gly Val Thr Leu Gly Pro
                85                  90                  95

Lys Gly Arg Asn Val Val Leu Glu Ser Lys Tyr Gly Ser Pro Lys Ile
            100                 105                 110

Val Asn Asp Gly Val Thr Val Ala Lys Glu Val Glu Leu Glu Asp Pro
        115                 120                 125

Val Glu Asn Ile Gly Ala Lys Leu Val Arg Gln Ala Ala Lys Thr
    130                 135                 140

Asn Asp Leu Ala Gly Asp Gly Thr Thr Thr Ser Val Val Leu Ala Gln
145                 150                 155                 160

Gly Leu Ile Ala Glu Gly Val Lys Val Val Ala Gly Ala Asn Pro
            165                 170                 175

Val Gln Ile Thr Arg Gly Ile Glu Lys Thr Ser Lys Ser Leu Val Glu
        180                 185                 190

Glu Leu Lys Lys Met Ser Lys Glu Val Glu Asp Ser Glu Leu Ala Asp
            195                 200                 205
```

Val Ala Ala Val Ser Ala Gly Asn Asn Tyr Glu Ile Gly Asn Met Ile
210             215                 220

Ala Asp Ala Met Ser Lys Val Gly Arg Lys Gly Val Val Thr Leu Glu
225             230                 235                 240

Glu Gly Lys Ser Ala Glu Asn Ser Leu Tyr Val Val Glu Gly Met Gln
                245                 250                 255

Phe Asp Arg Gly Tyr Ile Ser Pro Tyr Phe Val Thr Asp Ser Glu Lys
            260                 265                 270

Met Thr Val Glu Tyr Glu Asn Cys Lys Leu Leu Val Asp Lys Lys
        275                 280                 285

Ile Thr Asn Ala Arg Asp Leu Ile Asn Val Leu Glu Asp Ala Ile Arg
    290                 295                 300

Gly Gly Tyr Pro Ile Ile Ile Val Ala Glu Glu Ile Glu Gln Glu Ala
305             310                 315                 320

Leu Ala Thr Leu Val Val Asn Lys Leu Arg Gly Ala Leu Lys Ile Ala
                325                 330                 335

Ala Leu Lys Ala Pro Gly Phe Gly Glu Arg Lys Ser Gln Tyr Leu Asp
            340                 345                 350

Asp Ile Ala Ile Leu Thr Gly Ala Thr Val Val Arg Asp Glu Val Gly
        355                 360                 365

Leu Ser Leu Asp Lys Ala Asp Lys Glu Val Leu Gly Thr Ala Ala Lys
370                 375                 380

Val Val Leu Thr Lys Asp Ser Thr Thr Ile Val Gly Asp Gly Ser Thr
385                 390                 395                 400

Gln Glu Gln Val Ala Lys Arg Val Ala Gln Ile Arg Asn Leu Ile Glu
                405                 410                 415

Ala Ala Glu Gln Glu Tyr Glu Lys Glu Lys Leu Asn Glu Arg Ile Ala
            420                 425                 430

Lys Leu Ser Gly Gly Val Ala Val Ile Gln Val Gly Ala Gln Thr Glu
        435                 440                 445

Thr Glu Leu Lys Glu Lys Lys Leu Arg Val Glu Asp Ala Leu Asn Ala
    450                 455                 460

Thr Lys Ala Ala Val Glu Glu Gly Ile Val Val Gly Gly Gly Cys Thr
465                 470                 475                 480

Leu Leu Arg Leu Ala Ser Lys Val Asp Ala Ile Lys Asp Thr Leu Glu
                485                 490                 495

Asn Asp Glu Gln Lys Val Gly Ala Asp Ile Val Lys Arg Ala Leu Ser
            500                 505                 510

Tyr Pro Leu Lys Leu Ile Ala Lys Asn Ala Gly Val Asn Gly Ser Val
        515                 520                 525

Val Thr Glu Lys Val Leu Ala Ser Asp Asn Leu Lys Phe Gly Tyr Asn
530                 535                 540

Ala Ala Thr Gly Lys Tyr Glu Asp Leu Met Ala Ala Gly Ile Ile Asp
545                 550                 555                 560

Pro Thr Lys Val Val Arg Cys Cys Leu Glu His Ala Ser Ser Val Ala
                565                 570                 575

Lys Thr Phe Leu Thr Ser Asp Val Val Val Glu Ile Lys Glu Pro
            580                 585                 590

Glu Pro Ala Pro Met Thr Asn Pro Met Asp Asn Ser Gly Tyr Gly Tyr
        595                 600                 605

<210> SEQ ID NO 21
<211> LENGTH: 648

```
<212> TYPE: PRT
<213> ORGANISM: Kalanchoe fedtschenkoi

<400> SEQUENCE: 21

Met Ala Gly Lys Gly Glu Gly Pro Ala Ile Gly Ile Asp Leu Gly Thr
1               5                   10                  15

Thr Tyr Ser Cys Val Gly Val Trp Gln His Asp Arg Val Glu Ile Ile
            20                  25                  30

Ala Asn Asp Gln Gly Asn Arg Thr Thr Pro Ser Tyr Val Ala Phe Thr
        35                  40                  45

Asp Thr Glu Arg Leu Ile Gly Asp Ala Ala Lys Asn Gln Val Ala Met
    50                  55                  60

Asn Pro Val Asn Thr Val Phe Asp Ala Lys Arg Leu Ile Gly Arg Arg
65                  70                  75                  80

Phe Ser Asp Pro Ser Val Gln Ala Asp Met Lys Leu Trp Pro Phe Lys
                85                  90                  95

Val Ile Pro Gly Pro Gly Asp Lys Pro Met Ile Val Val Asn Tyr Lys
            100                 105                 110

Gly Glu Glu Lys Gln Phe Ser Ala Glu Glu Ile Ser Ser Met Val Leu
        115                 120                 125

Ile Lys Met Arg Glu Ile Ala Glu Ala Tyr Leu Gly Phe Ser Val Lys
    130                 135                 140

Asn Ala Val Val Thr Val Pro Ala Tyr Phe Asn Asp Ser Gln Arg Gln
145                 150                 155                 160

Ala Thr Lys Asp Ala Gly Val Ile Ala Gly Leu Asn Val Met Arg Ile
                165                 170                 175

Ile Asn Glu Pro Thr Ala Ala Ala Ile Ala Tyr Gly Leu Asp Lys Lys
            180                 185                 190

Ala Thr Ser Val Gly Glu Lys Asn Val Leu Ile Phe Asp Leu Gly Gly
        195                 200                 205

Gly Thr Phe Asp Val Ser Leu Leu Thr Ile Glu Glu Gly Ile Phe Glu
    210                 215                 220

Val Lys Ala Thr Ala Gly Asp Thr His Leu Gly Gly Glu Asp Phe Asp
225                 230                 235                 240

Asn Arg Leu Val Asn His Phe Val Gln Glu Phe Lys Arg Lys His Lys
                245                 250                 255

Lys Asp Ile Ser Gly Asn Pro Arg Ala Leu Arg Arg Leu Arg Thr Ala
            260                 265                 270

Cys Glu Arg Ala Lys Arg Thr Leu Ser Ser Thr Ala Gln Thr Thr Ile
        275                 280                 285

Glu Ile Asp Ser Leu Tyr Glu Gly Ile Asp Phe Tyr Ser Thr Ile Thr
    290                 295                 300

Arg Ala Arg Phe Glu Glu Leu Asn Met Asp Leu Phe Arg Lys Cys Met
305                 310                 315                 320

Glu Pro Val Glu Lys Cys Leu Arg Asp Ala Lys Met Asp Lys Thr Ser
                325                 330                 335

Val His Asp Ile Val Leu Val Gly Gly Ser Thr Arg Ile Pro Lys Val
            340                 345                 350

Gln Gln Leu Leu Gln Asp Phe Phe Asn Gly Lys Glu Leu Cys Lys Ser
        355                 360                 365

Ile Asn Pro Asp Glu Ala Val Ala Tyr Gly Ala Ala Val Gln Ala Ala
    370                 375                 380

Ile Leu Ser Gly Glu Gly Asn Glu Lys Val Gln Asp Leu Leu Leu Leu
385                 390                 395                 400
```

```
Asp Val Thr Pro Leu Ser Leu Gly Leu Glu Thr Ala Gly Gly Val Met
            405                 410                 415

Thr Val Leu Ile Pro Arg Asn Thr Thr Ile Pro Thr Lys Lys Glu Gln
            420                 425                 430

Val Phe Ser Thr Tyr Ala Asp Asn Gln Pro Gly Val Leu Ile Gln Val
            435                 440                 445

Tyr Glu Gly Glu Arg Ala Arg Thr Lys Asp Asn Asn Leu Leu Gly Lys
        450                 455                 460

Phe Glu Leu Ser Gly Ile Pro Pro Ala Pro Arg Gly Val Pro Gln Ile
465                 470                 475                 480

Thr Val Cys Phe Asp Ile Asp Ala Asn Gly Ile Leu Asn Val Ser Ala
                485                 490                 495

Glu Asp Lys Thr Thr Gly Gln Lys Asn Lys Ile Thr Ile Thr Asn Asp
                500                 505                 510

Lys Gly Arg Leu Ser Lys Glu Glu Ile Glu Lys Met Val Gln Glu Ala
            515                 520                 525

Glu Lys Tyr Lys Ser Glu Asp Glu His Lys Lys Val Glu Ala
        530                 535                 540

Lys Asn Ala Leu Glu Asn Tyr Ala Tyr Asn Met Arg Asn Thr Ile Lys
545                 550                 555                 560

Asp Glu Lys Ile Ser Glu Lys Leu Pro Ala Ala Asp Lys Lys Lys Ile
                565                 570                 575

Glu Asp Val Ile Asp Gln Ala Ile His Trp Leu Asp Ser Asn Gln Leu
                580                 585                 590

Ala Glu Ala Asp Glu Phe Glu Asp Lys Met Lys Glu Leu Glu Ser Val
            595                 600                 605

Cys Asn Pro Ile Ile Ala Lys Met Tyr Gln Gly Gly Asp Ala Gly Met
            610                 615                 620

Gly Gly Ala Met Asp Glu Asp Gly Pro Ser Val Gly Thr Gly Gly Ala
625                 630                 635                 640

Gly Pro Lys Ile Glu Glu Val Asp
                645
```

<210> SEQ ID NO 22
<211> LENGTH: 647
<212> TYPE: PRT
<213> ORGANISM: Kalanchoe fedtschenkoi

<400> SEQUENCE: 22

```
Met Ala Gly Lys Gly Glu Gly Pro Ala Ile Gly Ile Asp Leu Gly Thr
1               5                   10                  15

Thr Tyr Ser Cys Val Gly Val Trp Gln His Asp Arg Val Glu Ile Ile
            20                  25                  30

Ala Asn Asp Gln Gly Asn Arg Thr Thr Pro Ser Tyr Val Ala Phe Thr
        35                  40                  45

Asp Ser Glu Arg Leu Ile Gly Asp Ala Ala Lys Asn Gln Val Ala Met
    50                  55                  60

Asn Pro Ile Asn Thr Val Phe Asp Ala Lys Arg Leu Ile Gly Arg Arg
65                  70                  75                  80

Phe Ser Asp Ala Ser Val Gln Ser Asp Met Lys Leu Trp Pro Phe Lys
                85                  90                  95

Val Ile Pro Gly Pro Gly Asp Lys Pro Met Ile Val Val Gln Tyr Lys
            100                 105                 110

Gly Glu Glu Lys Gln Phe Ser Ala Glu Glu Ile Ser Ser Met Val Leu
```

```
            115                 120                 125
Met Lys Met Lys Glu Ile Ala Glu Ala Tyr Leu Gly Thr Thr Ile Lys
            130                 135                 140

Asn Ala Val Val Thr Val Pro Ala Tyr Phe Asn Asp Ser Gln Arg Gln
145                 150                 155                 160

Ala Thr Lys Asp Ala Gly Val Ile Ser Gly Leu Asn Val Met Arg Ile
                165                 170                 175

Ile Asn Glu Pro Thr Ala Ala Ile Ala Tyr Gly Leu Asp Lys Lys
            180                 185                 190

Ala Thr Ser Val Gly Glu Lys Asn Val Leu Ile Phe Asp Leu Gly Gly
            195                 200                 205

Gly Thr Phe Asp Val Ser Leu Leu Thr Ile Glu Glu Gly Ile Phe Glu
        210                 215                 220

Val Lys Ala Thr Ala Gly Asp Thr His Leu Gly Gly Glu Asp Phe Asp
225                 230                 235                 240

Asn Arg Leu Val Asn His Phe Val Gln Glu Phe Lys Arg Lys His Lys
                245                 250                 255

Lys Asp Ile Thr Gly Asn Pro Arg Ala Leu Arg Arg Leu Arg Thr Ala
            260                 265                 270

Cys Glu Arg Ala Lys Arg Thr Leu Ser Ser Thr Ala Gln Thr Thr Ile
        275                 280                 285

Glu Ile Asp Ser Leu Tyr Glu Gly Val Asp Phe Tyr Ser Thr Ile Thr
        290                 295                 300

Arg Ala Arg Phe Glu Glu Leu Asn Met Asp Leu Phe Arg Lys Cys Met
305                 310                 315                 320

Glu Pro Val Glu Lys Cys Leu Arg Asp Ala Lys Met Asp Lys Asn Ser
                325                 330                 335

Val His Asp Val Val Leu Val Gly Gly Ser Thr Arg Ile Pro Lys Val
            340                 345                 350

Gln Gln Leu Leu Gln Asp Phe Phe Asn Gly Lys Glu Leu Cys Lys Ser
        355                 360                 365

Ile Asn Pro Asp Glu Ala Val Ala Tyr Gly Ala Ala Val Gln Ala Ala
        370                 375                 380

Ile Leu Ser Gly Glu Gly Asn Glu Lys Val Gln Asp Leu Leu Leu Leu
385                 390                 395                 400

Asp Val Thr Pro Leu Ser Leu Gly Leu Glu Thr Ala Gly Gly Val Met
                405                 410                 415

Thr Val Leu Ile Pro Arg Asn Thr Thr Ile Pro Thr Lys Lys Glu Gln
            420                 425                 430

Val Phe Ser Thr Tyr Ser Asp Asn Gln Pro Gly Val Leu Ile Gln Val
        435                 440                 445

Tyr Glu Gly Glu Arg Thr Arg Thr Arg Asp Asn Asn Leu Leu Gly Lys
        450                 455                 460

Phe Glu Leu Ser Gly Ile Pro Pro Ala Pro Arg Gly Val Pro Gln Ile
465                 470                 475                 480

Thr Val Cys Phe Asp Ile Asp Ala Asn Gly Ile Leu Asn Val Ser Ala
                485                 490                 495

Glu Asp Lys Thr Thr Gly Gln Lys Asn Lys Ile Thr Ile Thr Asn Asp
            500                 505                 510

Lys Gly Arg Leu Ser Lys Glu Glu Ile Glu Lys Met Val Gln Glu Ala
        515                 520                 525

Glu Lys Tyr Lys Ser Glu Asp Glu Glu His Lys Lys Val Glu Ala
        530                 535                 540
```

```
Lys Asn Ala Leu Glu Asn Tyr Ala Tyr Asn Met Arg Asn Thr Ile Lys
545                 550                 555                 560

Asp Glu Lys Ile Gly Glu Lys Leu Pro Pro Ala Asp Lys Lys Lys Ile
            565                 570                 575

Glu Asp Ala Ile Asp Ala Ile Ser Trp Leu Asp Ser Asn Gln Leu
            580                 585                 590

Ala Glu Ala Asp Glu Phe Glu Asp Lys Met Lys Glu Leu Glu Ser Leu
        595                 600                 605

Cys Asn Pro Ile Ile Ala Lys Met Tyr Gln Gly Ala Gly Gly Pro Asp
        610                 615                 620

Val Gly Ala Ala Asp Asp Ile Pro Ser Thr Gly Gly Ser Gly Ala Gly
625                 630                 635                 640

Pro Lys Ile Glu Glu Val Asp
                645

<210> SEQ ID NO 23
<211> LENGTH: 624
<212> TYPE: PRT
<213> ORGANISM: Ananas comosus

<400> SEQUENCE: 23

Thr Lys Pro Ala Ala Asn Asp Ile Ile Gly Ile Asp Leu Gly Thr Thr
1               5                   10                  15

Asn Ser Cys Val Ala Val Met Glu Gly Lys Asn Pro Lys Val Ile Glu
            20                  25                  30

Asn Ser Glu Gly Ser Arg Thr Thr Pro Ser Val Val Ala Phe Thr Pro
        35                  40                  45

Lys Gly Glu Leu Leu Val Gly Thr Pro Ala Lys Arg Gln Ala Val Thr
    50                  55                  60

Asn Pro Ala Asn Thr Phe Phe Gly Thr Lys Arg Leu Ile Gly Arg Arg
65                  70                  75                  80

Phe Asp Asp Pro Leu Val Gln Lys Glu Met Lys Met Val Pro Tyr Lys
                85                  90                  95

Ile Val Lys Ala Pro Asn Gly Asp Ala Trp Val Glu Thr Thr Asp Gly
            100                 105                 110

Lys Gln Phe Ser Pro Ser Gln Val Gly Ala Phe Val Leu Thr Lys Met
        115                 120                 125

Lys Glu Thr Ala Asp Ser Tyr Leu Gly Lys Ser Val Ser Lys Ala Val
    130                 135                 140

Ile Thr Val Pro Ala Tyr Phe Asn Asp Ala Gln Arg Gln Ala Thr Lys
145                 150                 155                 160

Asp Ala Gly Arg Ile Ala Gly Leu Asp Val Gln Arg Ile Ile Asn Glu
                165                 170                 175

Pro Thr Ala Ala Ala Leu Ser Tyr Gly Thr Asn Asn Lys Glu Gly Leu
            180                 185                 190

Ile Ala Val Phe Asp Leu Gly Gly Thr Phe Asp Ile Ser Ile Leu
        195                 200                 205

Glu Ile Ser Asn Gly Val Phe Glu Val Lys Ala Thr Asn Gly Asp Thr
    210                 215                 220

Phe Leu Gly Gly Glu Asp Phe Asp Asn Val Leu Val Glu Tyr Leu Val
225                 230                 235                 240

Asn Glu Phe Lys Arg Thr Glu Gly Ile Asp Leu Ser Lys Asp Arg Leu
                245                 250                 255

Ala Leu Gln Arg Leu Arg Glu Ala Ala Glu Lys Ala Lys Ile Glu Leu
```

```
              260                 265                 270
Ser Ser Thr Thr Gln Thr Glu Ile Asn Leu Pro Phe Ile Thr Ala Asp
            275                 280                 285
Ala Ser Gly Ala Lys His Met His Ile Ala Leu Thr Arg Ser Lys Phe
            290                 295                 300
Glu Ser Leu Ile Asn His Leu Ile Glu Arg Thr Arg Glu Pro Cys Lys
305                 310                 315                 320
Asn Cys Leu Lys Asp Ala Asn Val Ser Thr Lys Asp Ile Asp Glu Val
                325                 330                 335
Leu Leu Val Gly Gly Met Thr Arg Val Pro Lys Val Gln Glu Val Val
                340                 345                 350
Ala Glu Leu Phe Gly Lys Thr Pro Ser Lys Gly Val Asn Pro Asp Glu
            355                 360                 365
Ala Val Ala Met Gly Ala Ala Ile Gln Gly Gly Ile Leu Arg Gly Asp
            370                 375                 380
Val Lys Glu Leu Leu Leu Leu Asp Ile Thr Pro Leu Ser Leu Gly Ile
385                 390                 395                 400
Glu Thr Leu Gly Gly Val Phe Thr Arg Leu Ile Asn Arg Asn Thr Thr
                405                 410                 415
Ile Pro Thr Lys Lys Ser Gln Val Phe Ser Thr Ala Ala Asp Asn Gln
                420                 425                 430
Thr Gln Val Gly Ile Arg Val Leu Gln Gly Glu Arg Glu Met Ala Ala
            435                 440                 445
Asp Asn Lys Leu Leu Gly Glu Phe Glu Leu Val Gly Ile Pro Pro Thr
450                 455                 460
Pro Arg Gly Met Pro Gln Ile Glu Val Thr Phe Asp Ile Asp Ala Asn
465                 470                 475                 480
Gly Ile Val Thr Val Ser Ala Lys Asp Lys Ala Thr Gly Lys Glu Gln
                485                 490                 495
Gln Ile Thr Ile Arg Ser Ser Gly Gly Leu Ser Glu Glu Ile Gln
                500                 505                 510
Lys Met Val Lys Glu Ala Glu Leu His Ala Gln Lys Asp Gln Glu Arg
            515                 520                 525
Lys Ala Leu Ile Asp Val Arg Asn Thr Ala Asp Ser Thr Leu Tyr Ser
            530                 535                 540
Ile Glu Lys Ser Leu Ser Glu Tyr Arg Asp Lys Ile Pro Ser Asp Val
545                 550                 555                 560
Val Ser Glu Ile Glu Asn Ala Ile Ala Asp Leu Arg Lys Glu Met Ser
                565                 570                 575
Gly Asp Asp Val Glu Lys Ile Lys Ala Lys Ile Asp Ala Ala Asn Lys
            580                 585                 590
Ala Val Ser Lys Ile Gly Gln His Met Thr Gly Gly Ser Lys Gly
            595                 600                 605
Ser Gly Ser Asp Glu Thr Pro Glu Ala Glu Tyr Glu Glu Val Lys Lys
610                 615                 620

<210> SEQ ID NO 24
<211> LENGTH: 50
<212> TYPE: PRT
<213> ORGANISM: Kalanchoe fedtschenkoi

<400> SEQUENCE: 24

Pro Leu Phe Gly Pro Asp Leu Pro Lys Thr Glu Glu Ile Ala Asp Val
1               5                   10                  15
```

-continued

```
Leu Gly Thr Phe Asp Val Ile Ala Glu Leu Pro Ser Asp Asn Phe Gly
            20                  25                  30

Ala Tyr Ile Ile Ser Met Ala Thr Ser Pro Ser Asp Val Leu Ala Val
        35                  40                  45

Glu Leu
    50

<210> SEQ ID NO 25
<211> LENGTH: 50
<212> TYPE: PRT
<213> ORGANISM: Kalanchoe fedtschenkoi

<400> SEQUENCE: 25

Pro Leu Phe Gly Pro Asp Leu Pro Lys Thr Glu Glu Ile Ala Asp Val
1               5                   10                  15

Leu Gly Thr Phe Asp Val Ile Ala Glu Leu Pro Ala Asp Asn Phe Gly
            20                  25                  30

Ala Tyr Ile Ile Ser Met Ala Thr Ser Pro Ser Asp Val Leu Ala Val
        35                  40                  45

Glu Leu
    50

<210> SEQ ID NO 26
<211> LENGTH: 50
<212> TYPE: PRT
<213> ORGANISM: Kalanchoe laxiflora

<400> SEQUENCE: 26

Pro Leu Phe Gly Pro Asp Leu Pro Lys Thr Glu Glu Ile Ala Asp Val
1               5                   10                  15

Leu Gly Thr Phe Asp Val Ile Ala Glu Leu Pro Ala Asp Asn Phe Gly
            20                  25                  30

Ala Tyr Ile Ile Ser Met Ala Thr Ser Pro Ser Asp Val Leu Ala Val
        35                  40                  45

Glu Leu
    50

<210> SEQ ID NO 27
<211> LENGTH: 50
<212> TYPE: PRT
<213> ORGANISM: Kalanchoe laxiflora

<400> SEQUENCE: 27

Pro Leu Phe Gly Pro Asp Leu Pro Lys Thr Glu Glu Ile Ala Asp Val
1               5                   10                  15

Leu Gly Thr Phe Asp Val Ile Ala Glu Leu Pro Ala Asp Asn Phe Gly
            20                  25                  30

Ala Tyr Ile Ile Ser Met Ala Thr Ser Pro Ser Asp Val Leu Ala Val
        35                  40                  45

Glu Leu
    50

<210> SEQ ID NO 28
<211> LENGTH: 50
<212> TYPE: PRT
<213> ORGANISM: Kalanchoe laxiflora

<400> SEQUENCE: 28

Pro Leu Phe Gly Pro Asp Leu Pro Lys Thr Glu Glu Ile Ala Asp Val
1               5                   10                  15
```

Leu Gly Thr Phe Asp Val Ile Ala Glu Leu Pro Ser Asp Asn Phe Gly
            20                  25                  30

Ala Tyr Ile Ile Ser Met Ala Thr Ser Pro Ser Asp Val Leu Ala Val
            35                  40                  45

Glu Leu
     50

<210> SEQ ID NO 29
<211> LENGTH: 50
<212> TYPE: PRT
<213> ORGANISM: Kalanchoe laxiflora

<400> SEQUENCE: 29

Pro Leu Phe Gly Pro Asp Leu Pro Lys Thr Glu Glu Ile Ala Asp Val
1               5                   10                  15

Leu Gly Thr Phe Asp Val Ile Ala Glu Leu Pro Ser Asp Asn Phe Gly
            20                  25                  30

Ala Tyr Ile Ile Ser Met Ala Thr Ser Pro Ser Asp Val Leu Ala Val
            35                  40                  45

Glu Leu
     50

<210> SEQ ID NO 30
<211> LENGTH: 50
<212> TYPE: PRT
<213> ORGANISM: x Mokara cv. 'Yellow'

<400> SEQUENCE: 30

Pro Leu Phe Gly Ser Asp Leu Pro Lys Thr Glu Glu Ile Ala Asp Val
1               5                   10                  15

Leu Gly Ala Phe Asp Val Ile Ala Glu Leu Pro Ser Asp Gly Phe Gly
            20                  25                  30

Ala Tyr Ile Ile Ser Met Ala Thr Ala Thr Ser Asp Val Leu Ala Val
            35                  40                  45

Glu Leu
     50

<210> SEQ ID NO 31
<211> LENGTH: 50
<212> TYPE: PRT
<213> ORGANISM: Phalaenopsis equestris

<400> SEQUENCE: 31

Pro Leu Phe Gly Pro Asp Leu Pro Lys Thr Glu Glu Ile Ala Asp Val
1               5                   10                  15

Leu Gly Ala Phe Asp Val Ile Ala Glu Leu Pro Ser Asp Gly Phe Gly
            20                  25                  30

Ala Tyr Val Ile Ser Met Ala Thr Ala Thr Ser Asp Val Leu Ala Val
            35                  40                  45

Glu Leu
     50

<210> SEQ ID NO 32
<211> LENGTH: 50
<212> TYPE: PRT
<213> ORGANISM: Zea mays

<400> SEQUENCE: 32

Pro Leu Phe Gly Ser Asp Leu Pro Lys Thr Glu Glu Ile Ala Asp Val

```
                1               5                   10                  15
Leu Asp Thr Phe His Val Ile Ala Glu Leu Pro Ser Asp Asn Phe Gly
            20                  25                  30

Ala Tyr Ile Ile Ser Met Ala Thr Ala Pro Ser Asp Val Leu Ala Val
        35                  40                  45

Glu Leu
    50

<210> SEQ ID NO 33
<211> LENGTH: 50
<212> TYPE: PRT
<213> ORGANISM: Populus trichocarpa

<400> SEQUENCE: 33

Pro Leu Phe Gly Pro Asp Leu Pro Lys Thr Glu Glu Ile Ala Asp Val
1               5                   10                  15

Leu Asp Thr Phe His Val Ile Ala Glu Leu Pro Ser Asp Ser Phe Gly
            20                  25                  30

Ala Tyr Ile Ile Ser Met Ala Thr Ala Ala Ser Asp Val Leu Ala Val
        35                  40                  45

Glu Leu
    50

<210> SEQ ID NO 34
<211> LENGTH: 50
<212> TYPE: PRT
<213> ORGANISM: Brassica oleracea

<400> SEQUENCE: 34

Pro Leu Phe Gly Ser Asp Leu Pro Lys Thr Glu Glu Ile Ala Asp Val
1               5                   10                  15

Leu Asp Thr Phe His Val Ile Ala Glu Leu Pro Ser Asp Ser Phe Gly
            20                  25                  30

Ala Tyr Ile Ile Ser Met Ala Thr Ala Pro Ser Asp Val Leu Ala Val
        35                  40                  45

Glu Leu
    50

<210> SEQ ID NO 35
<211> LENGTH: 50
<212> TYPE: PRT
<213> ORGANISM: Brassica rapa

<400> SEQUENCE: 35

Pro Leu Phe Gly Ser Asp Leu Pro Lys Thr Glu Glu Ile Ala Asp Val
1               5                   10                  15

Leu Asp Thr Phe His Val Ile Ala Glu Leu Pro Ser Asp Ser Phe Gly
            20                  25                  30

Ala Tyr Ile Ile Ser Met Ala Thr Ala Pro Ser Asp Val Leu Ala Val
        35                  40                  45

Glu Leu
    50

<210> SEQ ID NO 36
<211> LENGTH: 50
<212> TYPE: PRT
<213> ORGANISM: Malus domestica

<400> SEQUENCE: 36
```

```
Pro Leu Phe Gly Ala Asp Val Pro Lys Thr Glu Glu Ile Ala Asp Val
1               5                   10                  15

Leu Asp Thr Phe His Val Ile Ala Glu Leu Pro Ser Asp Asn Phe Gly
            20                  25                  30

Ala Tyr Ile Ile Ser Met Ala Thr Ser Pro Ser Asp Val Leu Ala Val
        35                  40                  45

Glu Leu
    50

<210> SEQ ID NO 37
<211> LENGTH: 50
<212> TYPE: PRT
<213> ORGANISM: Glycine max

<400> SEQUENCE: 37

Pro Leu Phe Gly Pro Asp Leu Pro Lys Thr Glu Glu Ile Ala Asp Val
1               5                   10                  15

Leu Glu Thr Phe His Val Ile Ala Glu Leu Pro Ser Asp Ser Phe Gly
            20                  25                  30

Ala Tyr Ile Ile Ser Met Ala Thr Ala Pro Ser Asp Val Leu Ser Val
        35                  40                  45

Glu Leu
    50

<210> SEQ ID NO 38
<211> LENGTH: 5
<212> TYPE: PRT
<213> ORGANISM: Cocculus laurifolius

<400> SEQUENCE: 38

Asn Ser Arg Leu Glu
1               5

<210> SEQ ID NO 39
<211> LENGTH: 5
<212> TYPE: PRT
<213> ORGANISM: Arabidopsis thaliana

<400> SEQUENCE: 39

Asn Ser Glu Leu Glu
1               5

<210> SEQ ID NO 40
<211> LENGTH: 5
<212> TYPE: PRT
<213> ORGANISM: Phyllanthus sp.

<400> SEQUENCE: 40

Asn Ser Arg Leu Glu
1               5

<210> SEQ ID NO 41
<211> LENGTH: 5
<212> TYPE: PRT
<213> ORGANISM: Vitis vinifera

<400> SEQUENCE: 41

Asn Ser Glu Leu Glu
1               5

<210> SEQ ID NO 42
<211> LENGTH: 5
```

```
<212> TYPE: PRT
<213> ORGANISM: Kalanchoe crenato-diagremontiana

<400> SEQUENCE: 42

Asn Ala Arg Leu Glu
1               5

<210> SEQ ID NO 43
<211> LENGTH: 5
<212> TYPE: PRT
<213> ORGANISM: Kalanchoe fedtschenkoi

<400> SEQUENCE: 43

Asn Ala Arg Leu Glu
1               5

<210> SEQ ID NO 44
<211> LENGTH: 5
<212> TYPE: PRT
<213> ORGANISM: Solanum lycopersicum

<400> SEQUENCE: 44

Asn Ala Glu Leu Glu
1               5

<210> SEQ ID NO 45
<211> LENGTH: 5
<212> TYPE: PRT
<213> ORGANISM: Mimulus guttatus

<400> SEQUENCE: 45

Asn Ser Glu Leu Glu
1               5

<210> SEQ ID NO 46
<211> LENGTH: 5
<212> TYPE: PRT
<213> ORGANISM: Sorghum bicolor

<400> SEQUENCE: 46

Asn Ser Glu Leu Glu
1               5

<210> SEQ ID NO 47
<211> LENGTH: 5
<212> TYPE: PRT
<213> ORGANISM: Setaria italica

<400> SEQUENCE: 47

Asn Ser Glu Met Glu
1               5

<210> SEQ ID NO 48
<211> LENGTH: 5
<212> TYPE: PRT
<213> ORGANISM: Oryza sativa

<400> SEQUENCE: 48

Asn Ser Glu Leu Glu
1               5

<210> SEQ ID NO 49
<211> LENGTH: 5
<212> TYPE: PRT
<213> ORGANISM: Brachypodium distachyon
```

<400> SEQUENCE: 49

Asn Ser Glu Leu Glu
1               5

<210> SEQ ID NO 50
<211> LENGTH: 5
<212> TYPE: PRT
<213> ORGANISM: Ananas comosus

<400> SEQUENCE: 50

Asn Ser Glu Leu Glu
1               5

<210> SEQ ID NO 51
<211> LENGTH: 5
<212> TYPE: PRT
<213> ORGANISM: Musa acuminata

<400> SEQUENCE: 51

Asn Ser Glu Leu Glu
1               5

<210> SEQ ID NO 52
<211> LENGTH: 5
<212> TYPE: PRT
<213> ORGANISM: Phalaenopsis equestris

<400> SEQUENCE: 52

Asn Met Arg Leu Glu
1               5

<210> SEQ ID NO 53
<211> LENGTH: 5
<212> TYPE: PRT
<213> ORGANISM: Amborella trichopoda

<400> SEQUENCE: 53

Asn Ser Glu Leu Glu
1               5

<210> SEQ ID NO 54
<211> LENGTH: 8
<212> TYPE: PRT
<213> ORGANISM: Artificial Sequence
<220> FEATURE:
<223> OTHER INFORMATION: Polypeptide

<400> SEQUENCE: 54

Asp Thr Phe Arg Val Thr Ala Glu
1               5

<210> SEQ ID NO 55
<211> LENGTH: 8
<212> TYPE: PRT
<213> ORGANISM: Artificial Sequence
<220> FEATURE:
<223> OTHER INFORMATION: Polypeptide

<400> SEQUENCE: 55

Asp Thr Phe Lys Val Ala Ala Glu
1               5

<210> SEQ ID NO 56
<211> LENGTH: 8

```
<212> TYPE: PRT
<213> ORGANISM: Artificial Sequence
<220> FEATURE:
<223> OTHER INFORMATION: Polypeptide

<400> SEQUENCE: 56

Asp Thr Phe Arg Val Ala Ala Glu
1               5

<210> SEQ ID NO 57
<211> LENGTH: 8
<212> TYPE: PRT
<213> ORGANISM: Artificial Sequence
<220> FEATURE:
<223> OTHER INFORMATION: Polypeptide

<400> SEQUENCE: 57

Asp Thr Phe Arg Val Ala Ala Gln
1               5

<210> SEQ ID NO 58
<211> LENGTH: 8
<212> TYPE: PRT
<213> ORGANISM: Artificial Sequence
<220> FEATURE:
<223> OTHER INFORMATION: Polypeptide

<400> SEQUENCE: 58

Asp Thr Phe His Val Ile Ala Glu
1               5

<210> SEQ ID NO 59
<211> LENGTH: 8
<212> TYPE: PRT
<213> ORGANISM: Artificial Sequence
<220> FEATURE:
<223> OTHER INFORMATION: Polypeptide

<400> SEQUENCE: 59

Gly Thr Phe His Val Leu Ala Glu
1               5

<210> SEQ ID NO 60
<211> LENGTH: 8
<212> TYPE: PRT
<213> ORGANISM: Artificial Sequence
<220> FEATURE:
<223> OTHER INFORMATION: Polypeptide

<400> SEQUENCE: 60

Gly Ala Phe His Val Leu Ala Glu
1               5

<210> SEQ ID NO 61
<211> LENGTH: 8
<212> TYPE: PRT
<213> ORGANISM: Artificial Sequence
<220> FEATURE:
<223> OTHER INFORMATION: Polypeptide

<400> SEQUENCE: 61

Gly Cys Phe His Val Leu Ala Glu
1               5

<210> SEQ ID NO 62
<211> LENGTH: 8
<212> TYPE: PRT
```

```
<213> ORGANISM: Artificial Sequence
<220> FEATURE:
<223> OTHER INFORMATION: Polypeptide

<400> SEQUENCE: 62

Gly Ala Met Arg Val Leu Ala Glu
1               5

<210> SEQ ID NO 63
<211> LENGTH: 8
<212> TYPE: PRT
<213> ORGANISM: Artificial Sequence
<220> FEATURE:
<223> OTHER INFORMATION: Polypeptide

<400> SEQUENCE: 63

Gly Thr Phe Arg Val Leu Ala Glu
1               5

<210> SEQ ID NO 64
<211> LENGTH: 8
<212> TYPE: PRT
<213> ORGANISM: Artificial Sequence
<220> FEATURE:
<223> OTHER INFORMATION: Polypeptide

<400> SEQUENCE: 64

Gly Thr Phe Arg Val Ile Ala Glu
1               5

<210> SEQ ID NO 65
<211> LENGTH: 8
<212> TYPE: PRT
<213> ORGANISM: Artificial Sequence
<220> FEATURE:
<223> OTHER INFORMATION: Polypeptide

<400> SEQUENCE: 65

Gly Ala Phe Arg Val Ile Ala Glu
1               5

<210> SEQ ID NO 66
<211> LENGTH: 8
<212> TYPE: PRT
<213> ORGANISM: Artificial Sequence
<220> FEATURE:
<223> OTHER INFORMATION: Polypeptide

<400> SEQUENCE: 66

Gln Thr Leu His Val Ile Ala Glu
1               5

<210> SEQ ID NO 67
<211> LENGTH: 8
<212> TYPE: PRT
<213> ORGANISM: Artificial Sequence
<220> FEATURE:
<223> OTHER INFORMATION: Polypeptide

<400> SEQUENCE: 67

Gln Thr Phe His Val Ile Ala Glu
1               5

<210> SEQ ID NO 68
<211> LENGTH: 8
<212> TYPE: PRT
<213> ORGANISM: Artificial Sequence
```

```
<220> FEATURE:
<223> OTHER INFORMATION: Polypeptide

<400> SEQUENCE: 68

Asp Thr Leu Arg Val Ile Ala Glu
1               5

<210> SEQ ID NO 69
<211> LENGTH: 8
<212> TYPE: PRT
<213> ORGANISM: Artificial Sequence
<220> FEATURE:
<223> OTHER INFORMATION: Polypeptide

<400> SEQUENCE: 69

Asp Thr Phe Lys Val Ile Ser Glu
1               5

<210> SEQ ID NO 70
<211> LENGTH: 8
<212> TYPE: PRT
<213> ORGANISM: Artificial Sequence
<220> FEATURE:
<223> OTHER INFORMATION: Polypeptide

<400> SEQUENCE: 70

Asp Thr Phe His Val Ile Ser Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Polypeptide

<400> SEQUENCE: 71

Gly Thr Phe Asp Val Ile Ala Glu
1               5

<210> SEQ ID NO 72
<211> LENGTH: 8
<212> TYPE: PRT
<213> ORGANISM: Artificial Sequence
<220> FEATURE:
<223> OTHER INFORMATION: Polypeptide

<400> SEQUENCE: 72

Gly Ala Phe Asp Val Ile Ala Glu
1               5

<210> SEQ ID NO 73
<211> LENGTH: 8
<212> TYPE: PRT
<213> ORGANISM: Artificial Sequence
<220> FEATURE:
<223> OTHER INFORMATION: Polypeptide

<400> SEQUENCE: 73

Asp Thr Phe His Val Ile Ala Glu
1               5

<210> SEQ ID NO 74
<211> LENGTH: 8
<212> TYPE: PRT
<213> ORGANISM: Artificial Sequence
<220> FEATURE:
```

```
<223> OTHER INFORMATION: Polypeptide

<400> SEQUENCE: 74

Asn Thr Phe Arg Val Ile Ala Glu
1               5

<210> SEQ ID NO 75
<211> LENGTH: 8
<212> TYPE: PRT
<213> ORGANISM: Artificial Sequence
<220> FEATURE:
<223> OTHER INFORMATION: Polypeptide

<400> SEQUENCE: 75

Asn Thr Phe Ala Val Ile Ala Glu
1               5

<210> SEQ ID NO 76
<211> LENGTH: 8
<212> TYPE: PRT
<213> ORGANISM: Artificial Sequence
<220> FEATURE:
<223> OTHER INFORMATION: Polypeptide

<400> SEQUENCE: 76

Asp Thr Phe His Val Ile Ala Glu
1               5

<210> SEQ ID NO 77
<211> LENGTH: 8
<212> TYPE: PRT
<213> ORGANISM: Artificial Sequence
<220> FEATURE:
<223> OTHER INFORMATION: Polypeptide

<400> SEQUENCE: 77

Asn Thr Phe His Val Ile Ser Glu
1               5

<210> SEQ ID NO 78
<211> LENGTH: 8
<212> TYPE: PRT
<213> ORGANISM: Artificial Sequence
<220> FEATURE:
<223> OTHER INFORMATION: Polypeptide

<400> SEQUENCE: 78

Asp Thr Leu His Val Ile Ala Glu
1               5

<210> SEQ ID NO 79
<211> LENGTH: 8
<212> TYPE: PRT
<213> ORGANISM: Artificial Sequence
<220> FEATURE:
<223> OTHER INFORMATION: Polypeptide

<400> SEQUENCE: 79

Asp Thr Phe Lys Val Ile Ser Glu
1               5

<210> SEQ ID NO 80
<211> LENGTH: 8
<212> TYPE: PRT
<213> ORGANISM: Artificial Sequence
<220> FEATURE:
<223> OTHER INFORMATION: Polypeptide
```

```
<400> SEQUENCE: 80

Asp Thr Phe Arg Val Ile Ala Glu
1               5

<210> SEQ ID NO 81
<211> LENGTH: 8
<212> TYPE: PRT
<213> ORGANISM: Artificial Sequence
<220> FEATURE:
<223> OTHER INFORMATION: Polypeptide

<400> SEQUENCE: 81

Glu Thr Phe His Val Leu Ala Glu
1               5

<210> SEQ ID NO 82
<211> LENGTH: 8
<212> TYPE: PRT
<213> ORGANISM: Artificial Sequence
<220> FEATURE:
<223> OTHER INFORMATION: Polypeptide

<400> SEQUENCE: 82

Asp Thr Phe His Val Leu Ala Glu
1               5

<210> SEQ ID NO 83
<211> LENGTH: 8
<212> TYPE: PRT
<213> ORGANISM: Artificial Sequence
<220> FEATURE:
<223> OTHER INFORMATION: Polypeptide

<400> SEQUENCE: 83

Asp Thr Phe His Val Leu Ala Lys
1               5

<210> SEQ ID NO 84
<211> LENGTH: 8
<212> TYPE: PRT
<213> ORGANISM: Artificial Sequence
<220> FEATURE:
<223> OTHER INFORMATION: Polypeptide

<400> SEQUENCE: 84

Asp Thr Phe His Val Ile Ala Glu
1               5
```

GENES FOR ENHANCING DROUGHT AND HEAT TOLERANCE IN PLANTS AND METHODS OF USE

CROSS REFERENCE TO RELATED APPLICATION

This application claims the benefit of priority of U.S. Provisional Application No. 62/523,294, filed Jun. 22, 2017, the entire contents of which are incorporated herein by reference.

STATEMENT REGARDING FEDERALLY SPONSORED RESEARCH OR DEVELOPMENT

This invention was made with government support under Prime Contract No. DE-AC05-00OR22725 awarded by the U.S. Department of Energy. The government has certain rights in the invention.

INCORPORATION BY REFERENCE OF SEQUENCE LISTING

The Sequence Listing in an ASCII text file, 36087_SEQ1_ST25.txt of 168 KB, created on Jun. 21, 2018, and submitted to the United States Patent and Trademark Office via EFS-Web, is incorporated herein by reference.

BACKGROUND

Most of the present-day crops for food, feed, fiber, and biofuel production use either C3 or C4 photosynthesis. The production of these C3 or C4 crops is negatively impacted by drought and heat stress. This problem will be exacerbated by the predicted global warming in the years to come. Crassulacean acid metabolism (CAM) is a water-conserving photosynthetic pathway that enhances plant water-use efficiency (WUE) and drought tolerance by reducing transpirational water loss through daytime stomatal closure (West-Eberhard et al., 2011, *Science*, 332: 311-312). WUE of CAM plants is approximately six-fold higher than that of C3 plants and three-fold higher than that of C4 plants under comparable conditions (Borland et al., 2009, *Journal of Experimental Botany*, 60: 2879-2896). CAM species are believed to have great potential for sustainable food and biomass production on semi-arid, abandoned or marginal agricultural lands in the face of increasing human population and global warming (Borland et al. 2009, *Journal of Experimental Botany*, 60: 2879-2896; Cushman et al. 2015, *Journal of Experimental Botany*, 66: 4177-4193). The diel cycle of CAM can be divided into two major phases: 1) Nocturnal uptake of atmospheric $CO_2$ via open stomata and fixation of carbon (C) by phosphoenolpyruvate-carboxylase (PEPC), leading to the formation of malic acid that is stored in the central vacuoles of typically succulent photosynthetic organs; 2) Daytime C3 photosynthesis mediated by ribulose-1,5-bis-phosphate carboxylase/oxygenase (RuBisCO) that re-fixes $CO_2$ generated from decarboxylation of malic acid when stomatal conductance is at a minimum (Rascher et al., 2001, *PNAS*, 98: 11801-11805; Owen and Griffiths, 2013, *New Phytologist*, 200: 1116-1131; Borland et al., 2014, *Trends in Plant Science*, 19: 327-338; Yang et al., 2015, *New Phytologist*, 207: 491-504). CAM is found in over 400 genera across 36 families of vascular plants (Yang et al. 2015, *New Phytologist*, 207: 491-504) and is thought to have evolved multiple times from diverse C3 lineages (Silvera et al., 2010, *Functional Plant Biology*, 37: 995-1010). How- ever, the molecular basis of CAM evolution remains unclear. The core biochemical characteristics of the CAM cycle are similar in the plant lineages where CAM has evolved, with some variation in the enzymes that catalyze malate decarboxylation during the day and in the storage carbohydrates that provide substrates for malic acid synthesis at night (Christopher and Holtum, 1996, *Plant Physiology*, 112: 393-399; Christopher and Holtum, 1998, *Australian Journal of Plant Physiology*, 25: 371-376; Holtum et al., 2005, *Functional Plant Biology*, 32: 429-449).

BRIEF SUMMARY OF THE DISCLOSURE

In one aspect, this disclosure provides a method of improving drought and heat tolerance in a plant or plant cell, comprising introducing into the plant an exogenous nucleic acid encoding at least one heat shock protein (HSP) selected from the group consisting of HSP40, HSP60 and HSP70, and further providing in the plant a nucleic acid encoding a phosphoenolpyruvate carboxylase (PEPC) comprising an aspartic acid (D) at a position corresponding to position 509 of SEQ ID NO: 4.

In some embodiments, the providing step comprises expressing an exogenous nucleic acid encoding a PEPC comprising an aspartic acid (D) at a position corresponding to position 509 of SEQ ID NO: 4.

In some embodiments, the providing step comprises expressing an exogenous nucleic acid encoding a PEPC of a CAM plant species.

In some embodiments, the providing step comprises introducing a mutation into the endogenous PEPC gene wherein the resulting mutated gene encodes a PEPC comprising an aspartic acid (D) at a position corresponding to position 509 of SEQ ID NO: 4.

In a specific embodiment, the mutation is introduced by genome editing, which is achieved by a method selected from the group consisting of CRISPR/Cas system, Cre/Lox system, TALEN system, ZFNs system and homologous recombination.

In some embodiments, the CRISPR/Cas system comprises introducing into the plant a first nucleic acid encoding a Cas9 or Cas12 (previously called Cpf1) nuclease, a second nucleic acid comprising a guide RNA (gRNA), and a third nucleic acid comprising a homologous repair template of a PEPC gene wherein the third nucleic acid encodes an aspartic acid (D) at a position corresponding to position 509 of SEQ ID NO: 4.

In some embodiments, the exogenous nucleic acid encoding at least one HSP is expressed during daytime and the nucleic acid encoding PEPC is expressed during night time.

In some embodiments, the exogenous nucleic acid encoding at least one HSP and nucleic acid encoding PEPC are expressed constitutively.

In some embodiments, the exogenous nucleic acid encoding at least one HSP is stably transfected or transformed into the plant genome.

In some embodiments, wherein the exogenous nucleic acid encoding at least one HSP is expressed in the leaf tissue.

In some embodiments, the plant is a C3 plant selected from the group consisting of genera *Allium*, *Arabidopsis*, *Brassica*, *Capsicum*, *Citrullus*, *Cucumis*, *Eucalyptus*, *Fragaria*, *Glycine*, *Gossypium*, *Hordeum*, *Ipomoea*, *Malus*, *Manihot*, *Nicotiana*, *Oryza*, *Populus*, *Prunus*, *Rosa*, *Solanum*, *Spinacia* and *Triticum*.

In some embodiments, the plant is a C4 plant selected from the group consisting of genera *Panicum*, *Saccharum*, *Setaria*, *Sorghum* and *Zea*.

In some embodiments, the CAM plant species is selected from the group consisting of genera *Kalanchoe, Phalaenopsis, Ananas* and *Crassula*.

In some embodiments, the HSP40, HSP60 and HSP70 are expressed simultaneously or separately in a plant.

A different aspect of this disclosure provides a genetically-modified plant or plant cell. In some embodiments, the plant is modified to express an exogenous nucleic acid encoding at least one HSP selected from the group consisting of HSP40, HSP60 and HSP70, and wherein the plant is further modified to express a nucleic acid encoding a PEPC comprising an aspartic acid (D) at a position corresponding to position 509 of SEQ ID NO: 4.

In some embodiments, the PEPC is expressed from the endogenous PEPC gene mutated to encode an aspartic acid (D) at a position corresponding to position 509 of SEQ ID NO: 4.

In some embodiments, the exogenous nucleic acid encoding the at least one HSP and the nucleic acid encoding the PEPC are expressed constitutively.

In some embodiments, the exogenous nucleic acid encoding the at least one HSP is expressed during daytime and the nucleic acid encoding the PEPC is expressed during night time.

In some embodiments, the genetically-modified plant is a C3 plant or a C4 plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia, Triticum, Panicum, Saccharum, Setaria, Sorghum,* and *Zea*.

A different aspect of this invention is directed towards an expression vector, comprising a nucleotide sequence operably linked to a regulatory region that is functional in a plant or plant cell, wherein the nucleotide sequence encodes a HSP selected from the group consisting of HSP40, HSP60, HSP70, and a PEPC comprising an aspartic acid (D) at a position corresponding to position 509 of SEQ ID NO: 4.

In some embodiments, the expression vector directs temporally controlled expression of the nucleotide sequence. In some embodiments, the temporally controlled expression comprises gene expression during nighttime. In some embodiments, the temporally controlled expression comprises gene expression during daytime.

In some embodiments, the regulatory region comprises a promoter selected from the group consisting of a constitutive promoter, a tissue-specific promoter, and a regulated promoter.

In some embodiments, the tissue-specific promoter is a leaf-specific promoter. In a specific embodiment, the leaf-specific promoter is selected from the group consisting of a ribulose-1,5-bisphosphate carboxylase/oxygenase (RbcS) promoter, a chlorophyll a/b binding-6 (cab6) promoter, a chlorophyll a/b binding-1(Cab-1) promoter, a cab IR promoter from rice, a pyruvate orthophosphate dikinase (PPDK) promoter, a light-harvesting complex of photosystem (Lhcb1*2) promoter, a sucrose-H+ symporter (SUC2) promoter and a thylakoid membrane protein promoter.

In some embodiments, the constitutive promoter is selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the regulated promoter is selected from the group consisting of a stress induced promoter, a chemical-induced promoter, a light induced promoter, a dark-induced promoter, and a circadian-clock controlled promoter.

In some embodiments, the disclosure is directed to a method for improving drought and heat tolerance in a plant or plant cell, comprising introducing the expression vector comprising a nucleotide sequence operably linked to a regulatory region that is functional in a plant or plant cell, wherein the nucleotide sequence encodes a HSP selected from the group consisting of HSP40, HSP60, HSP70, and a PEPC comprising an aspartic acid (D) at a position corresponding to position 509 of SEQ ID NO: 4 into a plant or plant cell, and expressing the nucleic acid in plant or plant cell.

In some embodiments, the disclosure is directed to a plant or plant cell comprising the expression vector comprising a nucleotide sequence operably linked to a regulatory region that is functional in a plant or plant cell, wherein the nucleotide sequence encodes a HSP selected from the group consisting of HSP40, HSP60, HSP70, and a PEPC comprising an aspartic acid (D) at a position corresponding to position 509 of SEQ ID NO: 4.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3D. An overview of CAM pathway in *Kalanchoë fedtschenkoi*. (A) The CAM pathway map in *K. fedtschenkoi*. Orange colors indicate the key enzymes involved in the CAM pathway. The numbers in parenthesis are the four-fold transversion substitution rate (4dtv) values.

(B) Diel expression profiles of duplicated genes in CAM-related gene families. The black and white bars indicate nighttime and daytime, respectively. β-CA: β type carbonic anhydrase; PEP: phosphoenolpyruvate; PEPC: PEP carboxylase; MDH: malate dehydrogenase; PPCK: PEPC kinase; ALMT: tonoplast aluminum-activated malate transporter; TDT: tonoplast dicarboxylate transporter; ME: malic enzyme; PPDK: pyruvate phosphate dikinase. White and black bars indicate daytime (12-hour) and nighttime (12-hour), respectively. (C) List of genes involved in CAM carboxylation process in *Kalanchoë fedtschenkoi*. (D) List of genes involved in CAM decarboxylation process in *Kalanchoë fedtschenkoi*.

FIGS. 4A-4E. Convergent evolution in CAM carboxylation. (A) Regulatory relationship between PPCK1 and PEPC1. (B) The PPCK1 transcript expression in *Kalanchoë* (Kaladp0037s0517), pineapple (Aco013938) and *Arabidopsis* (AT1G08650). (C) Diel expression of PEPC1 and PEPC2 transcripts in *K. fedtschenkoi*, shown in the left and right Y-axis, respectively. (D) Probability of convergent changes in PEPC2 protein sequence between *Kalanchoë* (Kaladp0048s0578) and orchid (PEQU_07008). (E) 3D protein structure of *Kalanchoë* PEPC2. The PEPC2 convergent mutation (D509, represented by red spheres) is located in an α-helix adjacent to the active center at the β-barrel (red), whereas the phosphorylation site (S8, represented by green spheres) at the N-terminus is located at the other side of PEPC2. PEP: phosphoenolpyuvate; PEPC, PEP carboxylase; PPCK: PEPC kinase; OAA: Oxaloacetate.

Figures 5A, 5B:
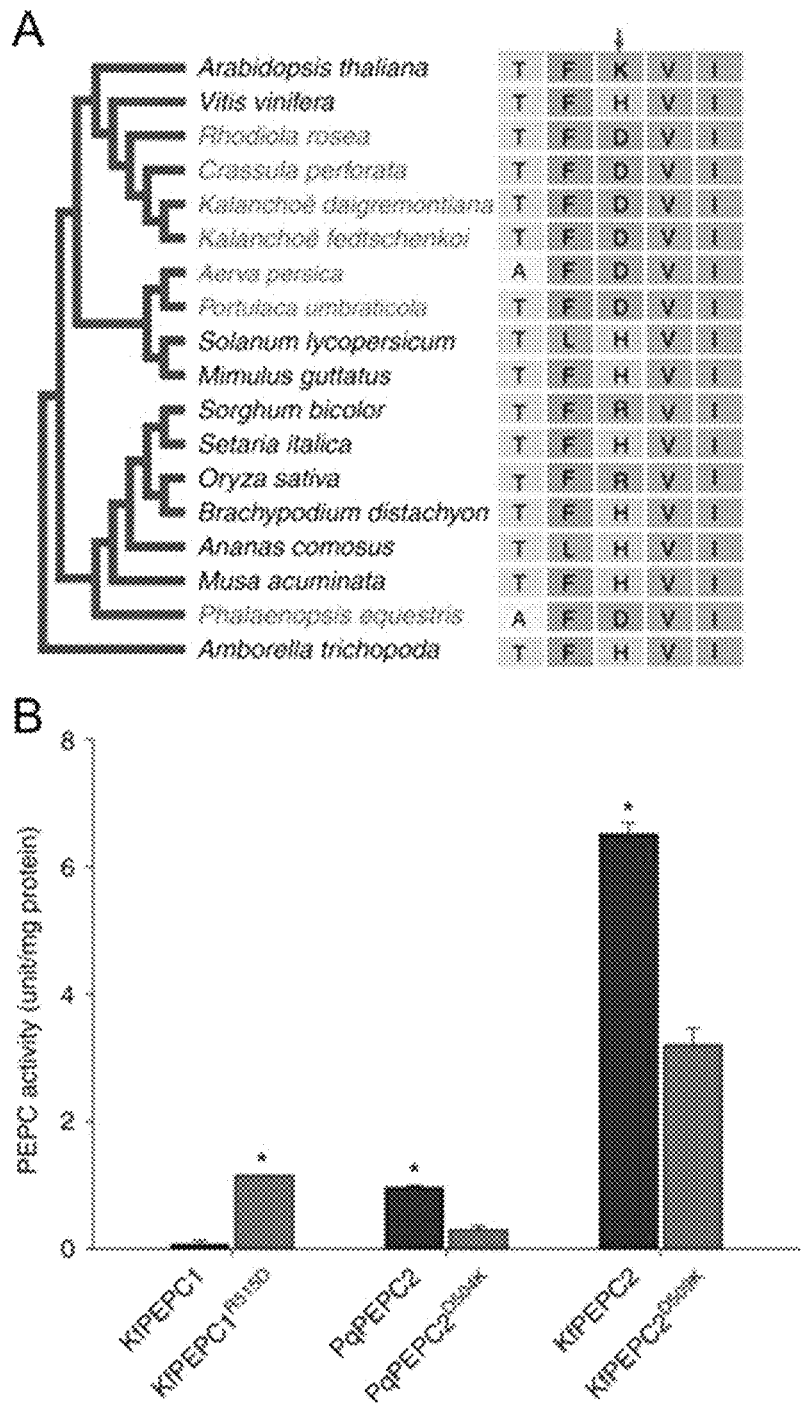

FIGS. 5A-5B. A convergent change in phosphoenolpyruvate carboxylase (PEPC) protein sequences. (A) A convergent amino acid change (from R/K/H to D) in PEPC2 shared by diverse species (highlighted in red font) at the alignment position indicated by the red arrow. (B) In vitro activity of PEPC isoforms in the absence of phosphorylation by PPCK. KfPEPC1: Kaladp0095s0055; KfPEPC1$^{R515D}$: KfPEPC1 with mutation at residue 515 from arginine (R) to aspartic acid (D); KfPEPC2: Kaladp0048s0578.1; KfPEPC2$^{D509K}$: KfPEPC2 with mutation at residue 509 from D to lysine (K); PqPEPC2: *P. equestris* PEPC gene PEQU07008; PqPEPC2$^{D504K}$: PqPEPC2 with mutation at residue 504 from D to K. "*" indicates significant difference between wild-type and mutant of PEPC1 or PEPC2 (Student's t-test; P<0.01). The error bars indicate standard deviation (SD) calculated from three replicates.

Figure 6A:
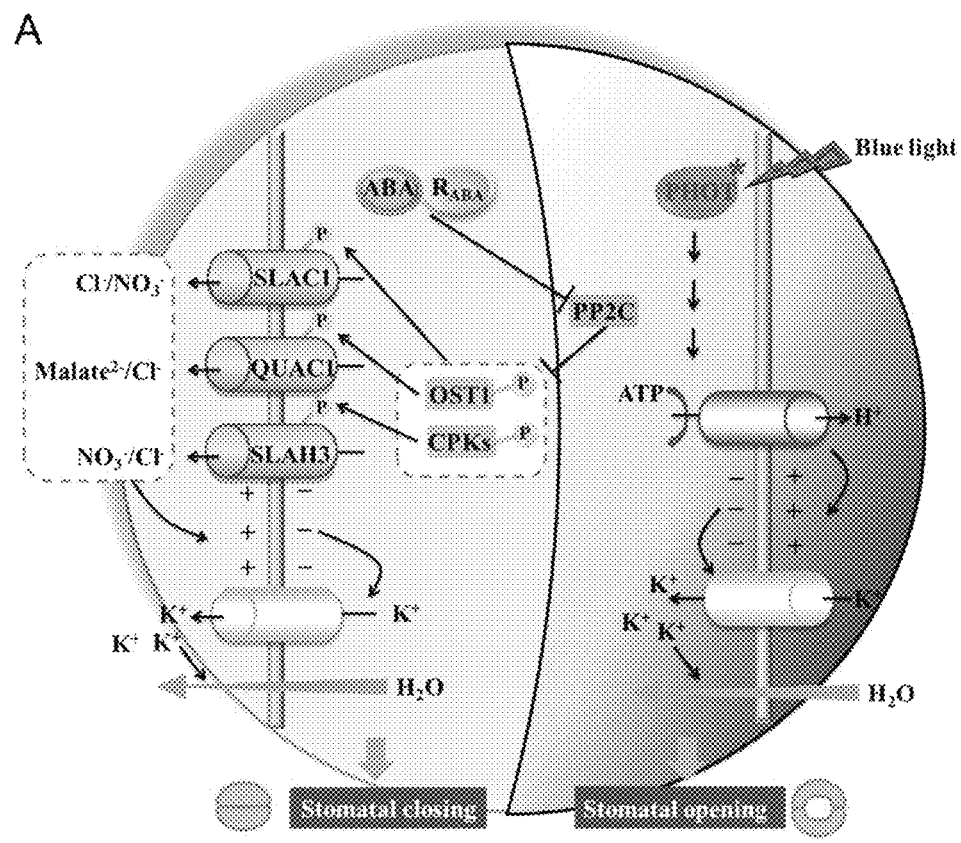
Figure 6B:
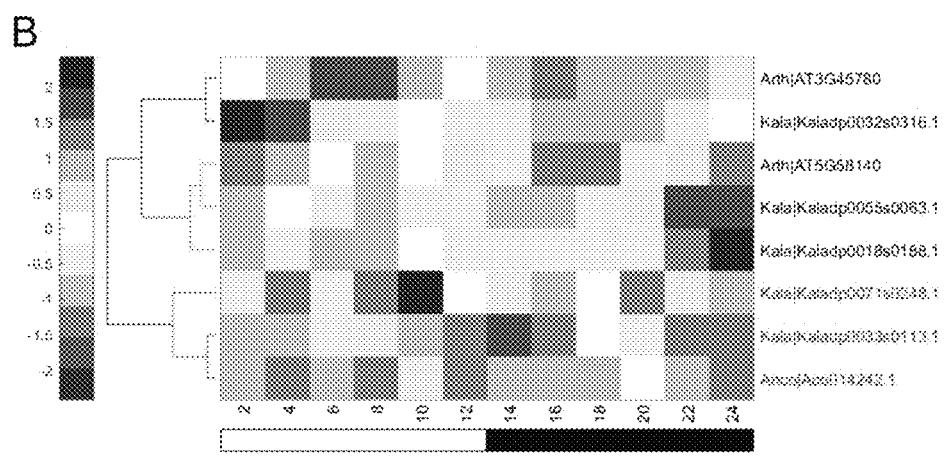

FIGS. 6A-6B. Convergent changes in diel expression of transcripts involved in stomatal movement in *Kalanchoe* and pineapple. (A) An overview of the molecular signaling pathway involved in stomatal movement. (B) The convergent changes in diel expression profiles of PHOT2 transcript in *Kalanchoë* (Kaladp00033s0113) and pineapple (Aco014242) compared to *Arabidopsis* (AT5G58140). The black and white bars indicate nighttime and daytime, respectively. ABA: abscisic acid; $R_{ABA}$: receptors of ABA; PP2C: protein phosphatase 2C; OST1: open stomata 1; CPKs: calcium-dependent protein kinases; SLAC1: slow anion channel-associated 1; QUAC1: quick-activating anion channel 1; SLAH3: SLAC1 homologue 3. PHOT: phototropism.

FIGS. 7A-7D. Convergent evolution of heat shock protein60 (HSP60). (A) Schematic representation of the possible mechanism of HSP60 in regulating the activity of RuBisCo in *Kalanchoë*. (B) HeatMap shows the convergent changes of HSP40 expression pattern in *Kalanchoë* and pineapple comparing to *Arabidopsis*. (C) HeatMap shows the convergent changes of HSP60 expression pattern in *Kalanchoë* and pineapple comparing to *Arabidopsis*. (D) HeatMap shows the convergent changes of HSP70 expression pattern in *Kalanchoë* and pineapple comparing to *Arabidopsis*. The black and white bars indicate nighttime and daytime, respectively. RuBisCo: Ribulose-1,5-bisphosphate carboxylase/oxygenase. RCA: rubisco activase. RuBP: ribulose-1,5-bisphosphate. PGA: 3-phosphoglycerate.

Figure 8A:
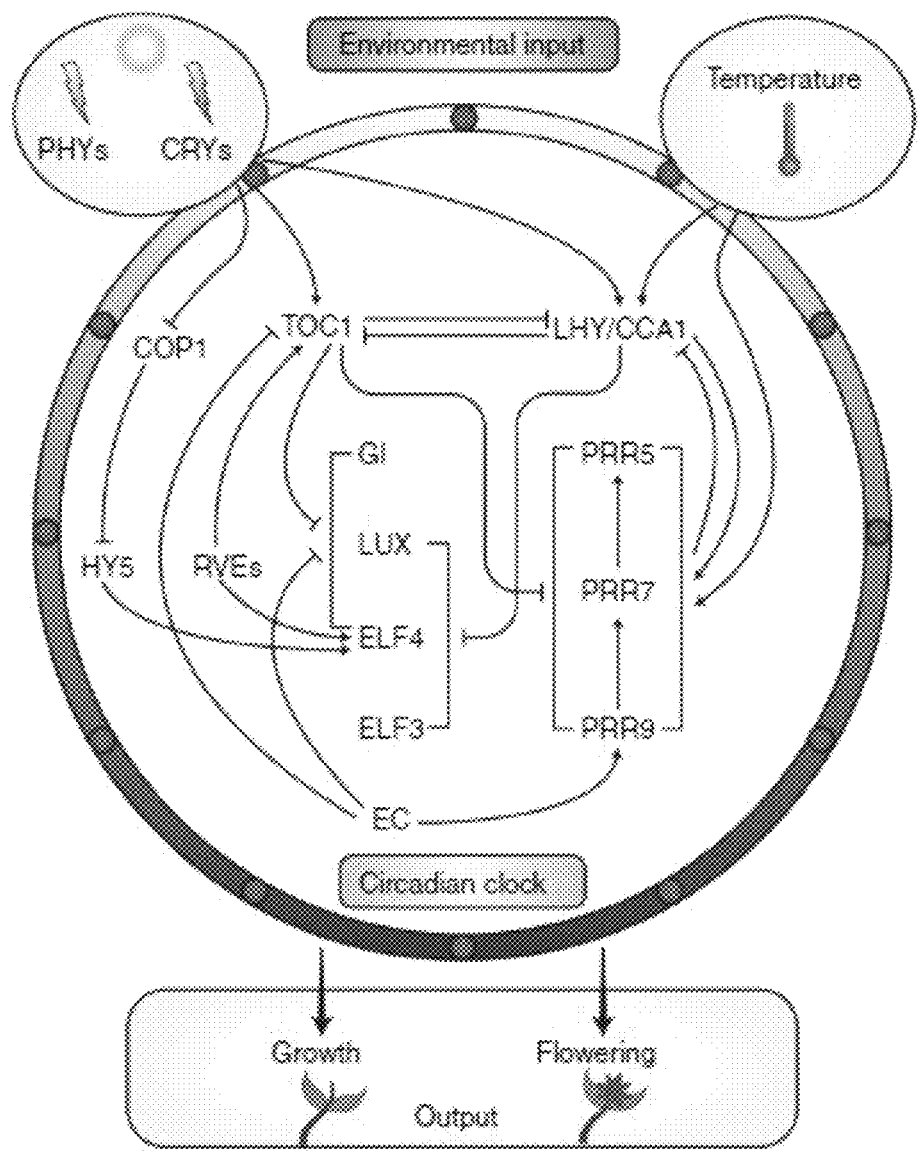
Figure 8B:
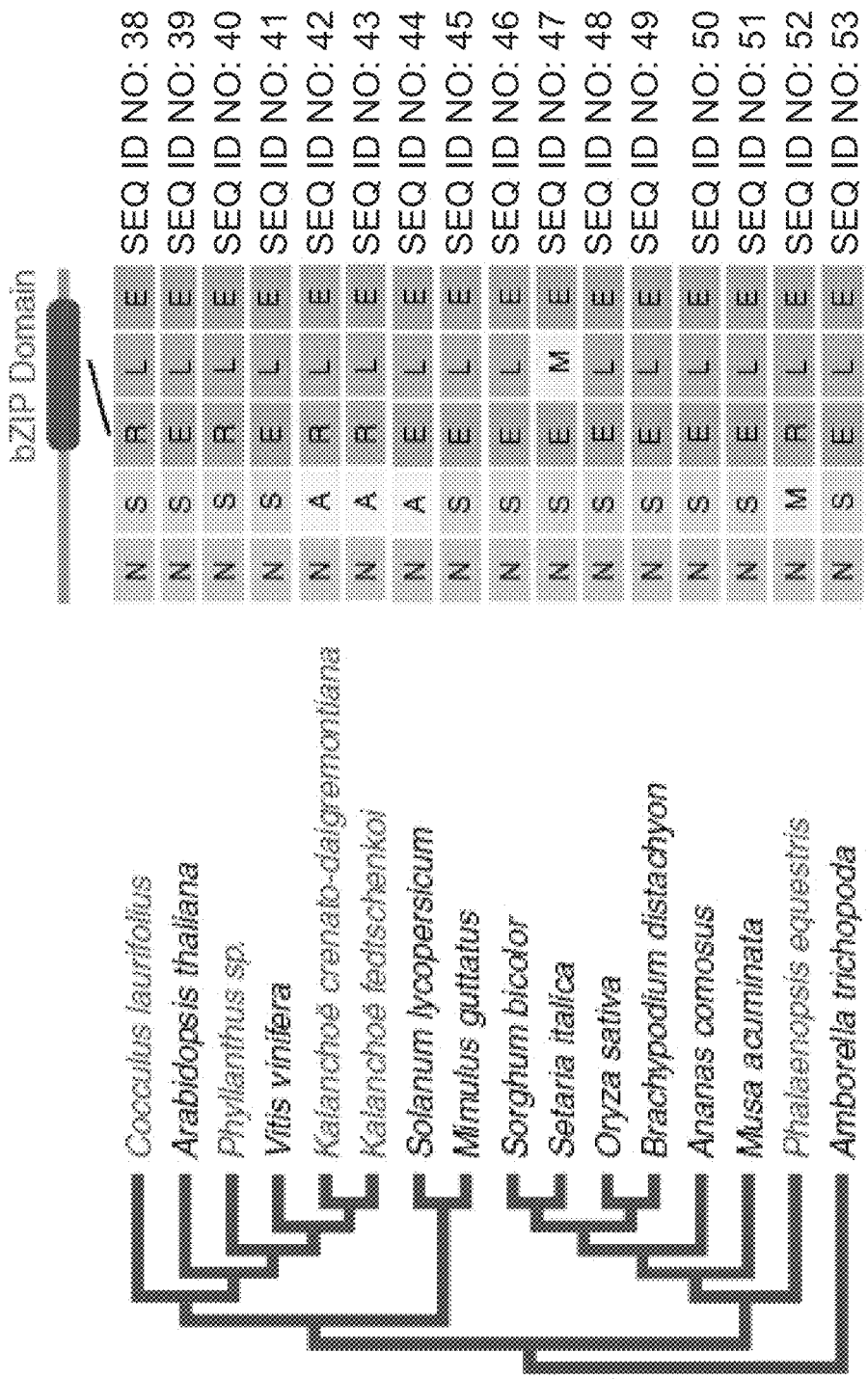

FIGS. 8A-8B. Convergent evolution of elongated hypocotyl 5 (HY5) in *Kalanchoe fedtschenkoi* and orchid. (A) An overview of the signaling pathway involved in circadian rhythm in plants. (B) Convergent change in HY5 protein sequences (highlighted in red in the phylogenetic tree) in *K. fedtschenkoi* and orchid. The black line indicates the protein sequence alignment position showing the convergent change. COP1: constitutive photomorphogenic 1; CCA1: circadian clock associated 1; LHY: late elongated hypocotyl; ELF 3/4: early flowering 3/4; PRR5/7/9: pinoresinol reductase 5/7/9; cry: cryptochrome; phyA/B: phytochrome A/B. TOC1: timing of cab expression 1; GI: gigantea; LUX: lux arrhythmo; RVEs: reveilles; EC: evening complex.

Figure 9B:
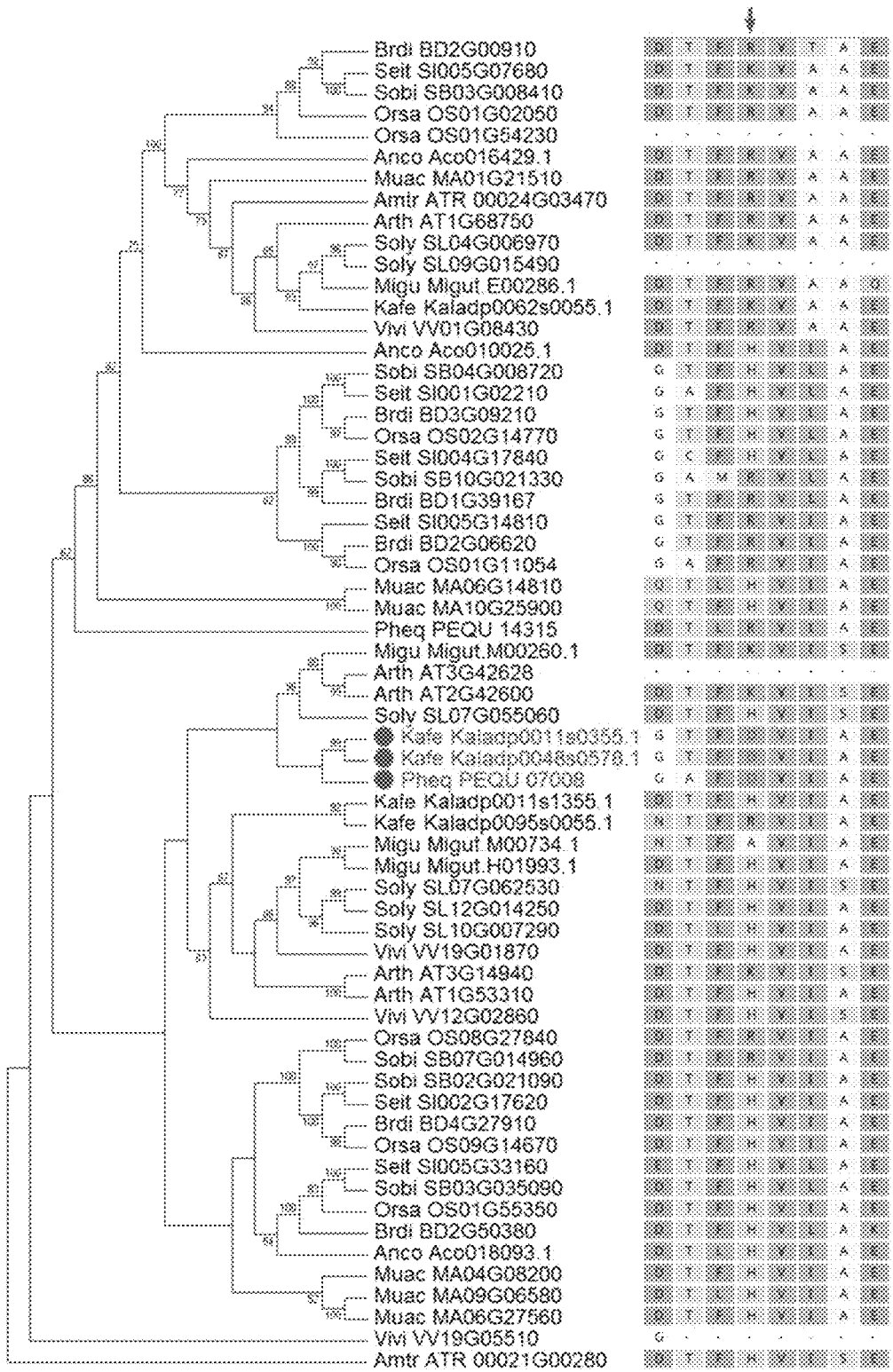

FIG. 9A-9B. Sequence alignments of PEPC proteins from different species. (A) Aligned sequences in order comprise SEQ ID NO:24 (amino acids 489-538 of Kaladp0048s0578.1 (SEQ ID NO:4)), SEQ ID NO:25 (amino acids 489-538 of Kaladp0011s0355.1 (SEQ ID NO:3)), SEQ ID NO:26 (amino acids 489-538 of Kalax.0104s0064.1 (SEQ ID NO:5)), SEQ ID NO:27 (amino acids 489-538 of Kalax.0283s0047.1 (SEQ ID NO:6)), SEQ ID NO:28 (amino acids 489-538 of Kalax.0445s0035.1 (SEQ ID NO:7)), SEQ ID NO:29 (amino acids 489-538 of Kalax.0510s0003.1 (SEQ ID NO:8)), SEQ ID NO:30 (amino acids 489-538 of AAM95946.1 (SEQ ID NO:1)), SEQ ID NO:31 (amino acids 489-538 of XP_020584551.1 (SEQ ID NO:2)), SEQ ID NO:32 amino acids 489-538 of PWZ12751.1 (SEQ ID NO:9), SEQ ID NO:33 (amino acids 489-538 of XP_024436919.1 (SEQ ID NO:10)), SEQ ID NO:34 (amino acids 489-538 of XP_013628861.1 (SEQ ID NO:11)), SEQ ID NO:35 (amino acids 489-538 of XP_009106983.1 (SEQ ID NO:12)), SEQ ID NO:36 (amino acids 489-538 of XP_008362419.1 (SEQ ID NO:13)), SEQ ID NO:37 (amino acids 489-538 of XP_003527347.1 (SEQ ID NO:14)). (B) A maximum-likelihood phylogeny of PEPC gene family. The taxon names in the phylogenetic tree are listed as species abbreviation (the first four letters, see Table 2) followed by gene/transcript name. Red dots highlight the genes showing convergent evolution in protein sequence. The red arrow indicates the protein sequence alignment position where the mutation (H/K/R-to-D) occurred. The sequences in the phylogenetic tree are assigned the following SEQ ID NOs: SEQ ID NO: 54: DTFRVTAE; SEQ ID NO: 55: DTFKVAAE; SEQ ID NO: 56: DTFRVAAE; SEQ ID NO: 57: DTFRVAAQ; SEQ ID NO: 58: DTFHVIAE; SEQ ID NO: 59: GTFHVLAE; SEQ ID NO: 60: GAFHVLAE; SEQ ID NO: 61: GCFHVLAE; SEQ ID NO: 62: GAMRVLAE; SEQ ID NO: 63: GTFRVLAE; SEQ ID NO: 64: GTFRVIAE; SEQ ID NO: 65: GAFRVIAE; SEQ ID NO: 66: QTLHVIAE; SEQ ID NO: 67: QTFHVIAE; SEQ ID NO: 68: DTLRVIAE; SEQ ID NO: 69: DTFKVISE; SEQ ID NO: 70: DTFHVISE; SEQ ID NO: 71: GTFDVIAE; SEQ ID NO: 72: GAFDVIAE; SEQ ID NO: 73: DTFHVIAE; SEQ ID NO: 74: NTFRVIAE; SEQ ID NO: 75: NTFAVIAE; SEQ ID NO: 76: DTFHVIAE; SEQ ID NO: 77: NTFHVISE; SEQ ID NO: 78: DTLHVIAE; SEQ ID NO: 79: DTFKVISE; SEQ ID NO: 80: DTFRVIAE; SEQ ID NO: 81: ETFHV-

LAE; SEQ ID NO: 82: DTFHVLAE; SEQ ID NO: 83: DTFHVLAK; SEQ ID NO: 84: DTFHVIAE.

DETAILED DESCRIPTION OF THE INVENTION

Definitions

Unless defined otherwise, all technical and scientific terms used herein have the same meaning as commonly understood by one of ordinary skill in the art to which this invention belongs.

As used herein, the term "about" refers to an approximately +/−10% variation from a given value. As used herein, the term "CRISPR/Cas" refers to a RNA-guided endonuclease comprising a nuclease, such as Cas9, and a guide RNA that directs cleavage of the DNA by hybridizing to a recognition site in the genomic DNA.

The term "C3 plant" refers to a plant that captures carbon dioxide into three-carbon compounds to enter into the Calvin cycle (photosynthesis pathway). In a C3 plant carbon dioxide capture and the Calvin cycle occur during the daytime, and stomata of C3 plants are open during the day for gas exchange, which also leads to increased water loss through the stomata (evapotranspiration).

The term "C4 plant" refers to a plant that captures carbon dioxide into four-carbon compounds to enter into the Calvin cycle. In a C4 plant carbon dioxide capture and the Calvin cycle occur during the daytime, and stomata of C4 plants are open during the day for gas exchange, which also leads to increased water loss.

The term "Crassulacean Acid Metabolism," also known as CAM, refers to a carbon fixation pathway that evolved in some plants as an adaptation to arid conditions. In a plant using full CAM, the stomata in the leaves remain shut during the day to reduce evapotranspiration, but open at night to collect carbon dioxide ($CO_2$). CAM plants include most succulents, such as cacti and agaves, as well as some orchids and bromeliads. Specific species of CAM plants include *Kalanchoe fedtschenkoi*, *Phalaenopsis equestris*, *Ananas comosus*, and *Crassula perforata*.

The term "control plant," as used herein, refers to a plant of the same species that does not comprise the modification or modifications described in this disclosure. In some embodiments, the control plant is of the same variety. In some embodiments, the control plant is of the same genetic background.

The phrase "a position corresponding to position X of SEQ ID NO: Y" refers to a position that, when the skilled artisan performs a sequence alignment, aligns with position X of SEQ ID NO: Y, wherein X and Y are numbers of the corresponding positions. For instance, "a position corresponding to position 509 of SEQ ID NO: 4" refers to position 505 of SEQ ID NO: 1; position 504 of SEQ ID NO: 2; position 515 of SEQ ID NO: 9; position 514 of SEQ ID NO: 10; position 515 of SEQ ID NO: 11; position 515 of SEQ ID NO: 12; position 508 of SEQ ID NO: 13; position 514 of SEQ ID NO: 14. See FIG. 9A. The skilled artisan can perform a sequence alignment (pair-wise or multiple sequence alignment) between any given at least two sequences, and determine a position corresponding to any given position between the sequences. In some embodiments, the skilled artisan can use a sequence alignment program including, but not limited to, BLAST (NCBI) or ClustalW (EMBL) to perform the sequence alignment.

The term "DNA," as used herein, refers to a nucleic acid molecule of one or more nucleotides in length. By "nucleotide" it is meant a naturally-occurring nucleotide, as well as modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

As used herein, the term "drought stress" or "drought" refers to a sub-optimal environmental condition associated with limited availability of water to a plant. Limited availability of water may occur when, for instance, rain is absent or lower and/or when the plants are watered less frequently than required. Limited water availability to a plant may also occur when for instance water is present in soil, but cannot efficiently be extracted by the plant. For instance, when soils strongly bind water or when the water has a high salt content, it may be more difficult for a plant to extract the water from the soil. Hence, many factors can contribute to result in limited availability of water, i.e. drought, to a plant. The effect of subjecting plants to "drought" or "drought stress" may be that plants do not have optimal growth and/or development. Plants subjected to drought may have wilting signs. For example, plants may be subjected to a period of at least 15 days under specific controlled conditions wherein no water is provided, e.g. without rain fall and/or watering of the plants.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase, and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states. Expression of a gene can be measured through a suitable assay, such as real-time quantitative reverse transcription polymerase chain reaction (qRT-PCR), Northern blot, transcriptome sequencing and Western blot.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically modified" (or "genetically engineered" or "transgenic" or "cisgenic") refers to a plant comprising a manipulated genome or nucleic acids. In some embodiments, the manipulation is the addition of exogenous nucleic acids to the plant. In some embodiments, the manipulation is changing the endogenous genes of the plant.

The term "Heat shock proteins (HSP)" refer to a family of proteins that are produced by cells in response to exposure to stressful conditions. Many members of HSP group perform chaperone function by stabilizing new proteins to ensure correct folding or by helping to refold proteins that were damaged by the cell stress. This increase in expression is transcriptionally regulated. The dramatic upregulation of the heat shock proteins is a key part of the heat shock response and is induced primarily by heat shock factor (HSF).

The term "homologous" refers to nucleic acids or polypeptides that are highly related at the level of nucleotide or amino acid sequence. Nucleic acids or polypeptides that are homologous to each other are termed "homologues." The term "homolog" refers to a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%).

The term "improved drought resistance" (aka. "drought tolerance") refers to plants which, when provided with improved drought resistance, when subjected to drought or drought stress do not show effects or show alleviated effects as observed in control plants not provided with improved drought resistance. A normal plant has some level of drought resistance. It can easily be determined whether a plant has improved drought resistance by comparing a control plant with a plant provided with improved drought resistance under controlled conditions chosen such that in the control plants signs of drought can be observed after a certain period, i.e., when the plants are subjected to drought or drought stress. The plants with improved drought resistance will show less and/or reduced signs of having been subjected to drought, such as wilting, as compared to the control plants. The skilled person knows how to select suitable conditions. When a plant has "improved drought resistance," it is capable of sustaining normal growth and/or normal development when being subjected to drought or drought stress would otherwise have resulted in reduced growth and/or reduced development of normal plants. Hence, "improved drought resistance" is determined by comparing plants, whereby the plant most capable of sustaining (normal) growth under drought stress is a plant with "improved drought resistance." The skilled person is able to select appropriate conditions to determine drought resistance of a plant and how to measure signs of droughts, such as described in for example manuals by the IRRI, Breeding rice for drought prone environments, Fischer et al., 2003; and by the CIMMYT, Breeding for drought and nitrogen stress tolerance in maize: from theory to practice, Banzinger et al, 2000. Examples of methods for determining improved drought resistance in plants are provided in Snow and Tingey (1985, *Plant Physiol*, 77, 602-7) and Harb et al., Analysis of drought stress in *Arabidopsis*, AOP 2010, *Plant Physiology Review*.

The term "improved heat resistance" or "improved heat tolerance" refers to plants which, when provided with heat resistance (or being heat resistant), when subjected to heat stress do not show effects or show alleviated effects as observed in plants not provided with heat resistance. When a plant is "heat resistant," it is capable of sustaining normal growth and/or normal development when being subjected to a high temperature that otherwise would have resulted in reduced growth and/or development in normal plants. Hence, heat resistance is determined by comparing plants with another plant, whereby the plant most capable of sustaining (normal) growth may be a "heat resistant" plant, whereas the plant less capable may be termed a "heat sensitive" plant. Providing heat resistance thus is understood to include improving the heat resistance of a plant, when compared with a plant not provided with heat resistance. With plants provided with heat resistance it is e.g. possible to obtain higher yields of crop and/or plant product when the plant is subjected to a period or periods of heat when compared to plants not provided with heat resistance.

As used herein, the terms "*Kalanchoë laxiflora*" and "*Kalanchoë fedtschenkoi*" refer to the two CAM plant species from the genus *Kalanchoë*.

As used herein, the term "nucleic acid" has its general meaning in the art and refers to refers to a coding or non-coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non-coding region of a genome (i.e. nuclear or mitochondrial or chloroplast).

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell*, 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

GENERAL DESCRIPTION

Plants

There is no specific limitation on the plants that can be used in the methods of the present disclosure, as long as the plant is suitable to be transformed by a gene. The term "plant," as used herein, includes whole plants, plant tissues or plant cells. The plants that can be used for the methods and compositions of the present disclosure include various crops, flower plants or plants of forestry, etc. Specifically, the plants include, but are not limited to, dicotyledon, monocotyledon or gymnosperm. More specifically, the plants include, but is not limited to, wheat, barley, rye, rice, corn, sorghum, beet, apple, pear, plum, peach, apricot, cherry, strawberry, *Rubus swinhoei Hance*, blackberry, bean, lentil, pea, soy, rape, mustard, opium poppy, olea europea, helianthus, coconut, plant producing castor oil, cacao, peanut, calabash, cucumber, watermelon, cotton, flax, cannabis, jute, citrus, lemon, grapefruit, spinach, lettuce, asparagus, cabbage, *Brassica campestris* L. ssp. *Pekinensis*, *Brassica campestris* L. ssp. *chinensis*, carrot, onion, murphy, tomato, green pepper, avocado, cassia, camphor, tobacco, nut, coffee, eggplant, sugar cane, tea, pepper, grapevine, nettle grass, banana, natural rubber tree and ornamental plant, etc.

In some embodiment the methods and compositions of the present disclosure are also be used over a broad range of plant species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus, Oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea*, *Miscanthus* hybrid (*Miscanthus x giganteus*), *Miscanthus sinensis*, *Miscanthus sacchariflorus*, *Panicum virgatum*, *Pennisetum purpureum*, *Phalaris arundinacea*, *Populus* spp including but not limited to *balsamifera, deltoides, tremuloides, tremula, alba* and *maximowiczii*, *Saccharum* spp., *Secale cereale*, *Sorghum almum*, *Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In some embodiments, the plant for the methods and compositions of the present disclosure is a C3 plant. In some embodiment, the C3 plant is selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia* and *Triticum*.

In some embodiments, the plant for the methods and compositions of the present disclosure is a C4 plant. In some embodiment, the C4 plant is selected from the group consisting of genera *Panicum, Saccharum, Setaria, Sorghum* and *Zea*.

Targeted Genome Editing

Targeted genome editing (also known as genome engineering) has emerged as an alternative to classical plant breeding and transgenic (Genetically Modified Organism—GMO) methods to improve crop plants. Available methods for targeted genome editing include the CRISPR/Cas system, zinc finger nucleases (ZFNs), and TAL effector nucleases (TALENs). ZFNs are reviewed in Carroll, D. (*Genetics*, 188.4 (2011): 773-782), and TALENs are reviewed in Zhang et al. (*Plant Physiology*, 161.1 (2013): 20-27), which are incorporated herein in their entirety.

In some embodiments, gene modification is achieved using available gene targeting technologies in the art. Examples of gene targeting technologies include the Cre/Lox system (described in Kuhn, R., & M. Tones, R., *Transgenesis Techniques: Principles and Protocols*, (2002), 175-204.), homologous recombination (described in Capecchi, Mario R., *Science* (1989), 244: 1288-1292), and TALENs (described in Sommer et al., *Chromosome Research* (2015), 23: 43-55, and Cermak et al., *Nucleic Acids Research* (2011): gkr218.).

In some embodiments, gene modification is achieved using a CRISPR/Cas system. CRISPR-Cas and similar gene targeting systems are well known in the art with reagents and protocols readily available (Mali, P. et al., (2013), *Science*, 339(6121), 823-826; Hsu, P. D. et al., (2014), *Cell*, 157.6: 1262-1278.). Exemplary genome editing protocols are described in Jennifer Doudna, and Prashant Mali, "*CRISPR-Cas: A Laboratory Manual*" (2016) (CSHL Press, ISBN: 978-1-621821-30-4) and Ran, F. Ann, et al., *Nature Protocols* (2013), 8 (11): 2281-2308.

A CRISPR-Cas system comprises two components: (1) an RNA-dependent nuclease, typically microbial Cas9 or Cas12 (Cpf1); and (2) a short "guide RNA" (gRNA or sgRNA) comprising a 20-nucleotide targeting sequence that directs the nuclease to a location of interest in the genome. When co-expressed with an artificial sgRNA targeting a cellular gene, the Cas9 endonuclease generates double-stranded breaks of DNA at the targeted locus. In addition, when CRISPR endonuclease is supplemented with a stretch of DNA template homologous to the break region, the break is repaired using the supplied homologous DNA template via the process of homologous recombination (HR). CRISPR-mediated HR makes it possible to specifically edit the target DNA sequence and/or alter gene expression. In some embodiments, sgRNAs and Cas9 are cloned into plasmids and then introduced into plant cells by transfection or transformation.

Methods of Improving Drought and Heat Tolerance in Plants (CAM Engineering)

The inventors of the present disclosure have described a process of improving drought and heat tolerance/resistance in plants called CAM engineering. Drought tolerance/resistance and heat tolerance/resistance are desirable qualities that affect plant biomass. With methods of this disclosure, it is possible to generate plants which produce more biomass, and/or more crop and plant product derived thereof, if grown under conditions of low water availability/drought in comparison with plants not subjected to the method according to the present disclosure. In some embodiments, the biomass of the CAM-engineered plant is increased by at least 5%, by at least 10%, by at least 15%, or by at least 20% when compared to a corresponding control plant.

In some embodiments, drought and heat tolerance of a plant is improved by transforming the plant with a nucleic acid encoding at least one heat shock protein (HSP) selected from the group consisting of HSP40, HSP60 and HSP70. In some embodiments, the introduced nucleic acid encoding at least one HSP is expressed constitutively. In some embodiments, the introduced nucleic acid encoding at least one HSP is expressed in a temporally controlled manner. In a specific embodiment, temporally controlled manner expression of at least one HSP refers to expression of the gene(s) at daytime.

In some embodiments, two HSPs selected from HSP40, HSP60 and HSP70 are expressed simultaneously in a plant. In some embodiments, all the three HSPs (HSP40, HSP60 and HSP70) are expressed simultaneously in a plant.

In some embodiments, the method further comprises expressing a phosphoenolpyruvate carboxylase (PEPC) comprising an aspartic acid (D) at a position corresponding to position 509 of SEQ ID NO: 4. In some embodiments, the PEPC is expressed from the endogenous PEPC gene mutated to comprise an aspartic acid (D) at a position corresponding to position 509 of SEQ ID NO: 4. In some embodiments, the endogenous PEPC gene is mutated using targeted genome editing.

In some embodiments, an exogenous nucleic acid encoding a PEPC comprising an aspartic acid (D) at a position corresponding to position 509 of SEQ ID NO: 4 is introduced to the plant that also expresses an exogenous nucleic acid encoding for at least one of HSP40, HSP60 and HSP70. In some embodiments, the exogenous nucleic acid encodes a PEPC gene of a CAM plant species. In a specific embodiment, the CAM plant species is selected from the group consisting of *Kalanchoe fedtschenkoi, Phalaenopsis equestris* and *Ananas comosus*.

In some embodiments, the PEPC comprising an aspartic acid (D) at a position corresponding to position 509 of SEQ ID NO: 4 is expressed constitutively. In some embodiments, the PEPC comprising an aspartic acid (D) at a position corresponding to position 509 of SEQ ID NO: 4 is expressed in a temporally controlled manner. In a specific embodiment, temporally controlled manner expression of PEPC refers to expression of the PEPC during night time.

In some embodiments a plant, plant cell or plant tissue can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

In some embodiments, the disclosed PEPC mutation is introduced by a CRISPR/Cas system. CRISPR/Cas and similar gene targeting systems are well known in the art with reagents and protocols readily available (Mali, P. et al., (2013), *Science,* 339(6121), 823-826; Hsu, P. D. et al., (2014), *Cell,* 157.6: 1262-1278.). Exemplary genome editing protocols are described in Jennifer Doudna, and Prashant Mali, "*CRISPR-Cas: A Laboratory Manual*" (2016) (CSHL Press, ISBN: 978-1-621821-30-4) and Ran, F. Ann, et al. *Nature Protocols* (2013), 8 (11): 2281-2308.

In some embodiments, modulation of the endogenous PEPC gene is achieved by site-directed mutagenesis to create mutant gene with altered gene expression. Site-directed mutagenesis is described in *Molecular Cloning,* 3rd Ed., *Current Protocols in Molecular Biology*, and U.S. patent application Ser. No. 12/442,143

Expression Vectors

The polynucleotides and expression vectors described herein can be used to increase the expressions of heat shock proteins (HSPs) HSP40, HSP60, HSP70, and phosphoenolpyruvate carboxylase (PEPC) comprising an aspartic acid (D) at a position corresponding to position 509 of SEQ ID NO: 4, in plants and render them drought and heat resistant.

In some embodiments, the vector comprises a nucleic acid sequence encoding for at least one of HSP40, HSP60, HSP70 genes, or a PEPC comprising an aspartic acid (D) at a position corresponding to position 509 of SEQ ID NO: 4. In some embodiments, the PEPC is from a CAM plant species. In a specific embodiment, the CAM plant species is selected from the group consisting of *Kalanchoe fedtschenkoi, Phalaenopsis equestris* and *Ananas comosus*.

The vectors provided herein can include origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione 5-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

In some embodiments, the promoter to drive expression of genes of interest is a constitutive promoter. In some embodiments the constitutive promoter is selected from the group consisting of a ubiquitin promoter, a cauliflower mosaic virus (CaMV) 35S promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the promoter to drive expression of genes of interest is a regulated promoter. In some embodiments the regulated promoter is selected from the group consisting of a stress induced promoter, chemical-induced promoter, a light induced promoter, a dark-induced promoter, and a circadian-clock controlled promoter.

Some suitable regulatory regions initiate transcription, only or predominantly, in certain cell types. For instance, promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine chlorophyll a/b binding-6 (cab6) promoter (Yamamoto et al., *Plant Cell Physiol.*, 35:773-778 (1994)), the chlorophyll a/b binding-1 (Cab-1) promoter from wheat (Fejes et al., *Plant Mol. Biol.*, 15:921-932 (1990)), the chlorophyll a/b binding-1 (CAB-1) promoter from spinach (Lubberstedt et al., *Plant Physiol.*, 104:997-1006 (1994)), the cab IR promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco light-harvesting complex of photosystem (Lhcb1*2) promoter (Cerdan et al., *Plant Mol. Biol.*, 33:245-255 (1997)), the *Arabidopsis* SUC2 sucrose-H+ symporter promoter (Truernit et al., *Planta*, 196:564-570 (1995)) and thylakoid membrane protein promoters from spinach (psaD, psaF, psaE, PC, FNR, atpC, atpD, cab, rbcS).

In some embodiments, promoters of the instant application comprise inducible promoters. Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a vector, e.g., introns, enhancers, upstream activation regions, transcription terminators and inducible elements. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Techniques for introducing nucleic acids into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., *Plant Cell Rep*. V19:304-310 (2000); Chang and Yang, *Bot. Bull. Acad. Sin.*, V37:35-40 (1996) and Han et al., *Biotechnology in Agriculture and Forestry*, V44:291 (ed. by Y. P. S. Bajaj), Springer-Vernag, (1999).

Genetically Modified (Transgenic) Plants/Plant Species/Plant Cells/Plant Tissues Also disclosed herein are plants and plant cells genetically modified by introduction of the disclosed gene editing constructs and expression vectors to display increased heat and drought resistance.

In some embodiments, the genetically modified plant comprises a plant that is modified to express an exogenous nucleic acid encoding at least one heat shock protein (HSP) selected from the group consisting of HSP40, HSP60 and HSP70, and the plant is further modified to express a phosphoenolpyruvate carboxylase (PEPC) comprising an aspartic acid (D) at a position corresponding to position 509 of SEQ ID NO: 4.

In some embodiments, the HSP40, HSP60 and HSP70 are expressed constitutively in the genetically modified plant. In some embodiments, the HSP40, HSP60 and HSP70 are expressed in the genetically-modified plant in a temporally controlled manner. In a specific embodiment, the temporally controlled manner comprises expression of the HSP40, HSP60 and HSP70 during the daytime.

In some embodiments, the PEPC gene is the endogenous gene of the genetically modified plant, and the endogenous PEPC gene is mutated at the position corresponding to position 509 of SEQ ID NO: 4 using the genome editing techniques described above (e.g., one of CRISPR/Cas system, Cre/Lox system, TALEN system, ZFNs system and homologous recombination). In a specific embodiment, the PEPC mutation at the position corresponding to position 509 of SEQ ID NO: 4 is an arginine (R) to aspartic acid (D) mutation. In a specific embodiment, the PEPC mutation at the position corresponding to position 509 of SEQ ID NO: 4 is a histidine (H) to aspartic acid (D) mutation. In a specific embodiment, the PEPC mutation at the position corresponding to position 509 of SEQ ID NO: 4 is a lysine (K) to aspartic acid (D) mutation.

In some embodiments, the genetically-modified plant comprises an exogenous nucleic acid encoding a PEPC gene comprising an aspartic acid (D) at a position that corresponding to position 509 of SEQ ID NO: 4. In some embodiments, the exogenous nucleic acid encodes a PEPC is from a CAM plant species. In a specific embodiment, the CAM plant species is selected from the group consisting of *Kalanchoe fedtschenkoi, Phalaenopsis equestris, Ananas comosus* and *Crassula perforata*.

In some embodiments, the exogenous PEPC gene is expressed constitutively. In some embodiments, the exogenous PEPC gene is expressed in the genetically modified plant in a temporally controlled manner. In a specific embodiment, the temporally controlled manner comprises expression of the PEPC gene during the nighttime.

In some embodiments a plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

In some embodiments, the transgenic plants express the disclosed genes in a tissue-specific manner. In some embodiments, the genes are expressed from nucleic acid constructs that comprise a cell type or tissue type-preferential promoter. As used herein, a "cell type- or tissue-preferential promoter" refers to a promoter that drives expression preferentially in the target tissue, but may also lead to some expression in other cell types or tissues as well. In a specific embodiment, the disclosed genes are expressed in the leaf tissue.

Initial and immediate application of the disclosed methods can be made in the bioenergy crops *Populus* and switchgrass, but the application can be extended to other bioenergy crops such as corn, other sources of lignocellulosic biomass and other model plants e.g., *Salix, Miscanthus*, rice, wheat, soybean and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, miscanthus, oat, rice, rye, ryegrass, sorghum, sudangrass, sugarcane, sweet corn, switchgrass, turf grasses, timothy and wheat. Gymnosperms such as fir, pine and spruce can also be suitable.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

Example 1

*Kalanchoë* Genome Assembly and Annotation

The diploid *K. fedtschenkoi* (2n=2x=34 chromosomes) genome size was estimated to be ~260 Mb. The *K. fedtschenkoi* genome was assembled from ~70× paired-end reads and ~37× mate-pair reads generated using an Illumina MiSeq platform. The genome assembly consisted of 1,324 scaffolds with a total length of 256 Mb and scaffold N50 of 2.45 Mb, in which the inventors predicted and annotated 30,964 protein-coding genes.

Example 2

The Phylogenetic Placement of *Kalanchoë*

Figures 1A, 1B:
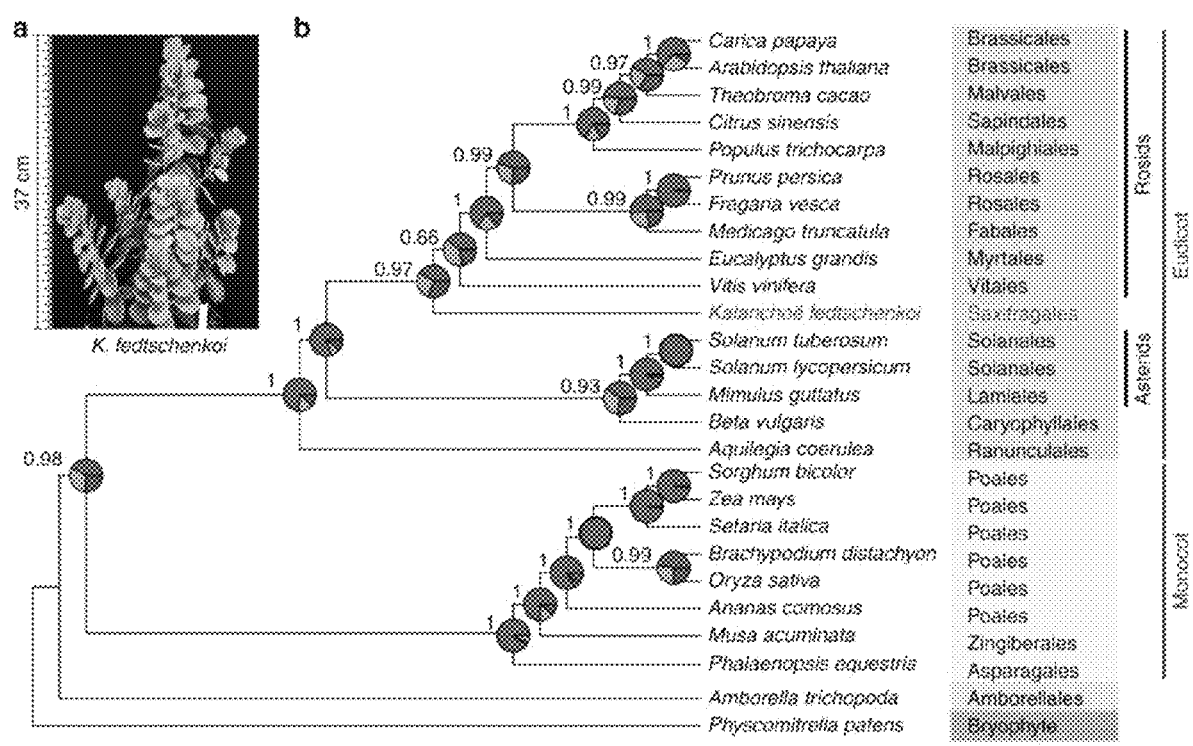
FIGS. 1A-1B. A species tree reconstructed from 210 single copy genes using a summary method. (A) Diploid plant of *Kalanchoë fedtschenkoi*. (B) Individual maximum-likelihood gene trees were reconstructed from the CDS alignments for each of the 210 single-copy-gene ortholog groups using RAxML (Stamatakis, 2006, *Bioinformatics*, 22: 2688-2690), and the species tree was summarized from the gene trees using ASTRAL-II (Mirarab and Warnow, 2015, *Bioinformatics*, 31: i44-i52). Pie graphs on nodes represent the proportion of gene trees that support the various quartets at every node, with red for the main topology shown in this tree, blue for the first alternative and green for the second alternative, respectively. Quartet frequencies displayed in pie graphs and the posterior-probability at each node are calculated by ASTRAL-II (Mirarab and Warnow, 2015, *Bioinformatics*, 31: i44-i52).

*Kalanchoë* is the first eudicot CAM lineage with a genome sequence to date and serves as an important reference for understanding the evolution of CAM. In addition, *K. fedtschenkoi* is the first sequenced species in the distinct eudicot lineage, Saxifragales. Although the monophyly of this morphologically diverse order is well supported by molecular data, its phylogenetic placement has been less clear (Soltis et al., 2013, *American Journal of Botany*, 100: 916-929). The recent consensus view, based mainly on analyses of plastid DNA sequences, has placed the Saxifragales as a sister group to the rosids, and together they comprise the large Glade of superrosids (The Angiosperm Phylogeny Group, 2016, *Botanical Journal of the Linnean Society*, 181: 1-20; Zeng et al., 2017, *New Phytologist*, 214: 1338-1354). However, there have been indications of conflict between trees based on plastid genomes and nuclear genomes for this Glade (Cal et al., 2015, *Nature Genetics*, 47: 65-72; Zeng et al., 2017, *New Phytologist*, 214: 1338-1354). Additionally, the major lineages of core eudicots are thought to have diversified rapidly following their first appearance, making resolution of the relationships among these clades particularly challenging (Moore et al., 2010, *Proc Natl Acad Sci USA*, 107: 4623-4628; Magallon et al., 2015, *New Phytologist*, 207: 437-453) and implicating incomplete lineage sorting (ILS) as a potentially important process that would result in discordance among gene histories (Maddison and Knowles, 2006, *Systematic Biology*, 55: 21-30). Phylogenetic analyses were performed with 210 single-copy nuclear genes from 26 sequenced plant genomes using multiple phylogenetic inference strategies. The resulting species trees are congruent with each other except for the placement of *K. fedtschenkoi*, which was placed either as sister to the rosids in a phylogenetic tree reconstructed using a quartet-based coalescent species tree method (FIG. 1B) or as sister to all other core eudicots as revealed by alternative phylogenetic trees reconstructed from 1) concatenated protein sequence alignment without gene partition using maximum-likelihood, 2) a partitioned analysis of multi-gene alignment using maximum-likelihood and Bayesian methods, and 3) analysis of individual gene trees using fully Bayesian multispecies coalescent method. Despite substantial discordance among estimated nuclear gene trees, the coalescence-based tree was consistent with the results of the plastome-based analyses, placing *Kalanchoë* as sister to the rosids (FIG. 1B). Coalescent species tree estimation can account for gene tree discordance due to ILS (Degnan and Rosenberg, 2009, *Trends in Ecology & Evolution*, 24: 332-340). At the same time, alternative placements of *Kalanchoë* as sister to the asterids, or as sister to all other core eudicots were observed in many gene trees (FIG. 1B). Gene tree discordance due to rapid diversification early in eudicot history has also been characterized by others (Zeng et al., 2017, *New Phytologist*, 214: 1338-1354). Regardless of the optimal placement of the Saxifragales, including *Kalanchoë*, individual gene trees will often have alternative histories due to ILS in the face of rapid species diversification.

Reconstruction of the time-calibrated phylogenetic tree using the BEAST program (Drummond et al., 2012, *Molecular Biology and Evolution*, 29: 1969-1973) based on known fossil records predicts that Kalanchoe diverged from other eudicots c.a. 110 million years ago (Mya). The age estimates in this time-calibrated phylogenetic tree are in general consistent with the fossil records and previous estimates (Bell et al., 2010, *American Journal of Botany*, 97: 1296-1303; Magallon et al., 2015, *New Phytologist*, 207: 437-453). Therefore, the estimated age of the basal angiosperm (*Amborella trichopoda*) is 163 Mya (million years ago), consistent with the original estimation of at least 160 Mya (*Amborella* Genome Project, 2013, *Science*, 342: 1241089). The divergence between the monocot and dicot lineages was estimated to be c.a. 133.3 Mya, consistent with the previous estimation of between ~125 and 142 Mya (Kramer, 2009, *Annual Review of Plant Biology*, 60: 261-277).

Example 3

*Kalanchoë* Genome Duplication

Figures 2A, 2B:
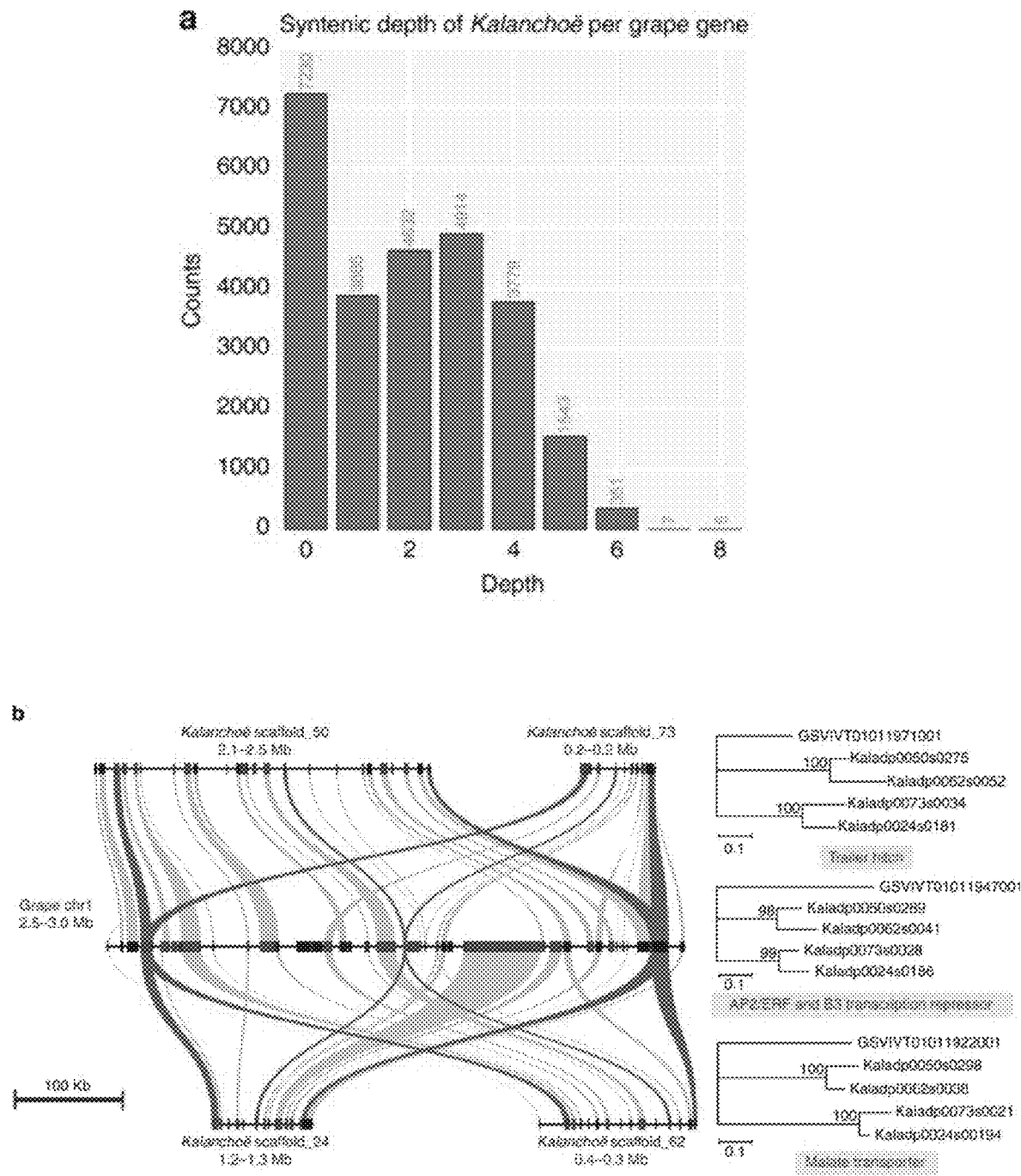
FIGS. 2A-2C. Genome duplication in *Kalanchoë fedtschenkoi*. (A) Syntenic depth of the *K. fedtschenkoi* genome for each grape gene. Syntenic depth refers to the number of times a genomic region is covered by synteny blocks against another genome. (B) Typical micro-colinearity patterns between genomic regions from grape and *K. fedtschenkoi*. Rectangles show predicted gene models with colors showing relative orientations (blue: same strand, green: opposite strand). Matching gene pairs are displayed as connecting shades. Three orthologous gene groups that were maximally retained as four copies in *K. fedtschenkoi* were highlighted with phylogenetic trees on the bottom suggesting two rounds of genome duplications in the *Kalanchoë* lineage. (C) Four-fold transversion substitution rate (4dtv) in *K. fedtschenkoi* and six other eudicot plant species.

The grape genome has no additional genome duplication after the ancestral gamma hexaploidization (Jaillon et al., 2007, *Nature*, 449: 463-467; Murat et al., 2015, *Genome Biology and Evolution*, 7: 735-749) and is the best available reference for studying ancestral eudicot genome duplication events. Syntenic depth analyses (Paterson et al., 2012, *Nature*, 492: 423-427; *Amborella* Genome Project, 2013, *Science*, 342: 1241089) showed that there are multiple *K. fedtschenkoi* blocks covering each grape gene (FIG. 2A). Specifically, 65% of the grape genome had from one to four syntenic blocks in *K. fedtschenkoi*. In contrast, a sudden drop in syntenic depth occurred after a depth of 4× (FIG. 2A), indicating that each grape genome region has up to four *K. fedtschenkoi* blocks and thus providing strong evidence for two distinct whole-genome duplications (WGDs) events in *K. fedtschenkoi*. The microsynteny patterns further support two WGDs on the lineages leading to *K. fedtschenkoi*. Specifically, the microsynteny pattern reflects a 1:4 gene copy ratio between the grape genome and the diploid *K. fedtschenkoi* genome (FIG. 2B). From the *Kalanchoë* point of view, the inventors found that 49% of the *Kalanchoë* genome was covered by one grape-*Kalanchoë* block, 7% covered in two grape-*Kalanchoë* blocks, and 1% covered in three grape-*Kalanchoë* blocks. This suggests that the inventors could often find one best grape-*Kalanchoë* block out of the three gamma triplicated regions in grape. This fits the scenario that the gamma WGD predated the divergence and there has been no WGD in the grape lineage since grape-*Kalanchoë* diverged. Alternatively, if the divergence predated the gamma WGD, then from *Kalanchoë* point of view the inventors should instead see three matching grape regions. Hence, the grape-*Kalanchoë* genome comparisons strongly supported the gamma WGD as a shared event, and further supported the phylogenetic position of *Kalanchoë* in FIG. 1B.

Figure 2C:
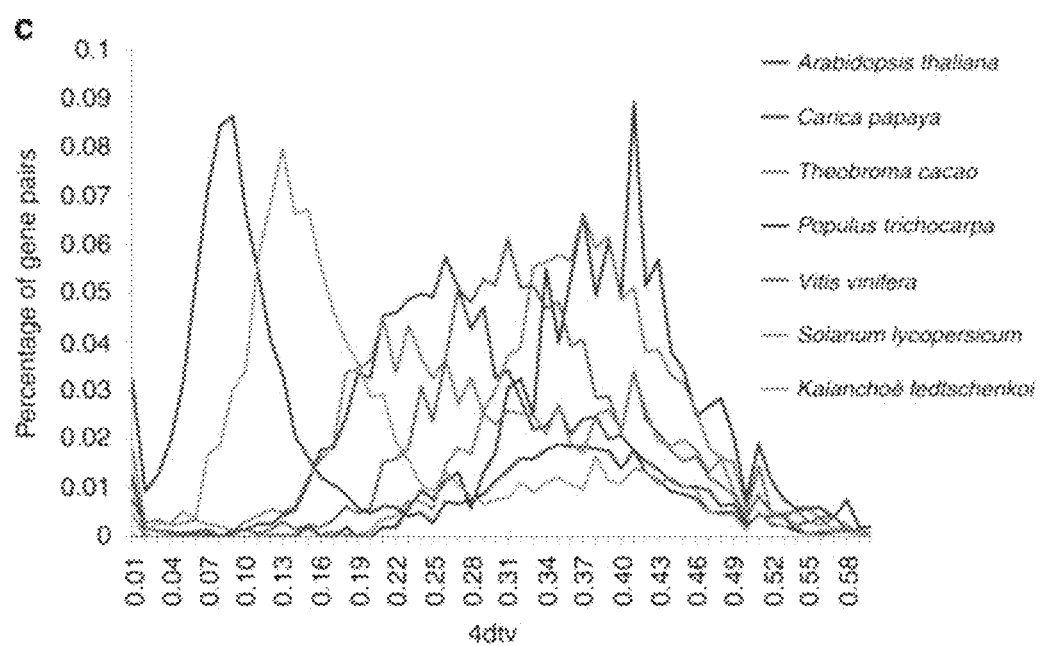

Despite two apparent WGDs in the *K. fedtschenkoi* lineage, synonymous substitutions per synonymous site (Ks) between duplicate gene pairs showed only one prominent peak around 0.35. The unimodal distribution of Ks suggests the two WGD events occurring close in time. Similarly, two distinct peaks appear in the distribution of the four-fold transversion substitution rate (4dtv) values between the *K. fedtschenkoi* gene pairs (FIG. 2C). Grape-*Kalanchoë* gene pairs show a prominent peak around Ks=1.5, indicating that the WGDs in the *K. fedtschenkoi* lineage occurred well after its divergence from grape early in the history of the rosid lineage.

Example 4

CAM Pathway Genes in *K. fedtschenkoi*

Figure 3A:
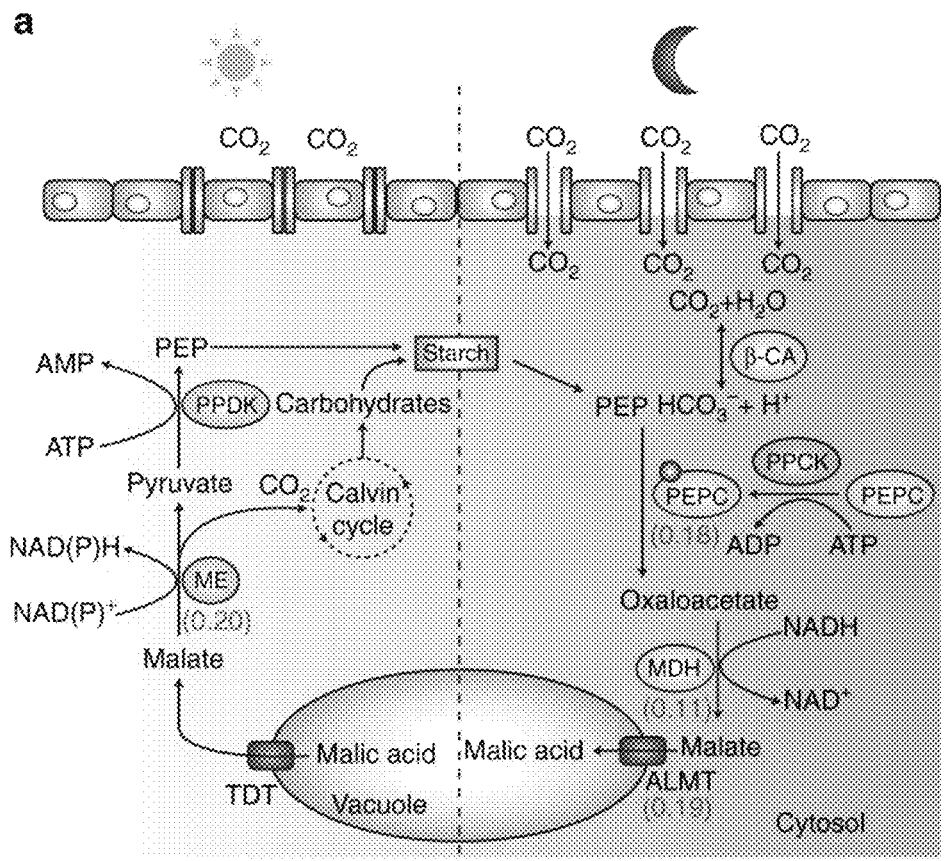

CAM pathway can be divided into two temporally separated processes: carboxylation at night and decarboxylation during the day. There are five enzymes/proteins involved in the carboxylation process, including beta-carbonic anhydrase (β-CA), phosphoenolpyruvate carboxylase (PEPC), phosphoenolpyruvate carboxylase kinase (PPCK), malate dehydrogenase (MDH), and aluminium-activated malate transporter (ALMT); and five enzymes/proteins mediate the decarboxylation process, including ALMT, tonoplast dicarboxylate transporter (TDT), malic enzyme (ME), pyruvate phosphate dikinase (PPDK), and PPDK regulatory protein (PPDK-RP) (FIG. 3A). The genes encoding these enzymes/proteins were identified in *K. fedtschenkoi* (FIG. 3C and FIG. 3D).

There are eight β-CA genes predicted in the *K. fedtschenkoi* genome (Kaladp0095s0400, Kaladp0081s0140, Kaladp0081s0143, Kaladp0034s0051, Kaladp00240122, Kaladp0538s0011, Kaladp0018s0287 and Kaladp0018s0289). Among these β-CA genes, two (i.e., Kaladp0034s0051, Kaladp0018s0289) have relative high transcript abundance compared with the other these β-CA genes in *K. fedtschenkoi*. The transcript expression of Kaladp0034s0051 are relatively higher during the night and early morning, similar the that of its *A. comosus* ortholog Aco005402 that also has relative high transcript abundance compared with the other two paralogs in *A. comosus*. The diel transcript expression of Kaladp0018s0289 is peaked during the mid-night. Since carboxylation occurs at night, it can be suggested that Kaladp0018s0289 would be more relevant to CAM than Kaladp0034s0051.

There are five PEPC genes predicted in the *K. fedtschenkoi* genome (Kaladp0095s0055, Kaladp0048s0578, Kaladp0011s03355, Kaladp0011s1355, and Kaladp0062s0055). Among these PEPC genes, two (i.e., Kaladp0095s0055, Kaladp0048s0578) have relative high transcript abundance compared with the other these PEPC genes in *K. fedtschenkoi*. Kaladp0095s0055 and Kaladp0048s0578 have relatively higher levels of transcript expression during the late afternoon and mid-night, respectively. In *A. comosus*, the relatively highly expression PEPC gene Aco010025 has two transcript expression peaks during the afternoon and mid-night, respectively.

There are seven PPCK genes predicted in the *K. fedtschenkoi* genome (Kaladp0015s0074, Kaladp0076s0015, Kaladp0071s0190, Kaladp0037s0517, Kaladp0050s0014, Kaladp0604s0001, Kaladp0082s0192). Among these PPCK genes, one (i.e., Kaladp0037s0517.1) has relative high transcript abundance compared with the other PPCK genes in *K. fedtschenkoi*, with transcript expression peaking at mid-night, similar to its *A. comosus* ortholog Aco013938 which has the highest level of transcript expression, with a peak at the mid-night, among the four PPCK genes in *A. comosus*.

There are 11 MDH genes predicted in the *K. fedtschenkoi* genome, which can be divided into two groups: MDH1 containing eight genes (Kaladp0101s0211, Kaladp0095s0052, Kaladp0022s0111, Kaladp0001s0257, Kaladp0099s0144, Kaladp0095s0564, Kaladp0048s0189, and Kaladp0058s0569) and MDH2 containing three genes (Kaladp0093s0088, Kaladp0082s0194, and Kaladp1038s0012). Among the *K. fedtschenkoi* MDH1 genes, Kaladp0001s0257 has relative high transcript abundance compared, with transcript expression peaking before dusk and among the five *A. comosus* MDH1 genes, Aco004996 has relative high transcript abundance compared, with transcript expression peaking at mid-night. Both Kaladp0001s0257 and Aco004996 are in the same Glade of the phylogenetic tree. Among the *K. fedtschenkoi* MDH2 genes, Kaladp0082s0194 has relative high transcript abundance compared, with transcript expression peaking in the afternoon and among the five *A. comosus* MDH1 genes, Aco013935 has relative high transcript abundance compared, with transcript expression higher during the night and early morning.

There are five ALMT genes predicted in the *K. fedtschenkoi* genome (Kaladp0073s0021, Kaladp0024s0194, Kaladp0062s0038, Kaladp0048s0850, and Kaladp0050s0298). Among the *K. fedtschenkoi* ALMT genes, three (i.e., Kaladp0073s0021, Kaladp0024s0194, Kaladp0062s0038) have relative higher transcript abundance. The transcript expression of Kaladp0073s0021 and Kaladp0062s0038 peak in the morning and around midnight, respectively. ALMT can transport malate into or out of vacuole (Palmer et al., 2016, *Biochemical Society Transactions*, 44: 856-862). Therefore, the data indicates that Kaladp0062s0038 is involved in the transport of malate into vacuole during the nighttime and Kaladp0073s0021 transports malate out of vacuole during the daytime.

There are two PPDK genes (Kaladp0039s0092 and Kaladp0076s0229) predicted in the *K. fedtschenkoi* genome. Both of them showed higher transcript expression after mid-night till early morning. There are two PPDK regulatory protein (PPDK-RP) genes predicted in the *K. fedtschenkoi* genome, with higher level of transcript expression during the daytime than during the nighttime (FIG. 3E).

There are 13 genes predicted malic enzyme (ME) genes in the *K. fedtschenkoi* genome (Kaladp0092,s0166, Kaladp0045s0427, Kaladp0024s0016, Kaladp0102s0114, Kaladp0098s0037, Kaladp0046s0046, Kaladp0015s0134, Kaladp0472s0027, Kaladp0001s0130, Kaladp0063s0037, Kaladp0089s0116, Kaladp0033s0124, Kaladp0037s0467), including 7 NAD-ME genes and 6 NADP-ME genes. Among the *K. fedtschenkoi* ME genes, Kaladp0092s0166.1 has the highest transcript abundance, with transcript expression peaking in the end of dark-period.

Figure 3B:
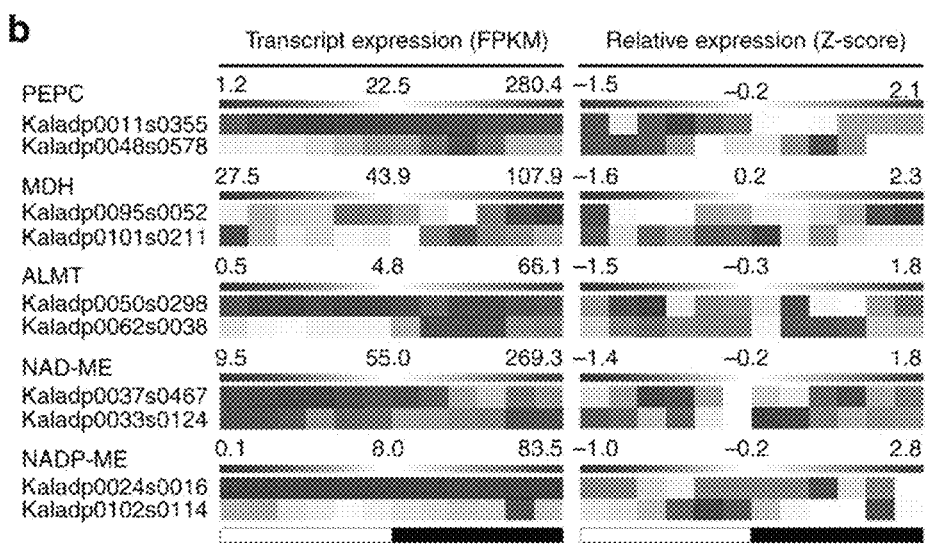

Gene duplication is a major source of genetic novelty (Qian and Zhang, 2014, *Genome Research,* 24: 1356-1362). Most of the genes required for the CAM pathway in *K. fedtschenkoi*, including β-CA, PEPC, MDH, ALMT, NAD-ME and NADP-ME, resulted from recent genome duplication events, with 4DTV values ranging from 0.11-0.20 (FIG. 3A). Furthermore, differences were identified in the transcript abundance between each pair of duplicated CAM genes as well as in the diel expression patterns between the duplicated genes (FIG. 3B). The results suggest that both recent whole genome-duplication and functional diversification in terms of the diel reprogramming of gene expression after gene duplication have contributed to the evolution of CAM genes.

Example 5

Co-Expression Modules in *K. fedtschenkoi*

To elucidate gene function on a global scale in *K. fedtschenkoi*, weighted correlation network analysis were performed of transcript expression in 16 samples including 12 mature leaf samples collected every two hours over a 24-hour period and four non-leaf samples (i.e., shoot-tip, stem, root and flower) collected at one time-point (10:00 am). Network analysis identified 23 co-expression modules, with 408-3,052 genes per module.

Among these, two modules (MEblack containing 782 genes and MEsalmon containing 731 genes) were significantly correlated with the leaf samples collected during the night (dark) period. Several biological processes (e.g., oxylipin metabolic process, carboxylic acid biosynthetic process, terpene biosynthetic process, starch metabolic processes) were over-represented ($p<0.05$) in these two modules. All of the five genes shown for nocturnal CAM carboxylation and vacuolar uptake of malate (FIG. 3A) belong to these two modules: four genes (i.e., PEPC, PPCK, MDH, ALMT) belong to the MEblack module and one gene (β-CA) belongs to the MEsalmon module (FIG. 3C). These results suggest that genes in the co-expression modules MEblack and MEsalmon play important roles in the night-time processes that define CAM. One module (MEblue containing 1911 genes) was positively correlated with the leaf samples collected during the day. Several biological processes (e.g., photosynthesis-light reaction) were over-represented ($p<0.05$) in this module. One gene in the CAM decarboxylation process, PPDK-RP, belongs to MEblue (FIG. 3D).

Example 6

Global View of Genes Involved in Convergent Evolution

Transcript expression pattern (e.g., temporal and spatial expression) and protein sequences are two important characteristics that define the function of protein-encoding genes. It is well known that CAM differs fundamentally from $C_3$ photosynthesis in terms of the diel timing of key metabolic and physiological processes as represented by inverse stomatal behavior and nocturnal $CO_2$ uptake. To examine the possibility that the diel re-programming of metabolism which distinguishes CAM from C3 photosynthesis is achieved by convergent shifts in diel patterns of gene expression, comparative analysis of diel expression pattern in CAM and C3 plant species was performed. Specifically, the diel expression pattern of 9,733 ortholog groups containing genes in *K. fedtschenkoi* (eudicot, CAM photosynthesis), *A. comosus* (monocot, CAM photosynthesis), and *Arabidopsis thaliana* (eudicot, C3 photosynthesis), with transcript expression level greater than 0 FPKM in mature leaf samples collected at five or more time points was performed. A *K. fedtschenkoi* gene is defined to be under convergent evolution in gene expression if its diel transcript expression pattern is highly correlated (Spearman correlation coefficient >0.8) with at least one of the orthologs in *A. comosus* but not highly correlated (Spearman correlation coefficient <0.5) with any of the orthologs in *A. thaliana* (Spearman correlation coefficient <−0.6). As such, 118 *K. fedtschenkoi* genes were identified that were under convergent evolution in gene expression, some of which are key genes in the CAM pathway, such as PPCK1 (Table 1) which plays a key role in carbohydrate processing for CAM (Borland et al, 2016, *Current Opinion in Plant Biology* 31: 118-124). The data suggest that convergence in diel reprogramming of gene expression has contributed to the evolution of CAM plants.

TABLE 1

List of *Kalanchoë* genes showing convergent changes in diel expression pattern

| OrthogroupID | Name | Gene locus | Definition | Gene Expression (FPKM)* |
|---|---|---|---|---|
| ORTHOMCL1004 | PHOT2 | Kaladp0033s0113.1 | Phototropin-2 | 127.13 |
| ORTHOMCL10149 | PPR | Kaladp0058s0382.1 | Pentatricopeptide repeat-containing protein chloroplastic | 2.33 |
| ORTHOMCL10253 | CRS1 Domain | Kaladp0019s0070.1 | Crs2-associated factor mitochondrial | 9.19 |
| ORTHOMCL10493 | DAG | Kaladp0130s0003.1 | Dag chloroplastic-like | 30.83 |
| ORTHOMCL10601 | PPR | Kaladp0071s0438.1 | Pentatricopeptide repeat-containing protein at1g03540 | 1.31 |
| ORTHOMCL1070 | TPX2 | Kaladp0062s0086.1 | Tpx2 family isoform 1 | 56.15 |
| ORTHOMCL10753 | PITHD | Kaladp0022s0180.1 | Pith domain-containing protein at3g04780 | 127.47 |
| ORTHOMCL10798 | MRI1 | Kaladp0053s0416.1 | Methylthioribose-1-phosphate isomerase | 160.46 |
| ORTHOMCL11129 | NUTF2 | Kaladp0040s0332.1 | Nuclear transport factor 2 family protein | 58.75 |
| ORTHOMCL11133 | bcrC | Kaladp0840s0040.1 | Benzoyl-reductase subunit c | 19.37 |
| ORTHOMCL11270 | PPR | Kaladp0098s0206.1 | Pentatricopeptide repeat-containing protein at3g25970 | 1.96 |
| ORTHOMCL11823 | K2P | Kaladp0085s0019.1 | Two-pore potassium channel 5-like | 11.78 |
| ORTHOMCL1282 | | Kaladp0045s0260.1 | Hypothetic protein | 51.44 |
| ORTHOMCL1324 | AKR | Kaladp0039s0606.1 | Ankyrin repeat-containing protein at3g12360 | 61.16 |
| ORTHOMCL1341 | RAP2-7 | Kaladp0101s0311.1 | Ethylene-responsive transcription factor rap2-7 isoform x1 | 8.44 |
| ORTHOMCL152 | PLT1 | Kaladp0040s0745.1 | Polyol transporter 1 | 24.81 |
| ORTHOMCL1541 | SUMO1 | Kaladp0048s0422.1 | Small ubiquitin-related modifier 1 | 47.34 |
| ORTHOMCL1541 | SUMO1 | Kaladp0040s0717.1 | Small ubiquitin-related modifier 1-like | 59.55 |
| ORTHOMCL172 | EXS | Kaladp0008s0539.1 | Leucine-rich repeat receptor protein kinase exs | 11.03 |
| ORTHOMCL18 | HSP70 | Kaladp0101s0179.1 | Heat shock 70 kda protein | 133.82 |
| ORTHOMCL18 | HSP70 | Kaladp0060s0296.1 | Heat shock protein 70 | 545.97 |
| ORTHOMCL2040 | Myb-like DNA-binding domain | Kaladp0040s0719.1 | Hypothetic protein | 8.05 |
| ORTHOMCL207 | CSLC12 | Kaladp0037s0421.1 | Probable xyloglucan glycosyltransferase 12 | 61.71 |
| ORTHOMCL209 | HSP60 | Kaladp0073s0051.1 | Chaperonin-60 beta4 | 33.70 |
| ORTHOMCL212 | PLC2 | Kaladp0059s0034.1 | Phosphoinositide phospholipase c 2-like | 2.43 |
| ORTHOMCL2192 | Lycopene cyclase protein | Kaladp0056s0132.1 | Capsanthin capsorubin chromoplast-like | 38.27 |
| ORTHOMCL2290 | S10 | Kaladp0059s0293.1 | Serine carboxypeptidase s10 family protein | 15.27 |
| ORTHOMCL2360 | CDKI7 | Kaladp0028s0063.1 | Cyclin-dependent kinase inhibitor 7 | 26.16 |
| ORTHOMCL237 | NPF | Kaladp0033s0087.1 | Protein nrt1 ptr family | 58.82 |
| ORTHOMCL2583 | SCL8 | Kaladp0079s0107.1 | Scarecrow-like protein 8 | 77.23 |
| ORTHOMCL2636 | TIM23 | Kaladp1244s0001.1 | Mitochondrial import inner membrane translocase subunit tim23-1-like | 26.26 |
| ORTHOMCL2693 | TOPOISOMERASE-RELATED PROTEIN | Kaladp0878s0047.1 | Nucleotidyltransferase | 21.02 |
| ORTHOMCL2736 | IAA29 | Kaladp0048s0752.1 | Auxin-responsive protein iaa29-like | 52.37 |
| ORTHOMCL2890 | PRN12 | Kaladp0026s0118.1 | 26s Proteasome Non-ATPase Regulatory Subunit 12 Homolog A-Like | 53.14 |
| ORTHOMCL2927 | PDK | Kaladp0068s0282.1 | Pyruvate dehydrogenase (acetyl-transferring) mitochondrial | 245.97 |

TABLE 1-continued

List of *Kalanchoë* genes showing convergent changes in diel expression pattern

| OrthogroupID | Name | Gene locus | Definition | Gene Expression (FPKM)* |
|---|---|---|---|---|
| ORTHOMCL3262 | OMP | Kaladp0040s0029.1 | Kda chloroplast outer envelope membrane | 53.77 |
| ORTHOMCL3292 | ACIN | Kaladp0024s0457.1 | Apoptotic chromatin condensation inducer in the nucleus | 40.42 |
| ORTHOMCL3462 | TMEM245 | Kaladp0048s0390.1 | Transmembrane protein 245 | 50.98 |
| ORTHOMCL3494 | TMEM184C | Kaladp1262s0005.1 | Transmembrane Protein 184c-Like | 1.68 |
| ORTHOMCL3501 | FLO11 | Kaladp0020s0206.1 | Flocculation protein flo11-like | 56.94 |
| ORTHOMCL3552 | ACLB2 | Kaladp0045s0074.1 | ATP-citrate synthase beta chain protein 2 | 26.41 |
| ORTHOMCL391 | NPH3 family | Kaladp0040s0264.1 | Btb poz domain-containing protein npy2-like | 10.80 |
| ORTHOMCL3911 | ASNA1 | Kaladp0016s0145.1 | ATPase asnal homolog | 33.85 |
| ORTHOMCL399 | RL3 | Kaladp0016s0268.1 | Protein radialis-like 3 | 172.19 |
| ORTHOMCL4030 | | Kaladp0867s0029.1 | Hypothetic protein | 3.32 |
| ORTHOMCL4078 | CYOP | Kaladp0550s0032.1 | Probable cytosolic oligopeptidase a | 19.84 |
| ORTHOMCL4118 | Shikimate kinase | Kaladp0043s0207.1 | Shikimate kinase | 26.17 |
| ORTHOMCL417 | UBC10 | Kaladp0101s0230.1 | Ubiquitin-conjugating enzyme E2 10 | 488.73 |
| ORTHOMCL4199 | Ash2l | Kaladp0045s0419.1 | Set1 ash2 histone methyltransferase complex subunit ash2 | 8.93 |
| ORTHOMCL4207 | WRC | Kaladp0011s0273.1 | Wrc protein | 3.34 |
| ORTHOMCL4450 | NADH dehydrogenase | Kaladp1222s0052.1 | Nadh dehydrogenase | 64.67 |
| ORTHOMCL4486 | SNRPC1 | Kaladp0349s0001.1 | U1 small nuclear ribonucleoprotein c-like | 6.80 |
| ORTHOMCL4489 | CAC | Kaladp0031s0015.1 | Mitochondrial carnitine acylcarnitine carrier-like protein | 134.04 |
| ORTHOMCL4653 | Ras suppressor protein | Kaladp0016s0087.1 | Probable lrr receptor-like serine threonine-protein kinase at4g36180 | 2.46 |
| ORTHOMCL4701 | TPR protein | Kaladp0003s0058.1 | Uncharacterized tpr repeat-containing protein at1g05150-like | 6.24 |
| ORTHOMCL4839 | COL2 | Kaladp0039s0496.1 | Zinc finger protein constans-like 16-like | 11.15 |
| ORTHOMCL4949 | GK | Kaladp0037s0359.1 | Glycerol kinase | 12.91 |
| ORTHOMCL4987 | FH | Kaladp0040s0015.1 | Fumarate hydratase mitochondrial | 43.37 |
| ORTHOMCL505 | PIP1-2 | Kaladp0059s0048.1 | Probable aquaporin pip1-2 | 385.66 |
| ORTHOMCL5121 | GTF3C3 | Kaladp0038s0062.1 | General Transcription Factor 3c Polypeptide 3 Isoform X1 | 27.02 |
| ORTHOMCL5218 | ATP synthase | Kaladp0018s0025.1 | ATP synthase subunit mitochondrial | 115.50 |
| ORTHOMCL5276 | | Kaladp0045s0487.1 | Hypothetic protein | 89.17 |
| ORTHOMCL5405 | | Kaladp0693s0001.1 | Unknown | 58.66 |
| ORTHOMCL5433 | FAD6 | Kaladp0080s0163.1 | Omega-6 fatty acid chloroplastic | 156.55 |
| ORTHOMCL5510 | EMC2 | Kaladp0029s0158.1 | Er membrane protein complex subunit 2 | 29.71 |
| ORTHOMCL581 | Enoyl-CoA hydratase | Kaladp0022s0177.1 | Peroxisomal fatty acid beta-oxidation multifunctional protein aim1 | 115.50 |
| ORTHOMCL5914 | SnRKi | Kaladp0037s0373.1 | Snf1-related kinase interactor | 79.72 |
| ORTHOMCL5929 | TAP46 | Kaladp0057s0011.1 | PP2A regulatory subunit tap46 | 28.34 |
| ORTHOMCL6133 | HAD | Kaladp0071s0244.1 | Hydrolase family protein had-superfamily protein | 7.76 |
| ORTHOMCL6542 | Thylakoid formation protein | Kaladp0039s0027.1 | Protein thylakoid chloroplastic | 154.80 |
| ORTHOMCL6669 | NADH dehydrogenase | Kaladp0058s0228.1 | Nadh dehydrogenase | 79.29 |
| ORTHOMCL6767 | SURE | Kaladp0427s0023.1 | Survival phosphatase nucleotidase | 22.16 |
| ORTHOMCL6853 | EDR2L | Kaladp0098s0203.1 | Protein enhanced disease resistance 2-like | 22.35 |
| ORTHOMCL6879 | CYB2 | Kaladp0035s0007.1 | Probable transmembrane ascorbate ferrireductase 2 | 9.38 |
| ORTHOMCL6945 | MPDU1 | Kaladp0042s0089.1 | Mannose-p-dolichol utilization defect 1 protein homolog 2 | 71.91 |
| ORTHOMCL703 | SEC14 | Kaladp0067s0305.1 | Sec 14p-like phosphatidylinositol transfer family protein isoform 1 | 121.55 |
| ORTHOMCL711 | arsB | Kaladp0055s0359.1 | Transporter arsb | 16.87 |
| ORTHOMCL7242 | EX | Kaladp0081s0145.1 | Protein executer chloroplastic | 21.93 |
| ORTHOMCL7384 | Gdap2 | Kaladp0098s0113.1 | Ganglioside-induced differentiation-associated protein 2 isoform x1 | 296.32 |
| ORTHOMCL7435 | GUCD1 | Kaladp0059s0067.1 | Protein gucd1 isoform x1 | 4.65 |
| ORTHOMCL7548 | FAH | Kaladp0060s0413.1 | Fumarylacetoacetase | 34.53 |
| ORTHOMCL763 | | Kaladp0073s0096.1 | Hypothetic protein | 4.75 |

TABLE 1-continued

List of *Kalanchoë* genes showing convergent changes in diel expression pattern

| OrthogroupID | Name | Gene locus | Definition | Gene Expression (FPKM)* |
|---|---|---|---|---|
| ORTHOMCL8133 | | Kaladp0081s0088.1 | Hypothetic protein | 2.03 |
| ORTHOMCL8180 | UFC1 | Kaladp0095s0421.1 | Ubiquitin-fold modifier-conjugating enzyme 1 | 67.27 |
| ORTHOMCL8317 | UREG | Kaladp0098s0208.1 | Urease accessory protein g | 59.20 |
| ORTHOMCL8378 | Inositol monophosphatase | Kaladp0424s0008.1 | PAP-specific mitochondrial | 4.36 |
| ORTHOMCL84 | ABCG15 | Kaladp0045s0418.1 | ABC transporter g family member 15-like | 1.34 |
| ORTHOMCL865 | | Kaladp0034s0049.1 | Probable polygalacturonase non-catalytic subunit jp650 | 9.91 |
| ORTHOMCL873 | SAG | Kaladp0808s0026.1 | Senescence-associated family protein | 137.56 |
| ORTHOMCL894 | PPCK | Kaladp0037s0517.1 | Phosphoenolpyruvate carboxylase kinase | 1187.84 |
| ORTHOMCL9058 | HSP40 | Kaladp0059s0286.1 | Chaperone protein dnaj 6-like | 64.57 |
| ORTHOMCL9096 | Hydrolase | Kaladp0024s0944.1 | Chloroplastic | 66.65 |
| ORTHOMCL9830 | Starch synthase | Kaladp0055s0317.1 | Starch synthase chloroplastic amyloplastic-like | 218.60 |
| ORTHOMCL9861 | NHLRC2 | Kaladp0630s0038.1 | Nhl domain-containing protein isoform 2 | 18.64 |
| ORTHOMCL10490 | TPR protein | Kaladp0748s0049.1 | Tetratricopeptide repeat-like superfamily protein | 27.04 |
| ORTHOMCL10900 | | Kaladp0089s0068.1 | Pentatricopeptide repeat-containing protein at5g18475 | 5.57 |
| ORTHOMCL1406 | SNRPC | Kaladp0018s0298.1 | U1 small nuclear ribonucleoprotein c-like | 4.44 |
| ORTHOMCL16 | GSO1 | Kaladp0048s0157.1 | Lrr receptor-like serine threonine-protein kinase gso1 | 2.39 |
| ORTHOMCL16 | Leucine rich repeat | Kaladp0042s0211.1 | Serine threonine-protein kinase | 16.91 |
| ORTHOMCL1712 | UPL5 | Kaladp0068s0189.1 | E3 ubiquitin-protein ligase upl5 | 6.84 |
| ORTHOMCL2 | Leucine rich repeat | Kaladp1251s0003.1 | Probable lrr receptor-like serine threonine-protein kinase at3g47570 | 12.41 |
| ORTHOMCL2109 | BAHD1 | Kaladp0068s0220.1 | Bromo-adjacent homology domain-containing family protein | 12.74 |
| ORTHOMCL2724 | | Kaladp0048s0254.1 | Protein time for coffee-like isoform x1 | 55.66 |
| ORTHOMCL2837 | MTERF | Kaladp0051s0101.1 | Mitochondrial transcription termination factor family protein | 3.39 |
| ORTHOMCL350 | POK2 | Kaladp0076s0292.1 | Phragmoplast orienting kinesin 2 | 3.32 |
| ORTHOMCL3738 | CHR5 | Kaladp0011s0810.1 | Protein chromatin remodeling 5 | 2.55 |
| ORTHOMCL4232 | TFIID | Kaladp0515s0126.1 | Transcription initiation factor tfiid subunit 8-like | 1.11 |
| ORTHOMCL447 | HMG-CoA reductase | Kaladp0016s0071.1 | 3-hydroxy-3-methylglutaryl-coenzyme a reductase 1 | 312.90 |
| ORTHOMCL502 | Leucine rich repeat | Kaladp0054s0031.1 | Probable lrr receptor-like serine threonine-protein kinase rlk | 47.59 |
| ORTHOMCL5042 | MSL1 | Kaladp0048s0008.1 | Mechanosensitive ion channel protein mitochondrial-like | 1.92 |
| ORTHOMCL5622 | Metal ion binding | Kaladp0008s0875.1 | Probable bifunctional methylthioribulose-1-phosphate dehydratase enolase-phosphatase e1 1 | 13.57 |
| ORTHOMCL5936 | PDCL3 | Kaladp0131s0027.1 | Phosducin-like protein 3 | 71.08 |
| ORTHOMCL68 | CINV1 | Kaladp0550s0020.1 | Alkaline neutral invertase cinv1-like | 124.47 |
| ORTHOMCL7005 | VTA1 | Kaladp1221s0042.1 | Vacuolar protein sorting-associated protein vta1 homolog | 38.68 |
| ORTHOMCL7027 | Leucine rich repeat | Kaladp0032s0056.1 | Leucine-rich repeat receptor-like tyrosine-protein kinase at2g41820 | 48.17 |
| ORTHOMCL851 | Glycosyl transferase family 8 | Kaladp0058s0478.1 | Udp-glucuronate | 25.66 |
| ORTHOMCL93 | Trehalose-phosphatase | Kaladp0011s0363.1 | Probable-trehalose-phosphate synthase | 8.52 |
| ORTHOMCL949 | | Kaladp0011s0144.1 | Protein s-acyltransferase 24-like | 24.42 |

*The maximum expression level in the in the mature leaf during 24-hour period, as revealed by RNA-seq analysis.

To identify *K. fedtschenkoi* genes under convergent evolution in terms of protein sequence in CAM species, gene families (or tribes) were reconstructed from protein sequences in the 25 species listed in FIG. 1B, except *Aquilegia coerulea*, using the TRIBE-MCL approach (Enright et al., 2002, *Nucleic Acids Research*, 30: 1575-1584). Then phylogenetic trees were created for the genes in all the tribe that contain at least one gene in each of the 13 representative species (Table 2).

TABLE 2

The representative species used in the study.

| Photosynthesis | Species | Abbreviation |
|---|---|---|
| $C_3$ | Amborella trichopoda | Amtr |
| $C_3$ | Arabidopsis thaliana | Arth |
| $C_3$ | Brachypodium distachyon | Brdi |
| $C_3$ | Mirratlus guttatus | Migu |
| $C_3$ | Musa acuminata | Muac |
| $C_3$ | Oryza sativa | Orsa |
| $C_3$ | Solanum lycopersicum | Soly |
| $C_3$ | Vitis vinifera | Vivi |
| $C_4$ | Setaria italica | Seit |
| $C_4$ | Sorghum bicolor | Sobi |
| CAM | Ananas comosus | Anco |
| CAM | Kalanchoe fedtschenkoi | Kala |
| CAM | Phalaenopsis equestris | Pheq |

A *K. fedtschenkoi* gene is defined to be under convergent evolution in protein sequence if meeting the following two criteria: 1) the *K. fedtschenkoi* gene is placed together with gene(s) from at least one of the two monocot CAM species (*A. comosus* and *P. equestris*) in a phylogenetic branch that does not contain any genes from $C_3$ or $C_4$ species; and 2) the *K. fedtschenkoi* gene share at least one amino acid mutation with its ortholog in monocot CAM species, which was not found in the $C_3$ or $C_4$ species. As such, 8 *K. fedtschenkoi* genes showed convergent changes in protein sequences, some of which are key genes in the CAM pathway, such as PEPC (Table 3; FIG. 9B).

TABLE 3

List of *Kalanchoë fedtschenkoi* genes showing convergent changes in protein sequences

| Tribe_id | Name | Gene locus | Definition | Gene Expression (FPKM)* |
|---|---|---|---|---|
| I50_F000324 | CSNK1D | Kaladp0011s0439.1 | casein kinase i isoform delta-like | 142.45 |
| I50_F000807 | PEPC2 | Kaladp0048s0578.1 | phosphoenolpyruvate carboxylase 2 | 280.38 |
| I50_F001102 | NAP1L4 | Kaladp0094s0051.1 | nucleosome assembly protein 1 4-like | 3.40 |
| I50_F001653 | HY5 | Kaladp0060s0460.1 | transcription factor hy5-like protein | 59.76 |
| I50_F002629 | Unknown | Kaladp0099s0123.1 | hypothetical protein POPTR_0009502920g | 17.69 |
| I50_F003030 | HSP40 | Kaladp0845s0002.1 | dnaj homolog subfamily b member 3 | 73.84 |
| I50_F003508 | GPI | Kaladp0095s0394.1 | glucose-6-phosphate isomerase chloroplastic-like | 38.42 |
| I50_F004675 | Rab5ip | Kaladp0032s0337.1 | rab5-interacting family protein | 4.93 |

*The maximum expression level in the in the mature leaf during 24-hour period, as revealed by RNA-seq analysis.

Example 7

Convergent Evolution of Genes Involved in Nocturnal $CO_2$ Fixation

Figures 4A, 4B, 4C, 4D, 4E:
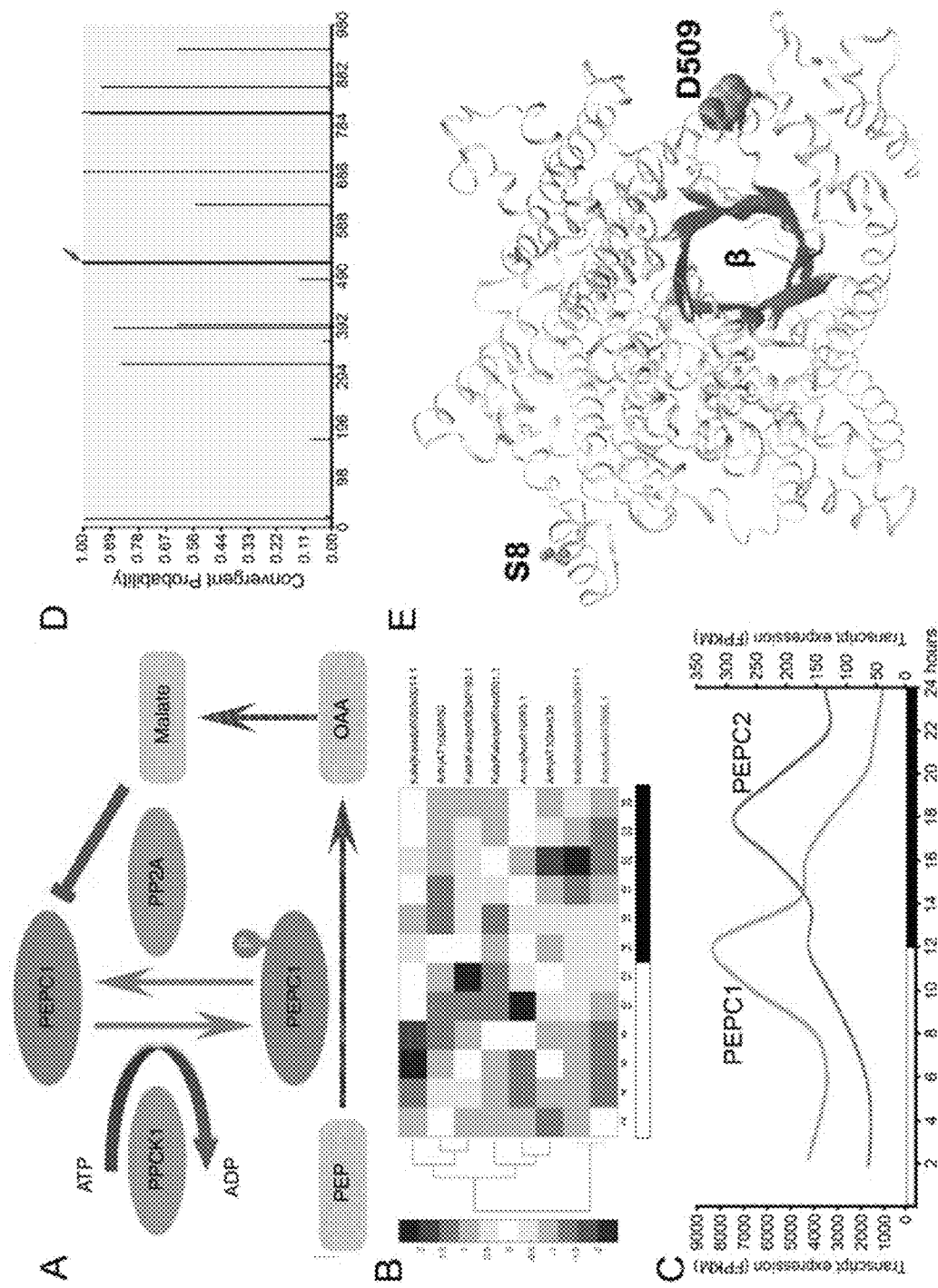

PEPC and PPCK are two key enzymes for nocturnal $CO_2$ fixation in CAM plants (Borland et al., 2014, *Trends in Plant Science*, 19: 327-338; Yang et al., 2015, *New Phytologist*, 207: 491-504). PPCK phosphorylates PEPC (FIG. 4A) and thereby reduces malate inhibition of PEPC, promoting nocturnal $CO_2$ uptake (Hartwell et al., 1999, *Plant Journal*, 20: 333-342; Taybi et al., 2000, *Plant Physiology*, 123: 1471-1482). PPCK is believed to be regulated at the level of transcription (Hartwell et al., 1999, *Plant Journal*, 20: 333-342). The inventors identified four PPCK genes in the *K. fedtschenkoi* genome, among which two (Kaladp0037s0517 and Kaladp0604s0001) showed relatively higher transcript abundance than the others (FIG. 3C). The diel expression pattern of the most abundant PPCK transcripts in *K. fedtschenkoi* (Kaladp0037s0517) and *A. comosus* (Aco013938) were positively correlated (Spearman correlation coefficient of 0.91) whereas both of them were negatively correlated (Spearman correlation coefficient <−0.67) with their *Arabidopsis* ortholog (AT1G08650). This convergent change in PPCK transcription shifted its peak transcript abundance from the daytime in $C_3$ species (*Arabidopsis*) to the nighttime in the two CAM species (FIG. 4B), which is consistent with the role of PPCK in activating PEPC-mediated nocturnal C fixation. Five PEPC genes were identified in *K. fedtschenkoi*, among which two (Kaladp0095s0055 and Kaladp0048s0578) showed relatively higher transcript abundance than the others (FIG. 3C). The most abundant PEPC transcripts in *K. fedtschenkoi* (Kaladp0095s0055) were highly-expressed during both the day and the night with a peak at the transition point from day to night whereas the second most abundant PEPC transcripts in *K. fedtschenkoi* (Kaladp0048s0578) showed much higher expression during the night than during the day (FIG. 4C). The inventors found that a duplicated pair of *K. fedtschenkoi* PEPC genes (Kaladp0048s0578 and Kaladp0011s0355) were placed together with a PEPC gene (PEQU_07008) in *P. equestris* in a unique phylogenetic branch (FIG. 9B). PEQU_07008 was recently reported as the CAM-type PEPC in *P. equestris*, and like Kaladp0048s0578 this PEPC also showed higher transcript expression during the night than during the day (Zhang et al., 2016, *Plant Journal*, 86: 175-185). Furthermore, the inventors' analysis of multiple protein sequence alignment revealed that one amino acid, aspartic acid (D), is conserved in PEQU_07008 and Kaladp0048s0578, along with Kaladp0011s0355 which is duplicated copy of Kaladp0048s0578, and this one amino acid was changed to Arginine (R), Lysine (K) or Histidine (H) in other protein sequences in the PEPC family (FIG. 4D and FIG. 9B). The structural model indicates that the single amino acid mutation (from a basic amino acid R/K/H to acidic amino acid D) in Kaladp0048s0578 is located in an α-helix adjacent to the active site of a β-barrel of PEPC (FIG. 4E). Based on the reversed electrostatic characteristics, it is possible that this mutation could counteract the suppression of PEPC activity by malic acid, leading to a hypothesis that the PEPC encoded by Kaladp0048s0578 is not subject to phosphorylation at the N-terminal serine residue (S8 in Kaladp0048s0578). These results suggest two alternative modes of convergent evolution in nocturnal $CO_2$ fixation: 1) PPCK expression is shifted from daytime to nighttime to activate PEPC1 (the most abundant isoform) as shown in *K. fedtschenkoi* and *A. comosus*; or 2) single amino acid mutation from R/K/H to D maintains the active state of PEPC2 (the second most abundant isoform) without need for phosphorylation, as shown in *K. fedtschenkoi* and *P. equestris*. Furthermore, the inventors found that the protein (PEPC2) encoded by Kaladp0048s0578 possesses a novel property that it has no need for activation by PPCK, and this property could be modified by a single amino acid mutation from D to R, K or H (FIGS. 5A and 5B). In other words, the results indicate that a single amino-acid mutation can significantly modify PEPC activity.

The inventors' evolutionary analyses did not detect convergent evolution in the various decarboxylation genes that were expressed in *Kalanchoë* and pineapple. In Kalanchoe, NAD(P)-ME genes were highly expressed whereas the expression of the PEPCK gene was very low. By contrast, in pineapple the transcript abundance of PEPCK was much higher than that of ME transcripts. These results support the concept that malate decarboxylation in *Kalanchoë* is mediated by ME (Dever et al., 2015, *Plant Physiology*, 167: 44-59) and in pineapple by PEPCK, consistent with previous enzyme activity studies (Holtum et al., 2005, *Functional Plant Biology*, 32: 429-449).

Example 8

Convergent Evolution of Genes Involved in CAM Stomatal Movement

The stomatal pores of plant leaves, situated in the epidermis and surrounded by a pair of guard cells, regulate $CO_2$ uptake for photosynthesis and water loss through transpiration (Shimazaki et al., 2007, *Annual Review of Plant Biology*, 58: 219-247). A unique feature of CAM physiology is the inverted day/night pattern of stomatal movement relative to $C_3$, with stomata opening during the night in CAM and during the day in C3 plants (Borland et al., 2014, *Trends in Plant Science*, 19: 327-338). Blue light is a key environmental signal controlling stomatal opening and the blue light response relies on the photoreceptors phototropin 1 (PHOT1) and phototropin 2 (PHOT2) (Kinoshita et al., 2001, *Nature*, 414: 656-660), recruitment of a 14-3-3 protein to a plasma-membrane $H^+$-ATPase (Kinoshita et al., 2003, *Plant Physiology*, 133: 1453-1463), phosphorylation of its C-terminus, proton extrusion, plasma membrane hyperpolarization, potassium uptake via inward-rectifying $K^+$ channels (Schroeder et al., 1987, *Proceedings of the National Academy of Sciences*, 84: 4108-4112) and subsequent guard-cell swelling (Kinoshita and Shimazaki, 2002, *Plant and Cell Physiology*, 43: 1359-1365) (FIG. 6A). The inventors' gene ontology analysis predicted a list of 21 genes involved in stomatal movement in *K. fedtschenkoi* 4). Among these genes, one gene (i.e., Kaladp0033s0113) that encodes PHOT2 showed convergent change in diel transcript expression pattern (Table 4).

TABLE 4

List of genes involved in stomatal movement in *Kalanchoë fedtschenkoi*

| Name | Arabidopsis_id | Kalanchoe_id | Description | Pearson | Spearman |
| --- | --- | --- | --- | --- | --- |
| ABI1 | AT4G26080 | Kaladp0011s0443.1 | ABA INSENSITIVE 1 | 0.50 | 0.47 |
| ABI2 | AT5G57050 | Kaladp0048s0509.1 | ABA INSENSITIVE 2 | −0.26 | −0.15 |
| AHA2 | AT4G30190 | Kaladp0008s0304.1 | PLASMA MEMBRANE PROTON ATPASE 2 | −0.23 | −0.27 |
| AKT1 | AT2G26650 | Kaladp0055s0506.1 | POTASSIUM TRANSPORTER 1 | −0.29 | −0.34 |
| ALMT9 | AT3G18440 | Kaladp0048s0850.1 | ALUMINUM-ACTIVATED MALATE TRANSPORTER 9 | −0.40 | −0.48 |
| BAK1 | AT4G33430 | Kaladp0043s0196.1 | BRI1-ASSOCIATED RECEPTOR KINASE | 0.02 | 0.03 |
| BLUS1 | AT4G14480 | Kaladp0062s0090.1 | BLUE LIGHT SIGNALING1 | −0.11 | 0.15 |
| CPK23 | AT4G04740 | Kaladp0040s0351.1 | CALCIUM-DEPENDENT PROTEIN KINASE 23 | −0.44 | −0.32 |
| CPK3 | AT4G23650 | Kaladp0042s0341.1 | CALCIUM-DEPENDENT PROTEIN KINASE 3 | −0.09 | −0.22 |
| CPK6 | AT2G17290 | Kaladp0055s0096.1 | CALCIUM-DEPENDENT PROTEIN KINASE 6 | −0.19 | −0.31 |
| HT1 | AT1G62400 | Kaladp0073s0100.1 | HIGH LEAF TEMPERATURE 1 | −0.66 | −0.65 |
| KAT1 | AT5G46240 | Kaladp0008s0789.1 | POTASSIUM CHANNEL IN *ARABIDOPSIS THALIANA* 1 | 0.07 | 0.05 |
| KAT2 | AT4G18290 | Kaladp0840s0007.1 | POTASSIUM CHANNEL IN *ARABIDOPSIS THALIANA* 2 | −0.03 | 0.20 |
| OST1 | AT4G33950 | Kaladp0016s0289.1 | OPEN STOMATA 1 | −0.43 | −0.31 |
| OST2 | AT2G18960 | Kaladp0098s0188.1 | OPEN STOMATA 2 | 0.75 | 0.75 |
| PHOT1 | AT3G45780 | Kaladp0071s0248.2 | PHOTOTROPIN 1 | 0.17 | 0.17 |
| PHOT2 | AT5G58140 | Kaladp0033s0113.1 | PHOTOTROPIN 2 | −0.47 | −0.59 |
| PYL9 | AT1G01360 | Kaladp0008s0082.1 | PYRABACTIN RESISTANCE 1-LIKE 9 | 0.04 | 0.08 |

TABLE 4-continued

List of genes involved in stomatal movement in *Kalanchoë fedtschenkoi*

| Name | Arabidopsis_id | Kalanchoe_id | Description | Pearson | Spearman |
|---|---|---|---|---|---|
| QUAC1 | AT4G17970 | Kaladp0091s0013.1 | QUICK-ACTIVATING ANION CHANNEL 1 | −0.34 | −0.17 |
| SLAC1 | AT1G12480 | Kaladp0050s0214.1 | SLOW ANION CHANNEL-ASSOCIATED 1 | −0.66 | −0.69 |

Specifically, the diel transcript expression pattern of Kaladp0033s0113 is highly correlated (Spearman correlation coefficient=0.85) with that of its *A. comosus* ortholog (Aco014242.1) whereas the transcript expression patterns of these two PHOT2 genes in CAM plants were separated from that of the PHOT2 genes in $C_3$ species *Arabidopsis*, with a shift in the peak of transcript abundance from dawn in $C_3$ species (*Arabidopsis*) to dusk in the two CAM species (FIG. 6B). This convergent change in diel expression suggests that PHOT2 contributes to the inverted day/night pattern of stomatal closure/opening in CAM species.

Example 9

Convergent Evolution of Genes Involved in Heat Tolerance/Protection

Figure 7A:
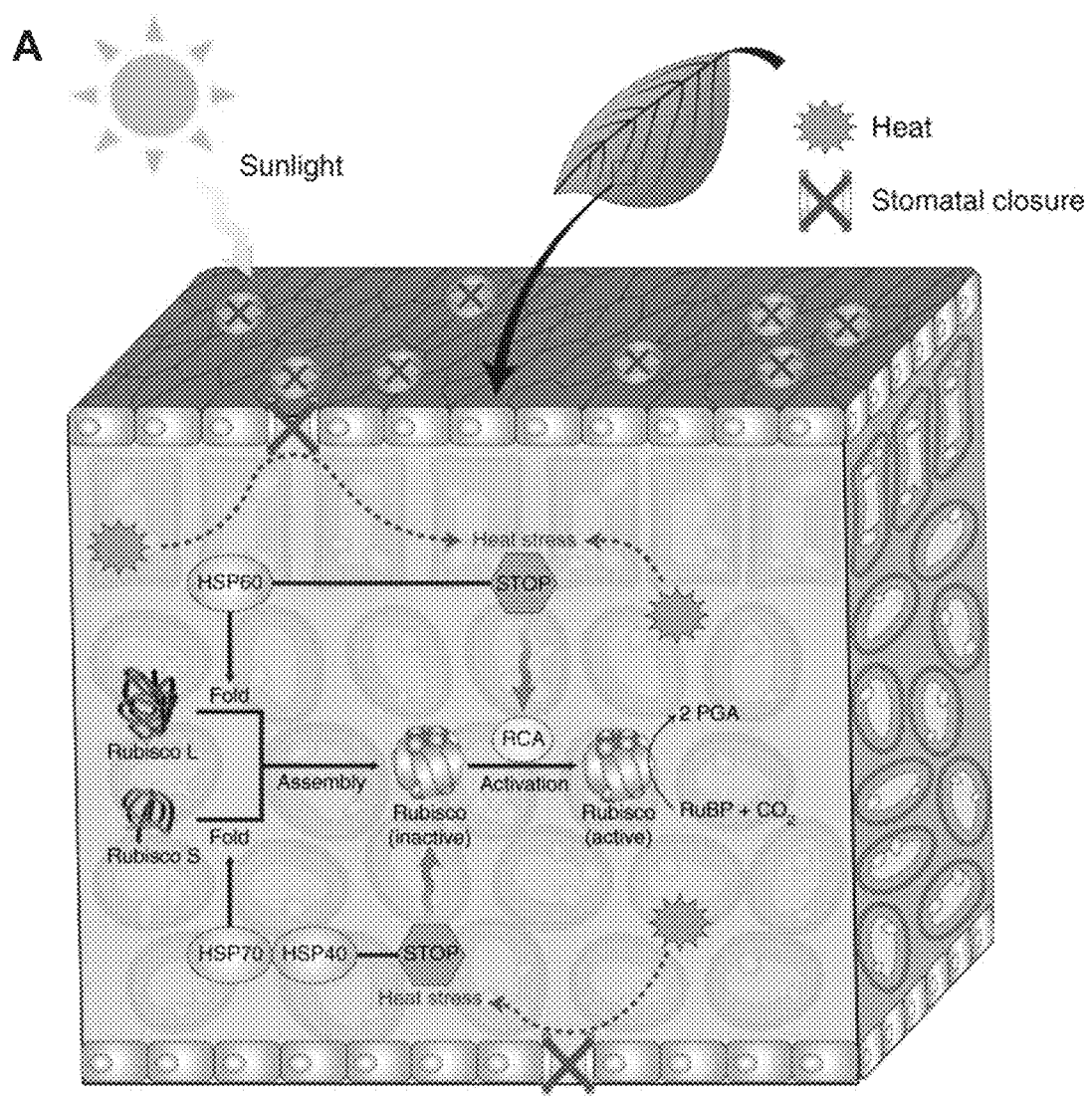
Figure 7B:
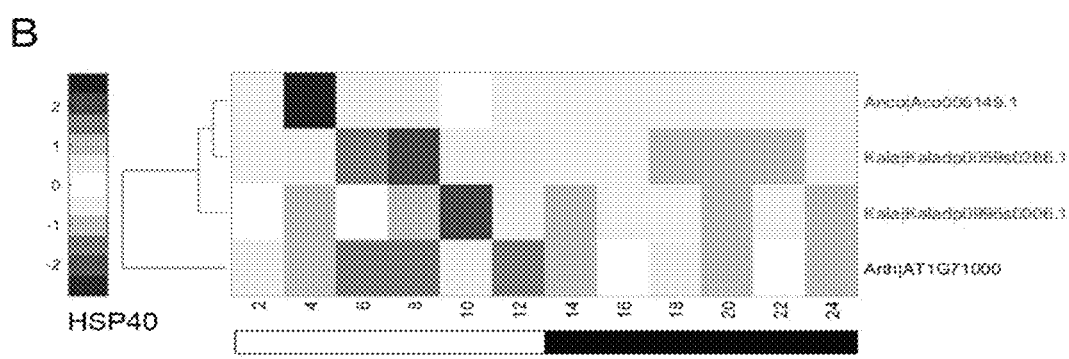
Figure 7C:
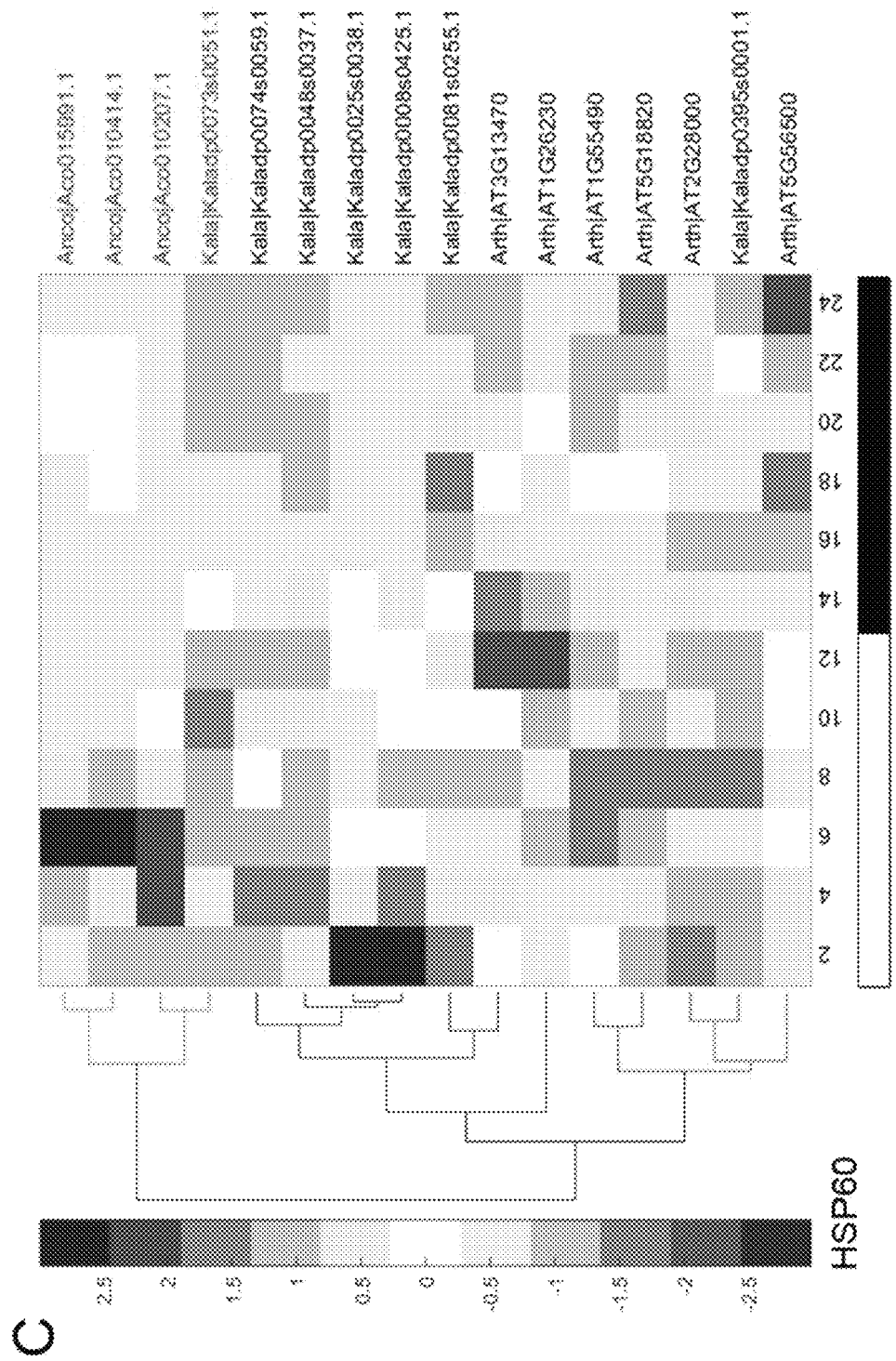
Figure 7D:
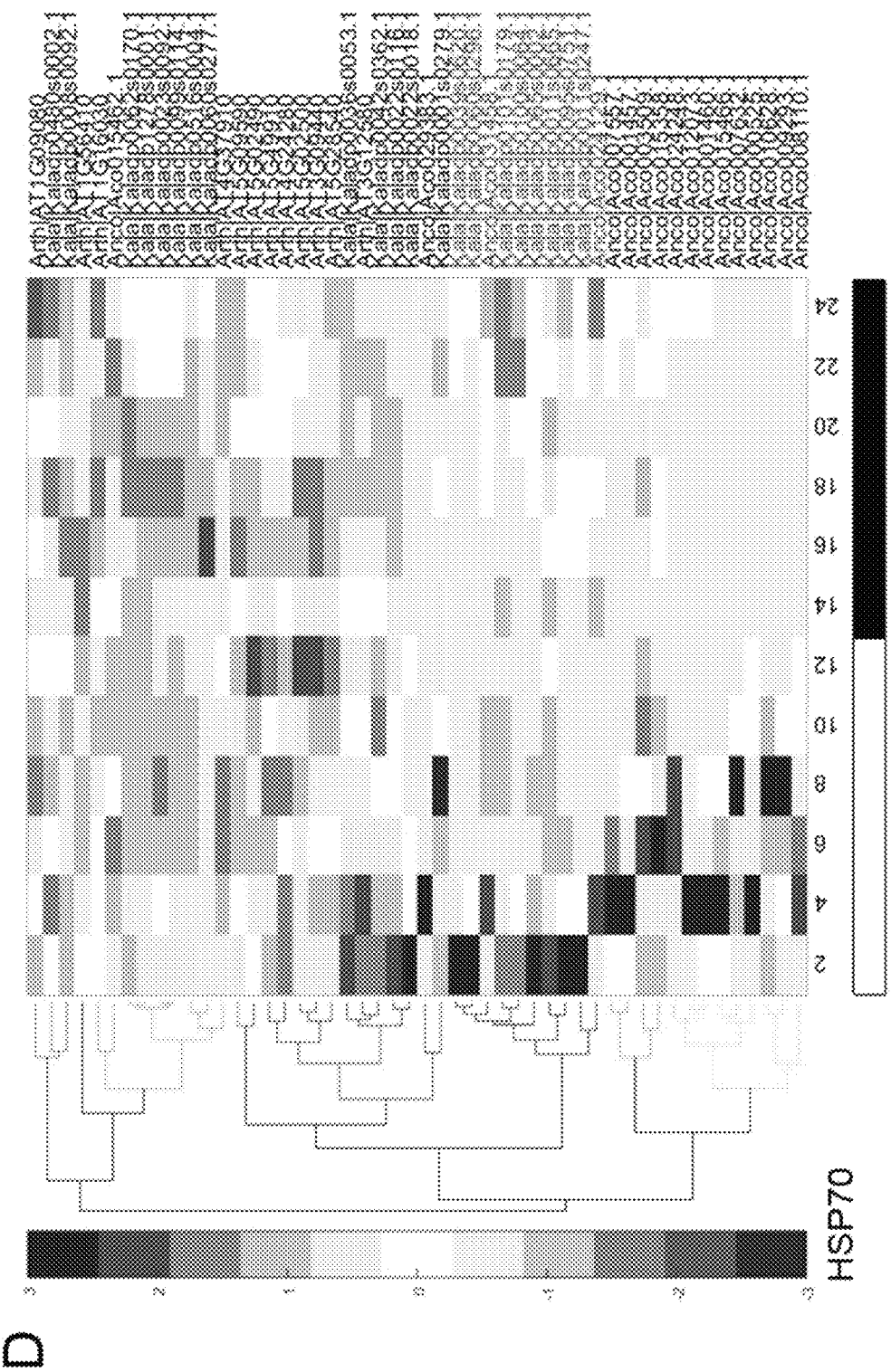

The day-time closure of stomata for much of the day is a defining feature of CAM and can be envisaged to exacerbate internal heat load on the leaves. Photosynthesis is very sensitive to heat stress and can be inhibited long before other symptoms of heat stress are detected (Berry and Bjorkman, 1980, *Annual Review of Plant Physiology*, 31: 491-543; Kobza and Edwards, 1987, *Plant Physiology*, 83: 69-74). Numerous studies have shown that the inhibition of photosynthesis by moderate heat stress is a consequence of ribulose-1,5-bis-phosphate carboxylase/oxygenase (Rubisco) deactivation, caused in part by the thermal instability of Rubisco activase (RCA) (FIG. 7A) (Feller et al., 1998, *Plant Physiology*, 116: 539-546; Salvucci and Crafts☐Brandner, 2004, *Physiologia Plantarum*, 122: 513-519; Kurek et al., 2007, *Plant Cell*, 19: 3230-3241). Wang et al. (2015, *Journal of Experimental Botany*, 66: 3027-3240) reported that S1CDJ2, a heat shock protein 40 (HSP40), contributes to maintenance of $CO_2$ assimilation capacity mainly by protecting Rubisco activity under heat stress, and a HSP70 act as a binding partner of S1CDJ2. Salvucci (2008, *Journal of Experimental Botany*, 59: 1923-1933) found that HSP60 plays an important role in acclimating photosynthesis to heat stress, possibly by protecting Rubisco activase from thermal denaturation (FIG. 7A). The HSP40, HSP60 and HSP70 can also function as nano-compartments for single RbcL/RbcS subunits of Rubisco to fold in isolation, unimpaired by aggregation (Liu et al., 2010, *Nature*, 463: 197-202; Carrier et al., 2011, *American Journal of Botany*, 98: e13-15; Zhang et al., 2016, *Molecular Plant*: DOI: http://dx.doi.org/10.1016/j.molp.2016.1004.1019). Two HSP40 genes were predicted in *K. fedtschenkoi* and the diel transcript expression pattern of one of these two genes (i.e., Kaladp0059s0286) peaks around the noon time and is highly correlated (Spearman correlation coefficient=0.80) with its *A. comosus* ortholog (Aco006149.1) but negatively correlated (Spearman correlation coefficient=−0.28) with its *A. thaliana* ortholog (AT1G71000) (FIG. 7B). Seven HSP60 genes were predicted in *K. fedtschenkoi* and the diel transcript expression pattern of one of these seven genes (i.e., Kaladp0073s0051) peaks around the noon time and is highly correlated (Spearman correlation coefficient=0.83) with its *A. comosus* ortholog (Aco010207.1) but separated from all the orthologs in *A. thaliana* (FIG. 7C). Twenty HSP70 genes were predicted in *K. fedtschenkoi* and the diel transcript expression pattern of one of these genes (i.e., Kaladp0060s0296) peaks in the morning and is highly correlated (Spearman correlation coefficient=0.94) with its *A. comosus* ortholog (Aco031458.1) but separated from all the orthologs in *A. thaliana* (FIG. 7D). These three HSP genes (i.e., Kaladp0059s0286, Kaladp0073s0051, Kaladp0060s0296) that show convent change in transcript expression in the two CAM species (i.e., *K. fedtschenkoi, A. comosus*), with higher transcript abundance during morning or noon time suggest that they could protect the photosynthesis of CAM plants against extreme heat stress during the daytime.

Example 10

Convergent Evolution of Genes Involved in Circadian Rhythm/Clock

Key features of CAM including net $CO_2$ uptake and PEPC phosphorylation are well documented as exhibiting circadian rhythmicity under constant conditions (Rascher et al., 2001, *Proceedings of the National Academy of Sciences*, 98: 11801-11805). The circadian clock has been suggested as a key regulator of the diel reprogramming of metabolism and stomatal function that defines CAM. The molecular basis of circadian rhythms has been extensively studied in non-CAM species (McClung, 2013, *Seminars in Cell & Developmental Biology*, 24: 430-436; Hsu and Harmer, 2014, *Trends in Plant Science*, 19: 240-249). In the *Kalanchoë* genome, 36 genes were predicted to be involved in circadian rhythms, which are divided into four groups: input, clock, output, and other (Table 5).

TABLE 5

List of genes involved in circadian rhythm in *Kalanchoë fedtschenkoi*

| Type | Name | Arabidopsis_id | Kalanchoe_id | Description | Pearson | Spearman |
|---|---|---|---|---|---|---|
| Inputs | COP1 | AT2G32950 | Kaladp0011s0927.1 | CONSTITUTIVE PHOTOMORPHOGENIC 1 | 0.71 | 0.66 |
| Inputs | CRY1 | AT4G08920 | Kaladp0071s0308.1 | CRYPTOCHROME 1 | 0.64 | 0.55 |
| Inputs | CRY2 | AT1G04400 | Kaladp0082s0193.1 | CRYPTOCHROME 2 | 0.15 | 0.10 |

TABLE 5-continued

List of genes involved in circadian rhythm in *Kalanchoë fedtschenkoi*

| Type | Name | Arabidopsis_id | Kalanchoe_id | Description | Pearson | Spearman |
|---|---|---|---|---|---|---|
| Inputs | ELF3 | AT2G25930 | Kaladp0039s0732.1 | EARLY FLOWERING 3 | −0.01 | 0.00 |
| Inputs | FKF1 | AT1G68050 | Kaladp0036s0214.1 | FLAVIN-BINDING, KELCH REPEAT, F BOX 1 | 0.93 | 0.63 |
| Inputs | PHOT1 | AT3G45780 | Kaladp0071s0248.1 | PHOTOTROPIN 1 | −0.31 | −0.44 |
| Inputs | PHOT2 | AT5G58140 | Kaladp0033s0113.1 | PHOTOTROPIN 2 | −0.47 | −0.59 |
| Inputs | PHYA | AT1G09570 | Kaladp0034s0172.1 | PHYTOCHROME A | −0.60 | −0.45 |
| Inputs | PHYB | AT2G18790 | Kaladp0039s0298.1 | PHYTOCHROME B | −0.06 | 0.04 |
| Clock | CCA1 | AT2G46830 | Kaladp0496s0018.2 | CIRCADIAN CLOCK ASSOCIATED 1 | 0.77 | 0.81 |
| Clock | CHE | AT5G08330 | Kaladp0032s0054.1 | CCA1 HIKING EXPEDITION | −0.07 | −0.18 |
| Clock | GI | AT1G22770 | Kaladp0040s0489.1 | GIGANTEA | 0.54 | 0.52 |
| Clock | LUX | AT3G46640 | Kaladp0033s0047.1 | LUX ARRHYTHMO | 0.58 | 0.51 |
| Clock | PIF3 | AT1G09530 | Kaladp0057s0097.1 | PHYTOCHROME INTERACTING FACTOR 3 | −0.65 | −0.90 |
| Clock | PRR3 | AT5G60100 | Kaladp0058s0661.1 | PSEUDO-RESPONSE REGULATOR 3 | 0.16 | 0.22 |
| Clock | PRR5 | AT5G24470 | Kaladp0032s0115.1 | PSEUDO-RESPONSE REGULATOR 5 | 0.79 | 0.48 |
| Clock | PRR7 | AT5G02810 | Kaladp0101s0041.1 | PSEUDO-RESPONSE REGULATOR 7 | 0.66 | 0.69 |
| Clock | PRR9 | AT2G46790 | Kaladp0032s0115.1 | PSEUDO-RESPONSE REGULATOR 9 | 0.33 | 0.28 |
| Clock | TOC1 | AT5G61380 | Kaladp0040s0446.2 | TIMING OF CAB EXPRESSION 1 | 0.97 | 0.96 |
| Clock | ZTL | AT5G57360 | Kaladp0809s0098.1 | ZEITLUPE | 0.68 | 0.47 |
| Outputs | LNK1 | AT5G64170 | Kaladp0607s0046.1 | NIGHT LIGHT-INDUCIBLE AND CLOCK-REGULATED 1 | 0.67 | 0.38 |
| Outputs | LNK2 | AT3G54500 | Kaladp0099s0129.1 | NIGHT LIGHT-INDUCIBLE AND CLOCK-REGULATED 2 | 0.65 | 0.49 |
| Outputs | RVE1 | AT5G17300 | Kaladp0574s0015.1 | REVEILLE 1 | 0.92 | 0.80 |
| Outputs | RVE6 | AT5G52660 | Kaladp0055s0349.1 | REVEILLE 6 | −0.38 | −0.51 |
| Outputs | RVE8 | AT3G09600 | Kaladp0577s0020.1 | REVEILLE 8 | 0.85 | 0.68 |
| Other | CKB4 | AT2G44680 | Kaladp0016s0180.1 | CASEIN KINASE II BETA SUBUNIT 4 | −0.05 | −0.08 |
| Other | ELF4 | AT2G40080 | Kaladp0045s0206.1 | EARLY FLOWERING 4 | 0.44 | 0.57 |
| Other | FIO1 | AT2G21070 | Kaladp0089s0025.1 | FIONA1 | −0.08 | −0.07 |
| Other | HY5 | AT5G11260 | Kaladp0060s0460.1 | ELONGATED HYPOCOTYL 5 | 0.85 | 0.63 |
| Other | JMJD5 | AT5G64813 | Kaladp0076s0198.1 | LIGHT INSENSITIVE PERIOD1 | −0.67 | −0.62 |
| Other | LWD1 | AT1G12910 | Kaladp0048s0797.1 | LIGHT-REGULATED WD 1 | −0.13 | −0.15 |
| Other | PRMT5 | AT4G31120 | Kaladp0056s0075.1 | PROTEIN ARGININE METHYLTRANSFERASE 5 | −0.44 | −0.30 |
| Other | SKIP | AT1G77180 | Kaladp0040s0680.1 | SNW/SKI-INTERACTING PROTEIN | 0.15 | 0.06 |
| Other | STIPL1 | AT1G17070 | Kaladp0071s0383.1 | SPLICEOSOMAL TIMEKEEPER LOCUS1 | 0.59 | 0.60 |
| Other | TEJ | AT2G31870 | Kaladp0040s0530.1 | POLY(ADP-RIBOSE) GLYCOHYDROLASE 1 | 0.66 | 0.69 |

All these *K. fedtschenkoi* genes except Kaladp0033s0113 showed similar diel transcript expression pattern with their orthologs in *A. thaliana* (Table 5). Kaladp0033s0113 encodes PHOT2 that is a member of the input group and was identified to show convergent change in diel transcript expression pattern in two CAM species, as shown in the aforementioned "Stomatal movement" section. Another *K. fedtschenkoi* gene Kaladp0060s0460, which encodes ELONGATED HYPOCOTYL5 (HY5), was found to have convergent change in protein sequence in *K. fedtschenkoi* and *P. equestris* (Table 3). There one amino acid mutation (E-to-R) in the bZIP domain at the at the C-terminus of the proteins encoded by Kaladp0060s0460 and its *P. equestris* ortholog (PEQU_13446) as compared with the HY5 proteins in C3 or C4 species (FIG. 8B). The bZIP domain determines the DNA-binding ability of HY5 as a transcription factor (Nijhawan et al., 2008, *Plant Physiology*, 146: 333-350) and also mediates the interaction between HY5 and GBF1 (Ram and Chattopadhyay, 2013, *Plant Signaling & Behavior*, 8: e22703). HY5 is a transcription factor in the blue light signaling pathway relevant to the regulation of circadian clock (FIG. 8A) (Li et al., 2011, *Nature Cell Biology*, 13: 616-622; Hsu and Harmer, 2014, *Trends in Plant Science*, 19: 240-249). It was recent reported that HY5 could move from shoot to root to coordinate aboveground plant carbon uptake in the leaf and belowground nitrogen acquisition in the root (Chen et al., 2016, *Current Biology*, 26: 640-646). Therefore, it can be postulated that HY5 could play important role in both circadian rhythm and aboveground-to-belowground communication.

Example 11

Convergent Evolution of Genes Involved in Carbohydrate-Active Enzymes

Nocturnal production of PEP as a substrate for dark $CO_2$ uptake represents a substantial sink for carbohydrate in CAM plants which has to be balanced with the provisioning of carbohydrate for growth and maintenance (Borland et al., 2016, *Current Opinion in Plant Biology*, 31: 118-124). The carbohydrate active enzymes (CAZyme) play critical roles in regulating carbohydrate synthesis, metabolism and transport in living organisms. There are six CAZyme classes: glycoside hydrolases (GHs), glycosyltransferases (GTs), polysaccharide lyases (PLs), carbohydrate esterases (CEs), auxiliary activities (AAs), and carbohydrate-binding modules (CBM). Each of the classes contains from a dozen to over a hundred of different protein families classified based on sequence similarity (Lombard et al., 2014, *Nucleic Acids Research*, 42: D490-495). These six classes of CAZymes have different functions. For example, GH enzymes catalyze the hydrolysis of glycosidic bonds while GT enzymes catalyze the formation of glycosidic bonds.

Using CAZyme domain-specific hidden markov models defined in the dbCAN database (Yin et al., 2012, *Nucleic Acids Research*, 40: W445-W451), the inventors identified 103 CAZyme families including 1,134 genes in the *Kalanchoe fedtschenkoi* genome. Among these CAZyme genes, four orthologue groups (i.e., ORTHOMCL68, ORTHOMCL93, ORTHOMCL207, and ORTHOMCL9830), which have genes (such as Kaladp0550s0020.1, Kaladp0011s0363.1, Kaladp0037s0421.1 and Kaladp0055s0317.1) belonging to the CAZyme families GH100, GT20, GT2 and GT5, respectively, were identified to show convergent changes in diel expression pattern in two CAM species (*Kalanchoë fedtschenkoi* and *Ananas comosus*) in comparison with a $C_3$ species (*Arabidopsis thaliana*). Specifically, in orthogroup ORTHOMCL68, the diel transcript expression patterns of five *Kalanchoë* genes (Kaladp0034s0187.1; Kaladp0008s0205.1; Kaladp0550s0020.1; Kaladp0058s0533.1 and Kaladp0003s0101.1) and two pineapple genes (Aco014041.1 and Aco007782.1) clustered together; in orthogroup ORTHOMCL93, the diel transcript expression patterns of two *Kalanchoë* genes (Kaladp0008s0756.1 and Kaladp0011s0363.1) and two pineapple genes (Aco012107.1 and Aco006034.1) clustered together; in orthogroup ORTHOMCL207, the diel transcript expression patterns of one *Kalanchoë* gene (Kaladp0037s0421.1) and two pineapple genes (Aco011603.1 and Aco008242.1) clustered together; and in orthogroup ORTHOMCL9830, the diel transcript expression patterns of one *Kalanchoë* genes (Kaladp0055s0317.1) and one pineapple genes (Aco010848.1) clustered together. Interestingly, the *Kalanchoë* CAZyme genes showing convergent changes in diel expression pattern (e.g., Kaladp0550s0020.1, Kaladp0011s0363.1, Kaladp0037s0421.1 and Kaladp0055s0317.1) showed higher expression at night or early morning. In particular, two genes (Kaladp0011s0363.1 and Kaladp0055s0317.1) were predicted to be involved in starch and sucrose synthesis and metabolism. Kaladp0011s0363 encodes probable trehalose phosphate synthases (TPS). Trehalose 6-P is an important sugar signaling metabolite and is believed to link starch degradation to demand for sucrose and growth (Martins et al., 2013, *Plant Physiology*, 163: 1142-1163). Kaladp0550s0020 encodes alkaline-neutral invertase (A/N Inv) which catalyzes the hydrolysis of sucrose to glucose and fructose, are important regulators of plant growth and development and have been implicated in metabolic signalling processes (Xiang et al., 2011, *Journal of Experimental Botany*: err069). Taken together, the data suggest that the emergence of CAM from C3 photosynthesis required a rescheduling of the transcription of metabolic and signaling genes which are implicated in regulating the partitioning of carbohydrate between reserves set aside to provide substrate for CAM and carbohydrates required for growth.

Example 12

Convergent Evolution of Genes Relevant to Biosynthesis of Secondary Metabolite

Secondary metabolism plays an important role in plant-environmental interactions and plants contain various types of secondary metabolites such as phenylpropanoids, glucosinolates, terpenoids, and phytoalexins/alkaloids (Kliebenstein, 2004, *Plant, Cell & Environment*, 27: 675-684). Among the 118 *K. fedtschenkoi* genes showing convergent changes in diel expression pattern in two CAM species (and *Ananas comosus*) in comparison with a $C_3$ species (*Arabidopsis thaliana*), three genes (i.e., Kaladp0016s0071.1, Kaladp0043s0207.1, Kaladp0022s0177.1) were predicted to be involved in multiple processes of secondary metabolism, including terpenoid backbone biosynthesis, jasmonic acid biosynthesis, and aromatic amino acid biosynthesis via shikimate pathway. Specifically, Kaladp0016s0071.1 encodes 3-hydroxy-3-methylglutaryl-coenzyme a reductase 1 (HMG-CoA reductase) that is a rate-limiting enzyme in the mevalonate (MVA) pathway for terpenoid backbone biosynthesis. Terpenes play a role in plant development and response to abiotic/biotic factors. While CAM species have been previously described as non-emitters of terpenes, the genome of *K. laxifora* revealed the capacity for terpene metabolism with orthologous gene compliments for the precursor mevalonic acid (MVA) pathway and methyl-D-erythritol 4-phosphate (MEP) pathway as well as twenty-nine full-length terpene synthase genes containing the conserved N- and C-terminal terpene synthase Pfam domains (PF01397 and PF03936, respectively). The diel transcript expression profiles of Kaladp0016s0071.1 and its ortholog (Aco18529.1) in *Ananas comosus* were clustered together, separate from that of its ortholog in *Arabidopsis*. Kaladp0016s0071.1 was classified into the co-expression module MEdarkgrey, which was positively correlated with leaf samples collected during the night time from 4:00 am to 6:00 am. Furthermore, five terpene biosynthesis genes (i.e., Kaladp0535s0004.1, Kaladp0010s0015.1, Kaladp1277s0005.1, Kaladp0887s0001.1, Kaladp0095s0367.1) were clustered into the co-expression module MEblack, which was positively correlated with leaf samples collected during the night time from 8:00 pm to 2:00 am. These results suggest that terpene biosynthesis occurs, at least partially, during the night time.

Kaladp0022s0177.1 encodes fatty acid beta-oxidation multifunctional protein AIM1 that is involved in the final biosynthesis step of jasmonic acid, an important regulator of plant development and stress responses (Delker et al., 2007, *Phytochemistry*, 68: 1642-1650). It was classified into the co-expression module MEblack, which was positively correlated with leaf samples collected during the night time from 8:00 pm to 2:00 am. The diel transcript expression profiles of Kaladp0022s0177.1 and its ortholog (Aco010785.1) in *Ananas comosus* were clustered together, separate from that of its ortholog in *Arabidopsis*.

Kaladp0043s0207.1 encodes shikimate kinase that is the fifth enzyme of the shikimate pathway, catalyzes the phosphorylation of the C3 hydroxyl group of shikimate to yield shikimate 3-phosphate, and may provide a regulatory link between the energy-requiring shikimate pathway and cellular energy balance in plants (Maeda and Dudareva, 2012, *Annual Review of Plant Biology*, 63: 73-105). It was classified into the co-expression module MEdarkgrey, which was positively correlated with leaf samples collected during the night time from 4:00 am to 6:00 am. The diel transcript expression profiles of Kaladp0043s0207.1 and its ortholog (Aco001151.1 and Aco002852.1) in *Ananas comosus* were clustered together, separate from that of its ortholog in *Arabidopsis*.

Example 13

*K. fedtschenkoi* features a relatively small genome size (~250 Mb), low repetitive genomic regions (~10%), a unique phylogenetic placement among the sequenced plant species (sister to both rosids and asterids), and easy stable transformation systems. Therefore, with availability of the genome sequence presented in this study, *K. fedtschenkoi* has the potential to become a very useful model for plant evolutionary and comparative genomics research.

It is hypothesized that the monocots and eudicots have diverged from a common ancestor 140-150 million years ago (mya) and the inferred Most Recent Common Ancestor (MRCA) of eudicots has been reconstructed with seven protochromosomes, which went through a paleo-hexaploidization event (then deriving seven ancestral triplicated blocks identified in any modern eudicots) to reach a 21 chromosomes intermediate (Salse, 2016, *Current Opinion in Plant Biology*, 30: 134-142). Accordingly, it can be assumed that the 17 chromosomes in *K. fedtschenkoi* have resulted from an ancient triplication of the 7 protochromosomes in MRCA, with a loss of four chromosomes after the triplication event. However, among the seven eudicot species (i.e., *Arabidopsis thaliana*, *Carica papaya*, *Kalanchoe fedtschenkoi*, *Populus trichocarpa*, *Theobroma cacao*, *Vitis vinifera*, *Solanum lycopersicum*), the ancient whole-genome duplication events are the least clear in *Kalanchoe fedtschenkoi* (FIG. 2). The genome duplication is dominated by two successive rounds of whole-genome-duplication (WGD) events, which are older than the most recent WGD in *P. trichocarpa* but younger than WGDs in other five eudicot species (FIG. 2). These two recent WGD events have impacted the CAM pathways genes in *K. fedtschenkoi* (FIG. 3), providing an excellent opportunity for studying the evolutionary dynamics of duplicated genes.

The genome wide comparison of CAM species vs. non-CAM species by the inventors revealed two types of convergent changes underpinning the CAM evolution: convergent changes in protein sequences and convergent change in diel gene expression patterns. In this study, approximately 130 genes were identified to have experienced convergent evolution in two divergent lineages: eudicot and monocot, providing strong evidence that convergent molecular evolution underpins the CAM phenotype in these phylogenetically distant plant species. CRISPR/Cas9 (Liu et al., 2016, *Current Opinion in Plant Biology*, 30: 70-77) can be used for generating engineered transgenic plants with desirable photosynthesis capabilities.

Convergences can be caused by two basic scenarios: 1) a mutation or mutations in the same gene or genes caused the homoplasy in the organisms; 2) the causal mutation or mutations occurred in different genes in each lineage (Wake et al., 2011, *Science*, 331: 1032-1035; Washburn et al., 2016, *International Journal of Plant Sciences*, 177: 305-318). In this study, the inventors identified 8 genes show convergent changes in protein sequences, of which two genes shared by the three CAM species (i.e., *A. comosus*, *K. fedtschenkoi*, *P. equestris*. This indicates that CAM convergences result mainly from the second scenario (i.e., a mutation or mutations occurred in different genes in each lineage) while the first scenario (i.e., a mutation or mutations in the same gene in each lineage) plays a less important role. *K. fedtschenkoi* shares the convergent mutation in PEPC2 protein sequence with *P. equestris* (FIG. 5) while it shares the convergent change in diel expression pattern of PPCK1 with *A. comosus* (FIG. 4). This result suggests that *K. fedtschenkoi* has two alternative convergent strategies for PEPC-mediated $CO_2$ fixation, which are shared with two monocot CAM species, *A. comosus* and *P. equestris*, respectively.

Ever-increasing human population and predicted global warming create grand challenges for sustainable supply of food, feed, fiber, and fuel in the years to come. As a proven mechanism for increasing WUE in plants, CAM offers great potential for solve these challenges and CAM-into-$C_3$ engineering could be a viable strategy to improve WUE in existing non-CAM crops for food and biomass production in dryland areas (Yang et al., 2015, *New Phytologist*, 207: 491-504). The genes predicted to be involved in CAM convergent evolution in this study could be excellent candidates for CAM-into-$C_3$ engineering. There is no overlap between the list containing 118 genes with convergent changes in transcript expression pattern (Table 1) and the list containing 8 genes with convergent changes in protein sequence (Table 3), leading to a hypothesis that dual selection on both protein sequence and cis-regulatory elements did not occur on the same gene and rewiring of the temporal transcript expression pattern has played a major role in CAM convergent evolution. An implication of this hypothesis is that the CAM-into-$C_3$ engineering (CAM engineering) efforts need to be focused on changing the temporal transcript expression pattern of the endogenous gene in the target species corresponding to the *K. fedtschenkoi* genes listed in Table 1. In some embodiments, to make the protein sequence changes needed for CAM-into-C3 engineering, the *K. fedtschenkoi* genes listed in Table 1 can be transferred to the target C3 species using the classic *Agrobacterium*-mediated transformation approach. Alternatively, the PEPC2 in *K. fedtschenkoi* could bypasses the need for activation by PPCK1 (FIG. 5B), leading to a new strategy for CAM-into-C3 engineering based on transferring *K. fedtschenkoi* PEPC2 into the $C_3$ crops or creating the "R-to-D" mutation in PEPC1 as indicated in FIG. 5B.

CRISPR/Cas9-based knock-in approach can be used to replace the original endogenous promoters of the target genes with temporal promoters that confer temporal expression patterns similar to those of their orthologous genes in the CAM species. For example, dark-inducible promoters such as Din10 (Fujiki, Y. et al., 2001, *Physiol. Plant.*, 111, 345-352) can be used to drive the expression of carboxylation gene modules during the nighttime and light-inducible promoters, such as GT1-GATA-NOS101 (Puente, P. et al., *EMBO J.*, 15, 3732 (1996)), can be used to drive the expression of decarboxylation gene modules during the daytime.

Example 14

Sequences of Selected Genes

SEQ ID NO: 1; Gene name: XmoPEPC2; Description: Phosphoenolpyruvate carboxylase 2; NCBI accession #: AAM95946; Source: x Mokara cv. 'Yellow'.

SEQ ID NO: 2; Gene name: PheqPEPC2; Description: Phosphoenolpyruvate carboxylase 2; NCBI accession #: XP_020584551; Source: *Phalaenopsis equestris*.

SEQ ID NO: 3; Gene name: Kaladp0011s0355.1; Description: Phosphoenolpyruvate carboxylase 2; NCBI accession #: Not available; Source: *Kalanchoe fedtschenkoi*.

SEQ ID NO: 4; Gene name: Kaladp0048s0578.1; Description: Phosphoenolpyruvate carboxylase 2; NCBI accession #: Not available; Source: *Kalanchoe fedtschenkoi*.

SEQ ID NO: 5; Gene name: Kalax.0104s0064.1; Description: Phosphoenolpyruvate carboxylase 2; NCBI accession #: Not available; Source: *Kalanchoe laxiflora*.

SEQ ID NO: 6; Gene name: Kalax.0283s0047.1; Description: Phosphoenolpyruvate carboxylase 2; NCBI accession #: Not available; Source: *Kalanchoe laxiflora*.

SEQ ID NO: 7; Gene name: Kalax.0445s0035.1; Description: Phosphoenolpyruvate carboxylase 2; NCBI accession #: Not available; Source: *Kalanchoe laxiflora*.

SEQ ID NO: 8; Gene name: Kalax.0510s0003.1; Description: Phosphoenolpyruvate carboxylase 2; NCBI accession #: Not available; Source: *Kalanchoe laxiflora*.

SEQ ID NO: 9; Gene name: ZemaPEPC2; Description: Phosphoenolpyruvate carboxylase 2; NCBI accession #: PWZ12751.1; Source: *Zea mays*.

SEQ ID NO: 10; Gene name: PotrPEPC; Description: Phosphoenolpyruvate carboxylase; NCBI accession #: XP_024436919.1; Source: *Populus trichocarpa*.

SEQ ID NO: 11; Gene name: BrolPEPC1; Description: Phosphoenolpyruvate carboxylase 1; NCBI accession #: XP_013628861.1; Source: *Brassica oleracea*.

SEQ ID NO: 12; Gene name: BrraPEPC1; Description: Phosphoenolpyruvate carboxylase 1; NCBI accession #: XP_009106983.1; Source: *Brassica rapa*.

SEQ ID NO: 13; Gene name: MadoPEPC2; Description: Phosphoenolpyruvate carboxylase 2; NCBI accession #: XP_008362419.1; Source: *Malus domestica*.

SEQ ID NO: 14; Gene name: GlmaPEPC2; Description: Phosphoenolpyruvate carboxylase 2; NCBI accession #: XP_003527347.1; Source: *Glycine max*.

SEQ ID NO: 15; Gene name: Kaladp0059s0286.1; Description: Heat shock 40 kDa protein; NCBI accession #: Not available; Source: *Kalanchoe fedtschenkoi*.

SEQ ID NO: 16; Gene name: Aco006149.1; Description: Heat shock 40 kDa protein; NCBI accession #: Not available; Source: *Ananas comosus*.

SEQ ID NO: 17; Gene name: Kaladp0073s0051.1; Description: Heat shock 60 kDa protein; NCBI accession #: Not available; Source: *Kalanchoe fedtschenkoi*.

SEQ ID NO: 18; Gene name: Aco010414.1; Description: Heat shock 60 kDa protein; NCBI accession #: Not available; Source: *Ananas comosus*.

SEQ ID NO: 19; Gene name: Aco010207.1; Description: Heat shock 60 kDa protein; NCBI accession #: Not available; Source: *Ananas comosus*.

SEQ ID NO: 20; Gene name: Aco015991.1; Description: Heat shock 60 kDa protein; NCBI accession #: Not available; Source: *Ananas comosus*.

SEQ ID NO: 21; Gene name: Kaladp0060s0296.1; Description: Heat shock 70 kDa protein; NCBI accession #: Not available; Source: *Kalanchoe fedtschenkoi*.

SEQ ID NO: 22; Gene name: Kaladp0039s0620.1; Description: Heat shock 70 kDa protein; NCBI accession #: Not available; Source: *Kalanchoe fedtschenkoi*.

SEQ ID NO: 23; Gene name: Aco031458.1; Description: Heat shock 70 kDa protein; NCBI accession #: Not available; Source: *Ananas comosus*.

SEQ ID NO: 24: amino acids 489-538 of Kaladp0048s0578.1 (SEQ ID NO: 4).

SEQ ID NO: 25: amino acids 489-538 of Kaladp0011s0355.1 (SEQ ID NO: 3).

SEQ ID NO: 26: amino acids 489-538 of Kalax.0104s0064.1 (SEQ ID NO: 5).

SEQ ID NO: 27: amino acids 489-538 of Kalax.0283s0047.1 (SEQ ID NO: 6).

SEQ ID NO: 28: amino acids 489-538 of Kalax.0445s0035.1 (SEQ ID NO: 7).

SEQ ID NO: 29: amino acids 489-538 of Kalax.0510s0003.1 (SEQ ID NO: 8).

SEQ ID NO: 30: amino acids 489-538 of AAM95946.1 (SEQ ID NO: 1).

SEQ ID NO: 31: amino acids 489-538 of XP_020584551.1 (SEQ ID NO: 2).

SEQ ID NO: 32: amino acids 489-538 of PWZ12751.1 (SEQ ID NO: 9).

SEQ ID NO: 33: amino acids 489-538 of XP_024436919.1 (SEQ ID NO: 10).

SEQ ID NO: 34: amino acids 489-538 of XP_013628861.1 (SEQ ID NO: 11).

SEQ ID NO: 35: amino acids 489-538 of XP_009106983.1 (SEQ ID NO: 12).

SEQ ID NO: 36: amino acids 489-538 of XP_008362419.1 (SEQ ID NO: 13).

SEQ ID NO: 37: amino acids 489-538 of XP_003527347.1 (SEQ ID NO: 14).

---

What is claimed is:

1. A method of improving drought and heat tolerance in a plant or plant cell, comprising introducing into the plant or plant cell an exogenous nucleic acid encoding at least one heat shock protein (HSP) selected from the group consisting of HSP40, HSP60 and HSP70, and further expressing in the plant an exogenous nucleic acid encoding a phosphoenolpyruvate carboxylase (PEPC) comprising an aspartic acid (D) at a position corresponding to position 509 of SEQ ID NO: 4.

2. A method of improving drought and heat tolerance in a plant or plant cell, comprising introducing into the plant or plant cell an exogenous nucleic acid encoding at least one heat shock protein (HSP) selected from the group consisting of HSP40, HSP60 and HSP70, and further expressing an exogenous nucleic acid encoding a phosphoenolpyruvate carboxylase (PEPC) of a CAM plant species selected from the group consisting of genera *Kalanchoe Phalaenopsis, Ananas* and *Crassula*.

3. A method of improving drought and heat tolerance in a plant or plant cell, comprising introducing into the plant or plant cell an exogenous nucleic acid encoding at least one heat shock protein (HSP) selected from the group consisting of HSP40, HSP60 and HSP70, and further introducing a mutation into an endogenous phosphoenolpyruvate carboxylase (PEPC) gene wherein the resulting mutated gene encodes a PEPC comprising an aspartic acid (D) at a position corresponding to position 509 of SEQ ID NO: 4.

4. The method of claim 3, wherein the mutation is introduced by genome editing, which is achieved by a method selected from the group consisting of CRISPR/Cas system, Cre/Lox system, TALEN system, ZFNs system and homologous recombination.

5. The method of claim 4, wherein said CRISPR/Cas system comprises introducing into the plant or plant cell a first nucleic acid encoding a Cas9 or Cas12 nuclease, a second nucleic acid comprising a guide RNA (gRNA), and a third nucleic acid comprising a homologous repair template of a PEPC gene wherein the third nucleic acid encodes an aspartic acid (D) at a position corresponding to position 509 of SEQ ID NO: 4.

6. The method of claim 1, wherein the exogenous nucleic acid encoding at least one HSP is expressed during daytime and the nucleic acid encoding PEPC is expressed during night time.

7. The method of claim 1, wherein the exogenous nucleic acid encoding at least one HSP and nucleic acid encoding PEPC are expressed constitutively.

8. The method of claim 1, wherein the exogenous nucleic acid encoding at least one HSP is stably transfected or transformed into the plant or plant cell genome.

9. The method of claim 1, wherein the exogenous nucleic acid encoding at least one HSP is expressed in the leaf tissue.

10. The method of claim 1, wherein the plant is a C3 plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia* and *Triticum*.

11. The method of claim 1, wherein the plant is a C4 plant selected from the group consisting of genera *Panicum, Saccharum, Setaria, Sorghum* and *Zea*.

12. The method of claim 1, wherein at least two of the HSP40, HSP60 and HSP70 are expressed simultaneously in the plant or plant cell.

13. A genetically modified plant or plant cell produced by the method of claim 1.

14. A genetically-modified plant or plant cell, wherein the plant or plant cell is modified to express an exogenous nucleic acid encoding at least one heat shock protein (HSP) selected from the group consisting of HSP40, HSP60 and HSP70, and wherein the plant or plant cell is further modified to express a nucleic acid encoding a phosphoenolpyruvate carboxylase (PEPC) comprising an aspartic acid (D) at a position corresponding to position 509 of SEQ ID NO: 4.

15. The genetically-modified plant or plant cell of claim 14, wherein the PEPC is expressed from the endogenous PEPC gene mutated to encode an aspartic acid (D) at a position corresponding to position 509 of SEQ ID NO: 4.

16. The genetically-modified plant or plant cell of claim 14, wherein the exogenous nucleic acid encoding at least one HSP is expressed during daytime and the nucleic acid encoding PEPC is expressed during night time.

17. The genetically-modified plant or plant cell of claim 14, wherein the plant is a C3 plant or a C4 plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia, Triticum, Panicum, Saccharum, Setaria, Sorghum,* and *Zea*.

18. An expression vector, comprising a nucleotide sequence operably linked to a regulatory region that is functional in a plant or plant cell, wherein the nucleotide sequence encodes a heat shock protein (HSP) selected from the group consisting of HSP40, HSP60, HSP70, and a phosphoenolpyruvate carboxylase (PEPC) comprising an aspartic acid (D) at a position corresponding to position 509 of SEQ ID NO: 4.

19. The expression vector of claim 18, wherein the expression vector directs temporally controlled expression of the nucleotide sequence.

20. The expression vector of claim 19, wherein the temporally controlled expression comprises gene expression during nighttime.

21. The expression vector of claim 19, wherein the temporally controlled expression comprises gene expression during daytime.

22. The expression vector of claim 18, wherein the regulatory region comprises a promoter selected from the group consisting of a constitutive promoter, a tissue-specific promoter, and a regulated promoter.

23. The expression vector of claim 22, wherein the tissue-specific promoter is a leaf-specific promoter.

24. The expression vector of claim 23, wherein the leaf-specific promoter is selected from the group consisting of a ribulose-1,5-bisphosphate carboxylase/oxygenase (RbcS) promoter, a chlorophyll a/b binding-6 (cab6) promoter, a chlorophyll a/b binding-1(Cab-1) promoter, a cab IR promoter from rice, a pyruvate orthophosphate dikinase (PPDK) promoter, a light-harvesting complex of photosystem (Lhcb1*2) promoter, a sucrose-H+ symporter (SUC2) promoter and a thylakoid membrane protein promoter.

25. The expression vector of claim 22, wherein the constitutive promoter is selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

26. The expression vector of claim 22, wherein the regulated promoter is selected from the group consisting of a stress induced promoter, a chemical-induced promoter, a light induced promoter, a dark-induced promoter, and a circadian-clock controlled promoter.

27. A method for improving drought and heat tolerance in a plant or plant cell, comprising introducing the expression vector of claim 18 into a plant or plant cell, and expressing the nucleotide sequence in the plant or plant cell.

28. A plant or plant cell comprising the expression vector of claim 18.

* * * * *